(12) United States Patent
Tsujita

(10) Patent No.: US 11,134,921 B2
(45) Date of Patent: *Oct. 5, 2021

(54) ULTRASONIC DIAGNOSTIC DEVICE AND ULTRASONIC THREE-DIMENSIONAL IMAGE GENERATION METHOD

(71) Applicant: HITACHI, LTD., Tokyo (JP)

(72) Inventor: Takehiro Tsujita, Tokyo (JP)

(73) Assignee: HITACHI, LTD., Tokyo (JP)

(*) Notice: Subject to any disclaimer, the term of this patent is extended or adjusted under 35 U.S.C. 154(b) by 1175 days.

This patent is subject to a terminal disclaimer.

(21) Appl. No.: 14/776,775

(22) PCT Filed: Apr. 11, 2014

(86) PCT No.: PCT/JP2014/060554
§ 371 (c)(1),
(2) Date: Sep. 15, 2015

(87) PCT Pub. No.: WO2014/168249
PCT Pub. Date: Oct. 16, 2014

(65) Prior Publication Data
US 2016/0030007 A1  Feb. 4, 2016

(30) Foreign Application Priority Data

Apr. 12, 2013 (JP) .............................. JP2013-084151

(51) Int. Cl.
*A61B 8/08* (2006.01)
*G06T 15/08* (2011.01)
(Continued)

(52) U.S. Cl.
CPC .......... *A61B 8/5246* (2013.01); *A61B 5/0095* (2013.01); *A61B 8/06* (2013.01);
(Continued)

(58) Field of Classification Search
CPC ......... A61B 8/5246; A61B 8/06; A61B 8/466; A61B 8/483; A61B 8/485; A61B 4/0866;
(Continued)

(56) References Cited

U.S. PATENT DOCUMENTS 8,477,135 B2  7/2013  Thiele
8,988,462 B2  3/2015  Tsujita
(Continued)

FOREIGN PATENT DOCUMENTS

CN  101454806 A  6/2009
CN  102753103 A  10/2012
(Continued)

OTHER PUBLICATIONS

May 27, 2014 International Search Report issued in International Patent Application No. PCT/JP2014/060554.

*Primary Examiner* — Patricia J Park
(74) *Attorney, Agent, or Firm* — Oliff PLC

(57) ABSTRACT

An ultrasonic diagnostic device and ultrasonic three-dimensional image generation method generate a three-dimensional image by expressing interaction by dispersion, absorption, or the like of light in tissue or between tissues. The ultrasonic diagnostic device displays a three-dimensional image of a target object based on at least one piece of volume data among luminance volume data, blood flow volume data, and elasticity volume data. The ultrasonic diagnostic device includes: a light source setting unit to set light source data indicating characteristics of a light source set in a three-dimensional space; an optical characteristic setting unit to set characteristics of the volume data related to the light source; an illumination calculation unit calculates illumination of coordinates of the volume data based on the light source data and optical characteristics and generate illumination volume data based on calculated illumination;

(Continued)

and a projection processing unit generates the three-dimensional image from the illumination volume data.

16 Claims, 21 Drawing Sheets

(51) Int. Cl.
    *A61B 8/06*     (2006.01)
    *A61B 5/00*     (2006.01)
    *A61B 8/00*     (2006.01)
    *A61B 8/13*     (2006.01)

(52) U.S. Cl.
    CPC .............. *A61B 8/466* (2013.01); *A61B 8/483* (2013.01); *A61B 8/485* (2013.01); *G06T 15/08* (2013.01); *A61B 5/742* (2013.01); *A61B 8/0866* (2013.01); *A61B 8/13* (2013.01); *A61B 8/463* (2013.01); *A61B 8/488* (2013.01); *A61B 8/5207* (2013.01); *A61B 2576/00* (2013.01); *G06T 2210/41* (2013.01)

(58) Field of Classification Search
    CPC ....... A61B 8/463; A61B 8/488; A61B 8/5207; A61B 5/0095; A61B 5/742; G06T 15/08; G06T 2210/41
    See application file for complete search history.

(56) References Cited

U.S. PATENT DOCUMENTS

| | | | |
|---|---|---|---|
| 2008/0260227 A1* | 10/2008 | Hayashi | ................... A61B 8/06 382/131 |
| 2009/0184955 A1* | 7/2009 | Thiele | ..................... G06T 15/08 345/419 |
| 2009/0198128 A1* | 8/2009 | Fukutani | .............. A61B 5/0091 600/437 |
| 2010/0185091 A1* | 7/2010 | Sumi | ........................ A61B 8/08 600/443 |
| 2012/0041312 A1* | 2/2012 | Nakahira | .................. G06T 5/50 600/443 |
| 2012/0087564 A1 | 4/2012 | Tsujita | |
| 2012/0287156 A1* | 11/2012 | Tsujita | ..................... A61B 8/06 345/629 |
| 2013/0109949 A1* | 5/2013 | Li | ...................... G01N 21/4738 600/407 |
| 2013/0150719 A1* | 6/2013 | Orderud | ................. G06T 15/08 600/443 |
| 2014/0071132 A1 | 3/2014 | Noshi et al. | |

FOREIGN PATENT DOCUMENTS

| | | |
|---|---|---|
| CN | 102893308 A | 1/2013 |
| JP | 2006-130071 A | 5/2006 |
| WO | 2010/143587 A1 | 12/2010 |
| WO | 2011/099410 A1 | 8/2011 |
| WO | 2012/157493 A1 | 11/2012 |

\* cited by examiner

ULTRASONIC DIAGNOSTIC DEVICE AND ULTRASONIC THREE-DIMENSIONAL IMAGE GENERATION METHOD

TECHNICAL FIELD

The present invention relates to an ultrasonic diagnostic device, and particularly, to an ultrasonic diagnostic device generating a three-dimensional projection image from at least one of a plurality of pieces of ultrasonic volume data.

BACKGROUND ART

Ultrasonic diagnostic devices transmit ultrasonic waves to the insides of objects by ultrasonic probes, receive reflected echo signals of the ultrasonic waves according to the structures of biological tissues from the insides of the objects, and construct, for example, luminance tomographic images such as ultrasonic tomographic images (B mode images) to display the luminance tomographic images for diagnosis.

When three-dimensional ultrasonic data is collected, technologies for observing the surfaces of target objects by performing coordinate conversion on three-dimensional data obtained when probes are automatically or manually scanned in shorter-axis directions, subsequently reconstructing ultrasonic image data in visual line directions, and generating three-dimensional images have been generally used.

At present, technologies called real-time 3D or 4D are generally used to display three-dimensional moving images by performing signal processing on reflected echo signals in real time.

Such three-dimensional images are excellent in surface shape rendering abilities, and thus are effective in diagnosis of diseases of fissures (lips, cleft palates, and the like) on skins which are difficult to diagnose from ultrasonic tomographic images showing one cross section.

However, since many artifacts peculiar to ultrasonic waves, such as speckle noise are present in ultrasonic images, image quality is improved through smoothing processes or the like. However, there is an adverse effect in which boundaries become continuous due to the smoothing processes, and thus fissures on skins are continuously displayed.

As a method of resolving this problem in an image processing device which can display a three-dimensional image, there is an image processing device capable of obtaining a combined three-dimensional image with excellent image quality by causing structure understanding of an inspection target object and extraction of a surface shape to be compatible (for example, see PTL 1).

Further, three-dimensional blood flow data or three-dimensional hardness data can be collected from reflected echo signals using a Doppler method and a three-dimensional image of the blood flow data or the hardness data can be generated (for example, see PTL 2).

CITATION LIST

Patent Literature

[PTL 1] JP-A-2006-130071
[PTL 2] WO2011/099410

SUMMARY OF INVENTION

Technical Problem

However, in ultrasonic diagnostic devices (image processing devices) of the related art, excellent image quality can be obtained by causing structure understanding of an inspection target object and the extraction of the surface shape to be compatible. However, images of which reality is improved through shades or the like by setting light sources in volume rendering methods as in optical photos could not be obtained.

In ultrasonic diagnostic devices (image processing devices) of the related art, three-dimensional images proper for structure recognition can be generated while changing positional relations between three-dimensional luminance data corresponding to tissue structures and three-dimensional blood flow data corresponding to vascular structures at scales called contribution ratios. However, three-dimensional images of which reality is improved in consideration of optical interaction between tissues with different natures (for example, between tissues such as skin tissues, fat tissues, blood vessels, and tumor tissues) could not be obtained.

The present invention is devised to resolve the foregoing problems and an object of the present invention is to provide an ultrasonic diagnostic device that generates a three-dimensional image of which reality is improved by expressing a behavior (leakage, absorption, diffusion, reflection, or the like) of light in tissues, reproducing shades behind tissues or local shades occurring in fissures of skins, and expressing shade effects by leakage, absorption, or the like of light. Further, the present invention is devised to resolve the foregoing problems and another object of the present invention is to provide an ultrasonic diagnostic device that generates a three-dimensional image of which reality is improved by expressing a behavior of light in tissues and expressing interaction of light between tissues with different natures.

Solution to Problem

According to an aspect of the present invention, there is provided an ultrasonic diagnostic device that displays a three-dimensional image of a target object based on at least one piece of volume data among luminance volume data, blood flow volume data (including blood flow rate volume data, blood flow amplitude volume data, and blood flow dispersion volume data), and elasticity volume data. The ultrasonic diagnostic device includes: a light source information setting unit configured to set light source data indicating characteristics of a light source set in a three-dimensional space; an optical characteristic setting unit configured to set optical characteristics of the volume data in regard to the light source; an illumination calculation unit configured to calculate illumination of a position according to coordinates of the volume data based on the light source data and the optical characteristics and generate illumination volume data based on the calculated illumination; and a projection processing unit configured to generate the three-dimensional image from the illumination volume data.

Advantageous Effects of Invention

The present invention can provide an ultrasonic diagnostic device that generates a three-dimensional image of which reality is improved by expressing interaction by diffusion, absorption, and the like of light in a tissue or between different tissues.

DESCRIPTION OF EMBODIMENTS

First Embodiment

Figure 1:
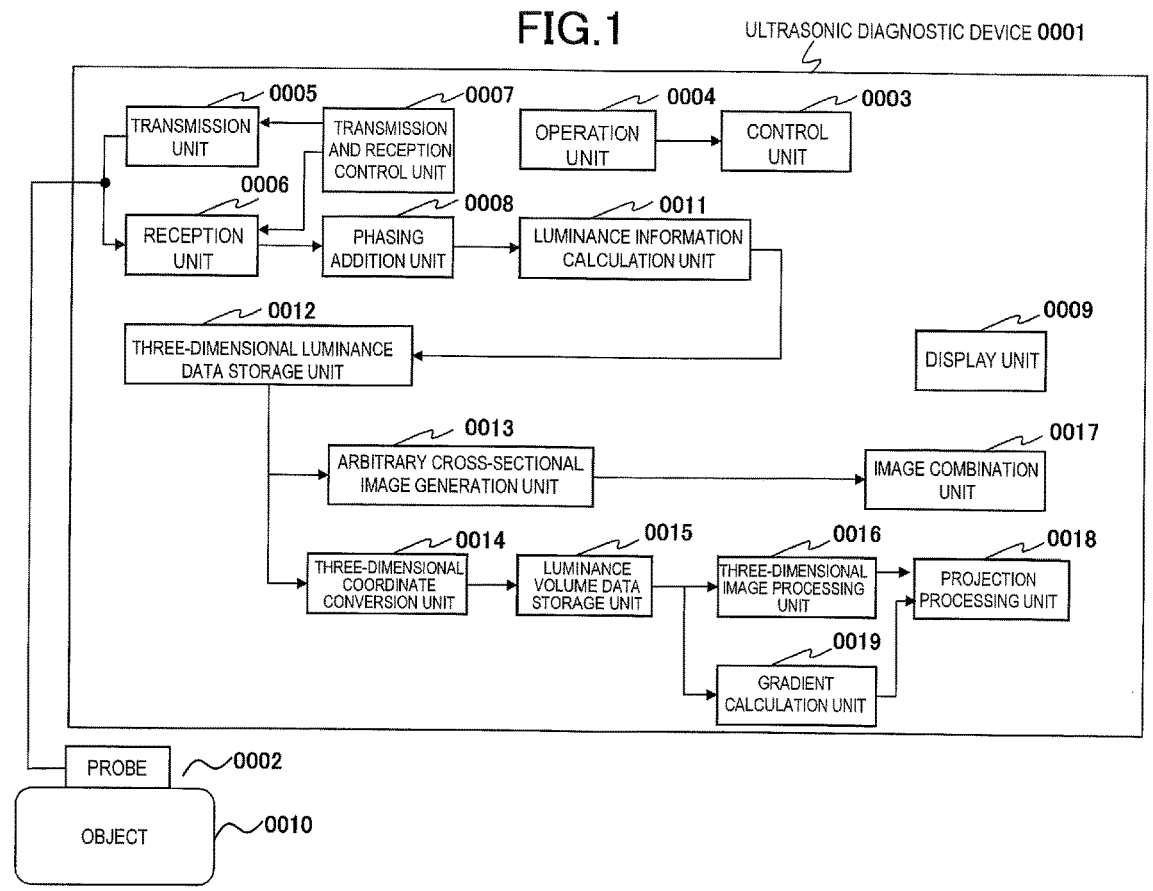
FIG. 1 is a block diagram illustrating an example of an ultrasonic diagnostic device according to a first embodiment.

Hereinafter, an ultrasonic diagnostic device according to a first embodiment of the present invention will be described with reference to the drawings. FIG. 1 is a block diagram illustrating an example of the ultrasonic diagnostic device according to the embodiment. As illustrated in FIG. 1, an ultrasonic diagnostic device 0001 includes a control unit 0003, an operation unit 0004, a transmission unit 0005, a reception unit 0006, a transmission and reception control unit 0007, a phasing addition unit 0008, a display unit 0009, a luminance information calculation unit 0011, a three-dimensional luminance data storage unit 0012, an arbitrary cross-sectional image generation unit 0013, a three-dimensional coordinate conversion unit 0014, a luminance volume data storage unit 0015, a three-dimensional image processing unit 0016, an image combination unit 0017, a projection processing unit 0018, and a gradient calculation unit 0019. The ultrasonic diagnostic device 0001 displays a three-dimensional image of a target object based on luminance volume data. An ultrasonic probe 0002 is connected to the ultrasonic diagnostic device 0001.

The ultrasonic probe 0002 is brought into contact with an object 0010 for use. The ultrasonic probe 0002 is formed such that a plurality of vibrators are arranged and has a function of transmitting and receiving ultrasonic waves via the vibrators to and from the object 0010. The ultrasonic probe 0002 is configured to include the plurality of vibrators formed in a one-dimensional straight-line shape or linear shape, and can electrically transmit and receive ultrasonic waves in the arrangement direction of the probe and simultaneously transmit and receive ultrasonic waves three-dimensionally by mechanically vibrating or manually moving the vibrators in a direction perpendicular to the arrangement direction of the plurality of vibrators. The ultrasonic probe 0002 may be configured such that the plurality of vibrators are arranged two-dimensionally and can electrically control transmission and reception of ultrasonic waves.

The control unit 0003 controls each constituent element of the ultrasonic diagnostic device 0001 and the ultrasonic probe 0002. The operation unit 0004 performs various inputs to the control unit 0003. The operation unit 0004 includes a keyboard or a track ball.

The transmission unit 0005 repeatedly transmits ultrasonic waves to the object 0010 via the ultrasonic probe 0002 at constant time intervals. The transmission unit 0005 drives the vibrators of the ultrasonic probe 0002 to generate transmission wave pulses for generating ultrasonic waves. The transmission unit 0005 has a function of setting a convergent point of the ultrasonic waves to be transmitted at a certain depth. The reception unit 0006 receives reflected echo signals reflected from the object 0010. The reception unit 0006 amplifies the reflected echo signals received by the ultrasonic probe 0002 at a predetermined gain to generate RF signals, that is, received signals. The transmission and reception control unit 0007 controls the transmission unit 0005 and the reception unit 0006.

The phasing addition unit 0008 performs phasing addition on the reflected echo signals received by the reception unit 0006. The phasing addition unit 0008 controls the phases of the RF signals amplified by the reception unit 0006 to form ultrasonic beams at one convergent point or a plurality of convergent points and generates RF signal frame data (corresponding to RAW data). The luminance information calculation unit 0011 constructs a tomographic image based on the RF signal frame data generated by the phasing addition unit 0008. The three-dimensional luminance data storage unit 0012 stores a plurality of tomographic images formed by the luminance information calculation unit 0011.

The arbitrary cross-sectional image generation unit 0013 generates an arbitrary cross-sectional image based on the acquired shape of the tomographic image. The three-dimensional coordinate conversion unit 0014 performs three-dimensional coordinate conversion based on the acquired shape of the tomographic image to generate luminance volume data and stores the luminance volume data in the luminance volume data storage unit 0015. The three-dimensional image processing unit 0016 generates illumination volume data using the luminance volume data stored in the luminance volume data storage unit 0015.

The gradient calculation unit 0019 generates gradient volume data using the luminance volume data stored in the luminance volume data storage unit 0015. A gradient value of the gradient volume data (the luminance gradient volume data) is a value indicating a slope (for example, a slope of a normal line in a three-dimensional shape or an angle between the normal line in the three-dimensional shape and a light source direction) of a three-dimensional shape calculated based on a luminance value. The projection processing unit 0018 generates a three-dimensional image by performing a rendering process using the illumination volume data, the luminance volume data, and the gradient volume data (luminance gradient volume data). The projection processing unit 0018 may also generate a three-dimensional image from the luminance volume data and the illumination volume data. The image combination unit 0017 combines the three-dimensional image generated by the projection processing unit 0018 and the arbitrary cross-sectional image (arbitrary cross-sectional image of three-dimensional luminance data) generated by the arbitrary cross-sectional image generation unit 0013. The display unit 0009 displays a display image generated by the image combination unit 0017.

Next, a process for the three-dimensional data will be described. The ultrasonic probe 0002 can transmit and receive the ultrasonic waves and can perform measurement along two axes of, for example, $\theta$ and $\phi$ while switching transmission and reception directions two-dimensionally. The luminance information calculation unit 0011 constructs two-dimensional tomographic data by inputting the RF signal frame data output from the phasing addition unit 0008 based on a setting condition in the control unit 0003 and performing signal processing such as gain correction, log compression, detection, contour enhancement, and a smoothing process.

The three-dimensional luminance data storage unit 0012 has a function of storing a plurality of pieces of two-dimensional tomographic data, which is output data of the luminance information calculation unit 0011, based on transmission and reception directions corresponding to acquisition positions. For example, a plurality of pieces of two-dimensional tomographic data obtained by driving and acquiring a plurality of two-dimensional tomographic images, generated from measurement results when time-series ultrasonic data sampled in a depth direction is transmitted and received in a $\theta$ direction, in a $\phi$ direction orthogonal to the $\theta$ direction in association with $\phi$ are stored as three-dimensional tomographic data.

The three-dimensional coordinate conversion unit 0014 performs three-dimensional coordinate conversion on coordinates in a space based on the acquisition positions (depth, $\theta$, $\phi$) using the three-dimensional tomographic data stored in the three-dimensional luminance data storage unit 0012, generates luminance volume data, and stores the luminance volume data in the luminance volume data storage unit 0015.

The arbitrary cross-sectional image generation unit 0013 generates an arbitrary cross-sectional image on an arbitrary plane in a three-dimensional space set by the control unit 0003 and the operation unit 0004 based on the acquisition positions (depth, $\theta$, $\phi$) using the three-dimensional tomographic data stored in the three-dimensional luminance data storage unit 0012.

The three-dimensional image processing unit 0016 generates illumination volume data based on the luminance volume data stored in the luminance volume data storage unit 0015. The gradient calculation unit 0019 generates volume data in which a gradient in a visual line direction at respective voxel coordinates is calculated based on the luminance volume data stored in the luminance volume data storage unit 0015.

Next, a process of the three-dimensional image processing unit 0016 will be described. The three-dimensional image processing unit 0016 is a characteristic processing unit of the ultrasonic diagnostic device 0001 according to the embodiment and generates illumination volume data based on a light source in the three-dimensional space set by the control unit 0003 and the operation unit 0004, using the luminance volume data stored in the luminance volume data storage unit 0015.

Figure 2:
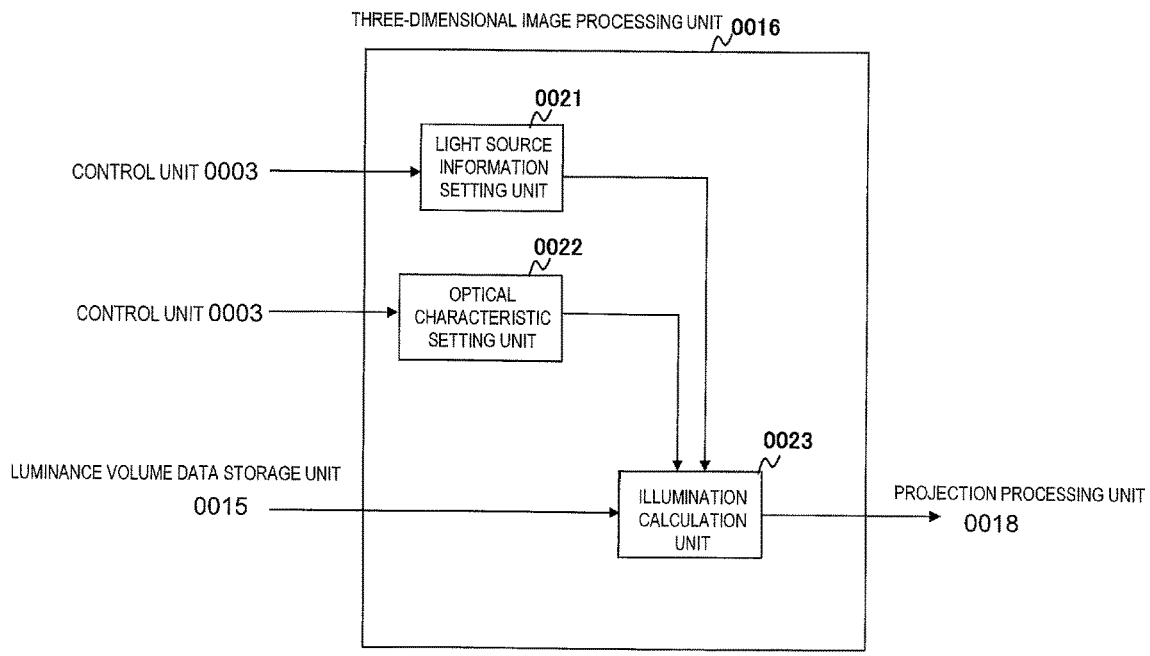
FIG. 2 is a block diagram illustrating an example of a three-dimensional image processing unit according to the first embodiment.

FIG. 2 is a block diagram illustrating an example of the three-dimensional image processing unit 0016. As illustrated in FIG. 2, the three-dimensional image processing unit 0016 includes a light source information setting unit 0021, an optical characteristic setting unit 0022, and an illumination calculation unit 0023. The ultrasonic diagnostic device 0001 according to the embodiment is the ultrasonic diagnostic device 0001 that displays a three-dimensional image of a target object based on volume data (luminance volume data). The ultrasonic diagnostic device 0001 includes the light source information setting unit 0021 that sets light source data indicating the characteristics of a light source set in a three-dimensional space, the optical characteristic setting unit 0022 that sets optical characteristics (or a weight coefficient indicating optical characteristics) of the volume data in regard to the light source, the illumination calculation unit 0023 that calculates illumination of a position according to coordinates of the volume data based on the light source data and the optical characteristics (or the weight coefficient) and generates illumination volume data based on the calculated illumination, and the projection processing unit 0018 that generates the three-dimensional image from the illumination volume data. A method of generating an ultrasonic three-dimensional image according to the embodiment is an ultrasonic wave three-dimensional image generation method of displaying a three-dimensional image of a target object based on volume data. The method includes setting light source data indicating characteristics of a light source set in a three-dimensional space, setting a weight coefficient indicating optical characteristics of the volume data in regard to the light source, calculating illumination of a position according to coordinates of the volume data based on the light source data and the weight coefficient, generating illumination volume data based on the calculated illumination, and generating the three-dimensional image from the illumination volume data. In the embodiment, the volume data is the luminance volume data. However, the volume data may be at least one of the luminance volume data, blood flow volume data (including blood flow rate volume data, blood flow amplitude volume data, and blood flow dispersion volume data), and elasticity volume data. The blood flow dispersion volume data includes blood flow rate dispersion volume data and blood flow amplitude dispersion volume data.

The light source information setting unit 0021 sets (generates) light source data indicating the characteristics of the light source set in the three-dimensional space of the three-dimensional image. For example, the light source information setting unit 0021 sets light source data indicating strength of the light source. The light source information setting unit 0021 can also adjust at least one of the strength of the light source, a position of the light source in the three-dimensional space, a direction of the light source, color tone of the light source, and a shape of the light source to set the light source data. The optical characteristic setting unit 0022 sets the optical characteristics of the luminance volume data set by the control unit 0003 and the operation unit 0004. The optical characteristic setting unit 0022 sets a weight coefficient indicating the optical characteristics of the luminance volume data in regard to the light source. The illumination calculation unit 0023 calculates illumination corresponding to the coordinates of voxels on the luminance volume data based on the light source data set by the light source information setting unit 0021 and the optical characteristics set by the optical characteristic setting unit 0022 and generates illumination volume data. That is, the illumination calculation unit 0023 calculates the illumination of the position according to the coordinates of the luminance volume data based on the light source data and the weight coefficient and generates the illumination volume data based on the calculated illumination.

Next, light source information set by the light source information setting unit 0021, optical characteristics set by the optical characteristic setting unit 0022, and a method of generating the illumination volume data in the illumination calculation unit 0023 will be described.

Figure 3:
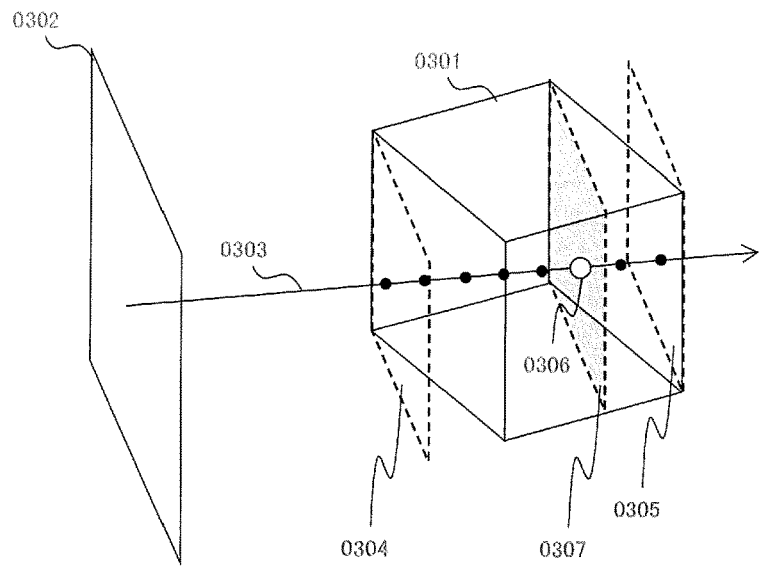
FIG. 3 is a conceptual diagram schematically illustrating a positional relation between luminance volume data and a light source.

FIG. 3 is a conceptual diagram schematically illustrating a positional relation between the luminance volume data and the light source. As illustrated in FIG. 3, a light source (parallel light source) 0302 is set in a light source direction 0303 in luminance volume data 0301 in the luminance volume data storage unit 0015 by the control unit 0003 and the operation unit 0004. The position of the light source 0302, the light source direction 0303, and light source data in a three-dimensional space are generated by the light source information setting unit 0021.

A plane 0304 indicates a position of a plane in which the luminance volume data 0301 first intersects (comes into contact with) an orthogonal plane in the light source direction 0303 and indicates an illumination calculation start position. A plane 0305 indicates a position of a plane in which the luminance volume data 0301 finally intersects (comes into contact with) an orthogonal plane in the light source direction 0303 and indicates an illumination calculation end position.

The illumination calculation unit 0023 performs illumination calculation on a plane (an orthogonal plane in the light source direction 0303) orthogonal in the light source direction 0303. In FIG. 3, the illumination calculation unit 0023 performs the illumination calculation in a scope from the plane 0304 to the plane 0305. For example, the illumination calculation unit 0023 performs illumination calculation on a plane 0307 in illumination calculation of a sample 0306 located in the light source direction 0303.

Figure 4:
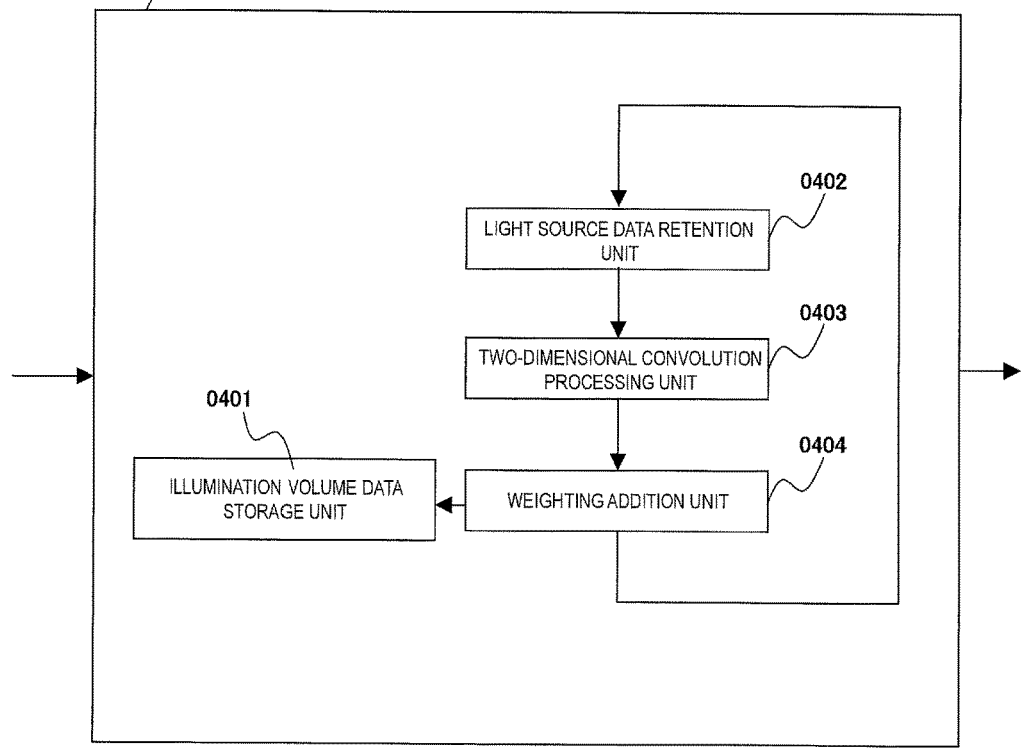
FIG. 4 is a block diagram illustrating an example of the configuration of an illumination calculation unit according to the first embodiment.

Next, an example of the configuration of the illumination calculation unit 0023 will be described with reference to FIG. 4. As illustrated in FIG. 4, the illumination calculation unit 0023 includes an illumination volume data storage unit 0401, a light source data retention unit 0402, a two-dimensional convolution processing unit 0403, and a weighting addition unit 0404. The illumination calculation unit 0023 includes the two-dimensional convolution processing unit 0403 that generates two-dimensional convolution integrated data by performing two-dimensional convolution integration on the light source data and the weighting addition unit 0404 that generates the illumination volume data by performing weighting addition (weighted sum) on the light source data and the two-dimensional convolution integrated data based on the weight coefficient.

The illumination calculation unit 0023 includes the light source data retention unit 0402 that retains an initial value of the light source data and a result of the weighting addition obtained by the weighting addition unit as input light source data. The illumination calculation unit 0023 generates two-dimensional convolution integrated data by performing two-dimensional convolution integration on the input light source data while switching voxels from the illumination calculation start position to the illumination calculation end position of the luminance volume data, and generates the illumination volume data by performing weighting addition on the input light source data and the two-dimensional convolution integrated data based on the weight coefficient.

The light source data retention unit 0402 inputs the light source data generated by the light source information setting unit 0021 and retains the light source data as an initial value. Hereinafter, the light source data retained by the light source data retention unit 0402 is referred to as "input light source data". The two-dimensional convolution processing unit 0403 generates the two-dimensional convolution integrated data by performing the two-dimensional convolution integration on the input light source data (light source data). The two-dimensional convolution integration process indicates convolution integration on a two-dimensional plane and is performed on, for example, the plane 0307.

The weighting addition unit 0404 inputs the two-dimensional convolution integrated data which is an output result of the two-dimensional convolution processing unit 0403 and inputs the input light source data retained by the light source data retention unit 0402. The weighting addition unit 0404 generates the illumination volume data by performing the weighting addition on the input light source data (light source data) and the two-dimensional convolution integrated data based on the weight coefficient. The weight coefficient used by the weighting addition unit 0404 is set as the optical characteristics of the luminance volume data in regard to the light source by the optical characteristic setting unit 0022. Hereinafter, a weighting addition result generated by the weighting addition unit 0404 is referred to as "output illumination data".

The output illumination data is stored at a position according to the coordinates of the voxels of the illumination volume data storage unit 0401. The output illumination data is input to the light source data retention unit 0402 and is stored (retained) as input light source data. That is, the light source data retention unit 0402 retains the initial value of the light source data and the result of the weighting addition by the weighting addition unit 0404 as the input light source data.

Here, the input light source data of the initial value is light source data set by the light source information setting unit 0021, and is input to the light source data retention unit 0402 to be set (retained) before the illumination calculation unit 0023 starts the illumination calculation.

The illumination calculation unit 0023 (the two-dimensional convolution processing unit 0403 and the weighting addition unit 0404) generates the two-dimensional convolution integrated data by performing the two-dimensional convolution integration on the input light source data, while switching the voxels corresponding to coordinates to be referred to from the illumination calculation start position (the plane 0304) to the illumination calculation end position (the plane 0305) of the luminance volume data, and generates the illumination volume data by performing the weighting addition on the input light source data and the two-dimensional convolution integrated data using the weight coefficient which is based on a luminance value, while changing the luminance corresponding to the coordinates to be referred to.

Figure 5:
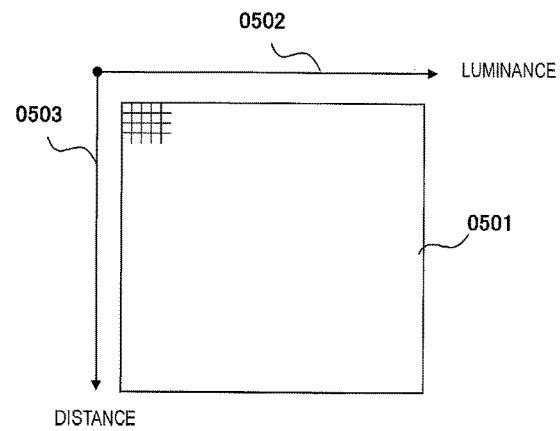
FIG. 5 is a diagram illustrating an example of a luminance two-dimensional weight coefficient table according to the first embodiment.

Next, a method of setting the weight coefficient used by the weighting addition unit 0404 will be described with reference to FIG. 5. As illustrated in FIG. 5, a two-dimensional weight coefficient table (luminance two-dimensional weight coefficient table) 0501 is a two-dimensional table which includes the weight coefficient set by the control unit 0003 and which is used to refer to the weight coefficient in which a luminance value (voxel value) 0502 of the luminance volume data and a distance 0503 from a body surface (or the surface of a tissue) are stored two-dimensionally as two indexes. That is, the weight coefficient is regulated by the two-dimensional weight coefficient table 0501 in which the luminance value of the luminance volume data and the distance from the surface of a target object are set as indexes. In this case, the optical characteristic setting unit 0022 sets the weight coefficient according to the luminance value of the luminance volume data and the distance from the surface of the target object.

The optical characteristics according to the embodiment are regulated by the weight coefficient set so that a behavior (action) of light is replicated based on the optical characteristics of a tissue and are set by the optical characteristic setting unit 0022. The optical characteristic setting unit 0022 sets the two-dimensional weight coefficient table 0501 that includes the weight coefficient as the optical characteristics of the luminance volume data.

As illustrated in FIG. 5, a case will be described in which the weight coefficients referred to from the two-dimensional weight coefficient table 0501 based on the two indexes, that is, the luminance value of the luminance volume data and the distance from the body surface (or the surface of a tissue) are two a and b. When the weight coefficient having an influence on (multiplied to) the input light source data is a and the weight coefficient having an influence on (multiplied to) the two-dimensional convolution integrated data is b, the behavior (the degree of diffusion or the like) of light can be simply set by adjusting the magnitudes of a and b.

A weighted sum of the input light source data and the two-dimensional convolution integrated data based on the weight coefficients a and b is output to the illumination volume data storage unit 0401. By setting the sum value of the weight coefficients a and b to be large, it is possible to set reinforced illumination. By setting the sum value of the weight coefficients a and b to be small, it is possible to set weak illumination.

In the embodiment, the two-dimensional weight coefficient table 0501 includes the luminance and the distance from a body surface (or the surface of a tissue) as two reference indexes. In the case of ultrasonic data, luminance reflecting acoustic impedance of a tissue can be useful information reflecting the characteristics of a biological tissue. Luminance in ultrasonic data reflects the amplitude of a reflected wave obtained by reflecting a radiated ultrasonic wave from a diffusing body, and thus is normally attenuated with propagation of the ultrasonic wave in a deep portion. Thus, in regard to the ultrasonic data, it is difficult to classify tissues based on only the luminance. Accordingly, by adding a distance from the body surface of a target object (or the surface of a tissue), it is possible to classify tissues in regard to the ultrasonic data.

For example, when a target object is an unborn child and an ultrasonic wave arriving at an arm of the unborn child via an amniotic water is considered, the luminance of the ultrasonic wave reflected from a diaphysis (hard tissue) of the arm is known to be high. However, the luminance at the moment at which the ultrasonic wave arrives at the surface of the arm is not attenuated even when the surface of the arm is a soft tissue. Therefore, the luminance is known to be high as in a diaphysis. Thus, when only the luminance is used as an index, it is difficult to distinguish a soft tissue from a diaphysis (hard tissue). Accordingly, a distance from the body surface of a target object is added as an index. A diaphysis is present inside a tissue of an unborn child. Therefore, by setting the characteristics of the tissue using both of luminance and a distance from a body surface (or the surface of a tissue), it is possible to discriminate the tissue.

For example, in regard to a distance from a body surface (or the surface of a tissue), when the luminance of a certain voxel is higher than a preset threshold value, the luminance is determined to correspond to a tissue, and thus a distance corresponding to 1 voxel is added as the value of the distance from the body surface (or the surface of the tissue). Conversely, when the luminance of a certain voxel is lower than the preset threshold value, the luminance is determined not to correspond to a tissue, and thus the value of the distance from the body surface (or the surface of the tissue) in the voxel is initialized.

A distance from a body surface (or the surface of a tissue) can be used as the index of the weight coefficient. Then, when a soft tissue with high luminance is present on the surface of a tissue as in an arm of an unborn child and a diaphysis with substantially the same luminance as the soft tissue is present at a deep position from the surface of a tissue, a different optical effect can be provided depending on a tissue despite substantially the same luminance by setting a different weight coefficient according to a distance from the body surface (or the surface of the tissue). That is, by distinguishing a soft tissue from a diaphysis (hard tissue) according to a distance from a body surface (or the surface of a tissue) and setting a different weight coefficient, a behavior (leakage, absorption, diffusion, reflection, or the like) of light in a tissue can be expressed so that the soft tissue is distinguished from the diaphysis (hard tissue), and thus an image (three-dimensional image) of which reality is improved can be obtained in a volume rendering method. By using a characteristic weight coefficient according to the characteristics of a tissue, a proper optical effect can be provided even when it is difficult to specify the characteristics (or kind) of the tissue by only the luminance value as in ultrasonic data.

In this way, by setting the two-dimensional weight coefficient table reflecting the characteristics of tissues without performing complicated calculation and adjusting a behavior (the degree of diffusion or the like) of light based on the two-dimensional weight coefficient table, optical effects in the tissues can be provided simply or arbitrarily, and thus a three-dimensional image of which reality is improved can be generated according to the characteristics (for example, hardness or softness of tissues) of the tissues.

The illumination calculation unit 0023 repeatedly performs the foregoing illumination calculation process while switching a luminance value (voxel luminance) corresponding to coordinates to be referred to by switching a voxel corresponding to the coordinates to be referred to by the weighting addition unit 0404 from the illumination calculation start position (the plane 0304) to the illumination calculation end position (the plane 0305).

The illumination calculation unit 0023 performs the calculation up to the illumination calculation end position to generate illumination volume data in which all of the illumination corresponding to voxel coordinates on the luminance volume data are calculated, and then stores the illumination volume data in the illumination volume data storage unit 0401.

The behavior characteristics of light differ depending on a wavelength of a light source according to the law of nature. Accordingly, when the reality is further improved in conformity to the law of nature, the illumination calculation is performed for each wavelength of the light source. In this case, the weight coefficients differ for each wavelength of the light source.

The light source information setting unit 0021 sets the light source data according to a plurality of wavelengths of the light source. The optical characteristic setting unit 0022 sets the weight coefficients for each of the plurality of wavelengths.

The illumination calculation unit 0023 performs the illumination calculation for each of the plurality of wavelengths of the light source 0302 to generate the illumination volume data. For example, when the light source 0302 is 7 colors of the visible light, the illumination calculation unit 0023 sets 7 kinds of weight coefficients (or two-dimensional weight coefficient tables) and generates 7 kinds of pieces of illumination volume data. When the light source 0302 is the three primary colors of additive color mixture, the illumination calculation unit 0023 sets three sets of weight coefficients (or three kinds of two-dimensional weight coefficient tables) corresponding to wavelengths of the R, G, and B components and generates three kinds of pieces of illumination volume data. That is, the light source information setting unit 0021 sets the light source data according to the plurality of wavelengths of the light source, the optical characteristic setting unit 0022 sets the weight coefficient for each of the plurality of wavelengths, and the illumination calculation unit 0023 generates the illumination volume data for each of the plurality of wavelengths.

In the embodiment, a case will be described in which the light source 0302 is the three primary colors of additive color mixture, three sets of weight coefficients (or three kinds of two-dimensional weight coefficient tables) are set, and three kinds of pieces of illumination volume data are generated. An initial value of the light source data is set for each wavelength of the light source 0302. That is, the same number of initial values of the light source data as the number of effective wavelengths is set by the light source information setting unit 0021. Accordingly, in the embodiment, three kinds of pieces of light source data corresponding to the wavelengths of the R, G, and B components are set and are each retained as independent input light source data by the light source data retention unit 0402. The initial values of the three kinds of pieces of light source data may be initial values selected via the operation unit 0004 by an operator or may be initial values set using an image.

The illumination calculation unit 0023 calculates the illumination disposed on the luminance volume data based on the three kinds of light source data and three kinds of optical characteristics (the weight coefficient or two-dimensional weight coefficient table) and generates three kinds of pieces of illumination volume data.

The projection processing unit 0018 generates a three-dimensional image based on opacity referred to by the illumination of the illumination volume data and the luminance (voxel value) of the luminance volume data. When the light source 0302 is the three primary colors, the projection processing unit 0018 generates the three-dimensional image from the three kinds of pieces of illumination volume data generated by the illumination calculation unit 0023 and the luminance volume data stored in the luminance volume data storage unit 0015. A projection process in the projection processing unit 0018 is performed based on illumination, opacity $\alpha[i]$, and gradient values $S[i]$ in illumination volume data $L\_r[k]$, $L\_g[k]$, and $L\_b[k]$ of the respective wavelengths (the R, G, and B components), as shown in equations (1) to (3) below, to generate the three-dimensional image. That is, the three-dimensional image is generated by multiplying voxel values in illumination volume data $L\_r[k]$, $L\_g[k]$, and $L\_b[k]$ of the respective wavelengths by opacity terms obtained by opacity $\alpha[i]$ and values of gradient values $S[i]$ and performing summation in a visual line direction. In the equations, "k" indicates voxel coordinates in the visual line direction. The visual line direction is set as a direction in which an ultrasonic image is observed via the control unit 0003 by the operation unit 0004.

$$OUT\_R[K] = \Sigma^{k=0:k}((L\_r[k] \cdot S[k]) \cdot \alpha[k] \cdot \Pi^{m=0:k-1}(1-\alpha[m])) \quad (1)$$

$$OUT\_G[K] = \Sigma^{k=0:k}((L\_g[k] \cdot S[k]) \cdot \alpha[k] \cdot \Pi^{m=0:k-1}(1-\alpha[m])) \quad (2)$$

$$OUT\_B[K] = \Sigma^{k=0:k}((L\_b[k] \cdot S[k]) \cdot \alpha[k] \cdot \Pi^{m=0:k-1}(1-\alpha[m])) \quad (3)$$

The three-dimensional image generated by the projection processing unit 0018 is disposed on the same screen as an arbitrary cross-sectional image by the image combination unit 0017 and is displayed by the display unit 0009.

In the embodiment, the ultrasonic diagnostic device 0001 includes the gradient calculation unit 0019, but may also exclude the gradient calculation unit 0019. In this case, the terms of gradient values S[i] in equations (1) to (3) are excluded from equations (1) to (3) (or are treated as "1.0") so that these terms do not contribute to the three-dimensional image to be generated.

Figure 6:
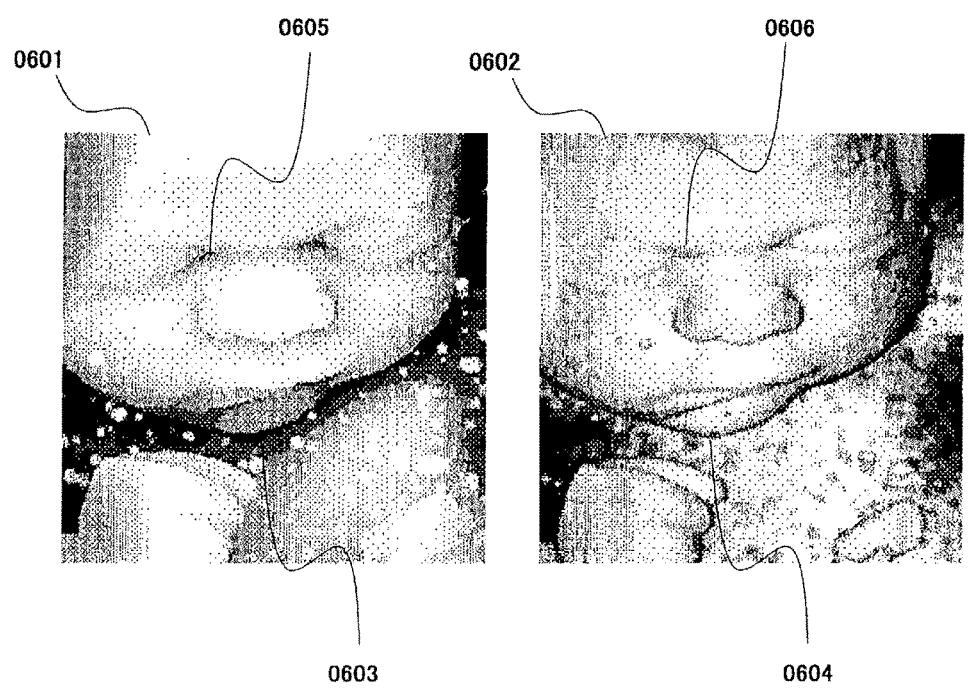
FIG. 6 is a diagram for describing characteristics of a three-dimensional image according to the first embodiment.

Next, the characteristics of the three-dimensional image according to the embodiment will be described with reference to FIG. 6. A three-dimensional image 0601 in FIG. 6 is a three-dimensional image constructed according to a method according to the embodiment. A three-dimensional image 0602 is a three-dimensional image constructed according to a general volume rendering method typified by the Levoy method. As illustrated in FIG. 6, a three-dimensional image 0602 of the related art includes a shade 0604 dark and narrow along the contour of the face of an unborn child. On the other hand, in a three-dimensional image 0601 according to the embodiment, a boundary is clarified by enhancing a shade 0603 in the contour of the face so that the contour floats. In the three-dimensional image 0602 of the related art, a medial ocular angle of the unborn child is shown by a narrow contour line 0606. On the other hand, in the three-dimensional image 0601 according to the embodiment, the medial ocular angle of the unborn child is enhanced and displayed by a shade 0605 so that the boundary is clarified. In this way, by enhancing the shade to clarify the boundary, a natural image of which reality is improved can be obtained in a volume rendering method.

Figure 7:
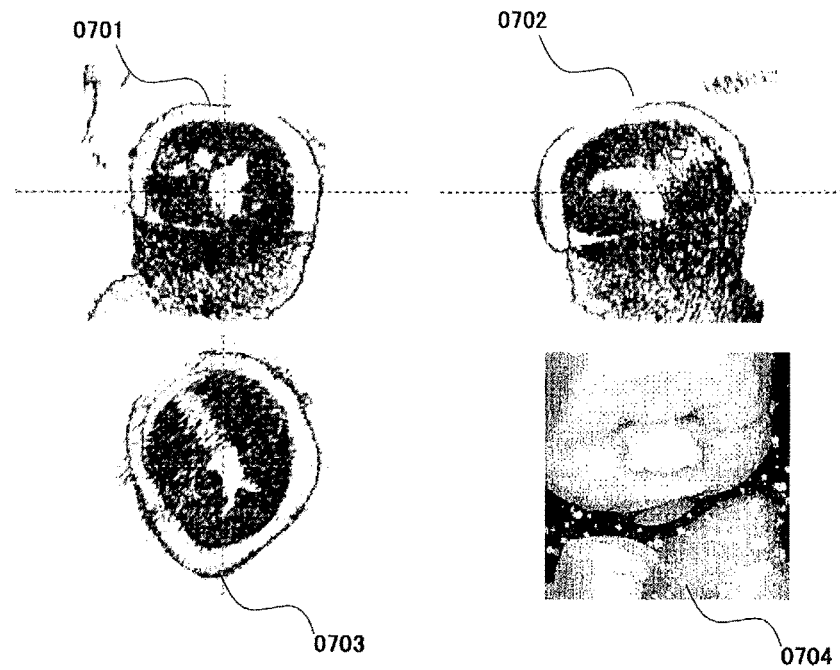
FIG. 7 is a diagram illustrating a display example according to the first embodiment.

FIG. 7 is a diagram illustrating a display example according to the embodiment. As illustrated in FIG. 7, three cross-sectional surfaces 0701, 0702, and 0703 of which planes are orthogonal to each other and a three-dimensional image 0704 are simultaneously displayed. The three-dimensional image generated by the three-dimensional image processing unit 0016 is disposed on the same screen as the three orthogonal cross-sectional surfaces (or arbitrary cross-sectional images) 0701, 0702, and 0703 by the image combination unit 0017 to be displayed by the display unit 0009. By observing the surface by the three-dimensional image with reference to each cross-sectional surface, it is possible to improve inspection precision and efficiency.

In addition to the display format of FIG. 7, an overlapping image of the three-dimensional image 0602 of the related art and the three-dimensional image 0601 according to the embodiment can also be displayed. Three-dimensional images in a plurality of pieces of light source information (light source data), a plurality of pieces of visual line information, and a plurality of positions can also be displayed simultaneously.

The embodiment has been described above, but the present invention is not limited thereto and is alternated and modified within the scope described in the claims.

Figure 8:
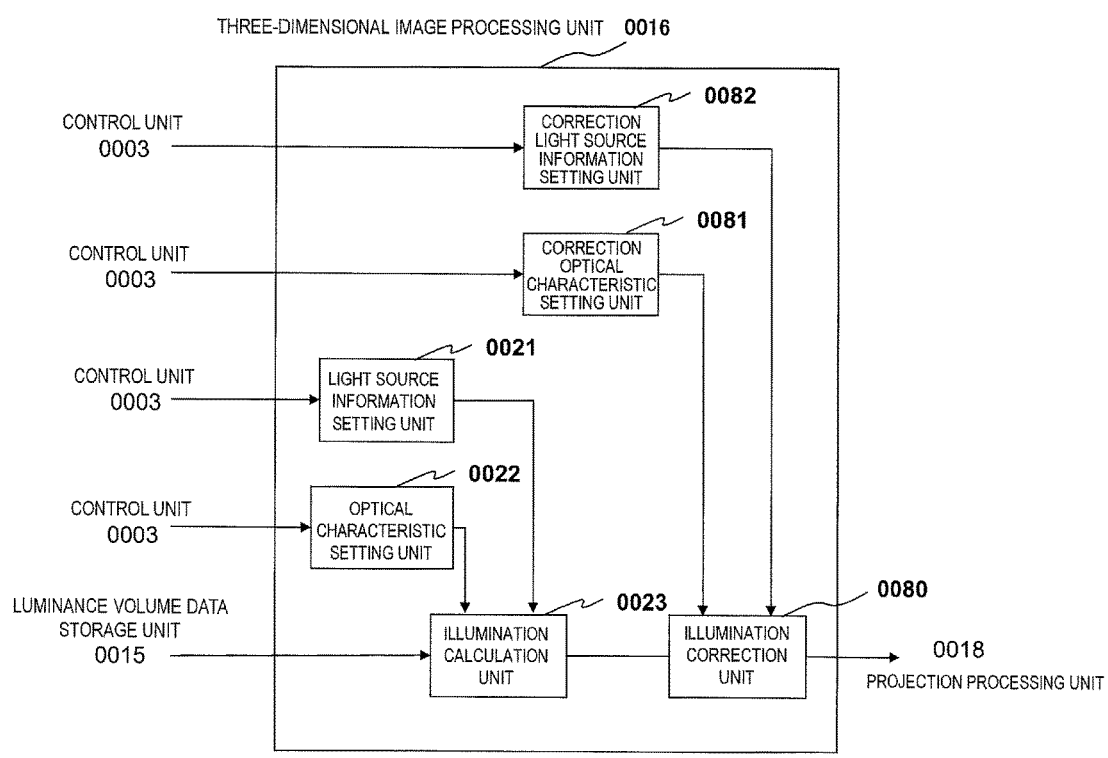
FIG. 8 is a block diagram illustrating a modification example of the three-dimensional image processing unit according to the first embodiment.
Figure 9:
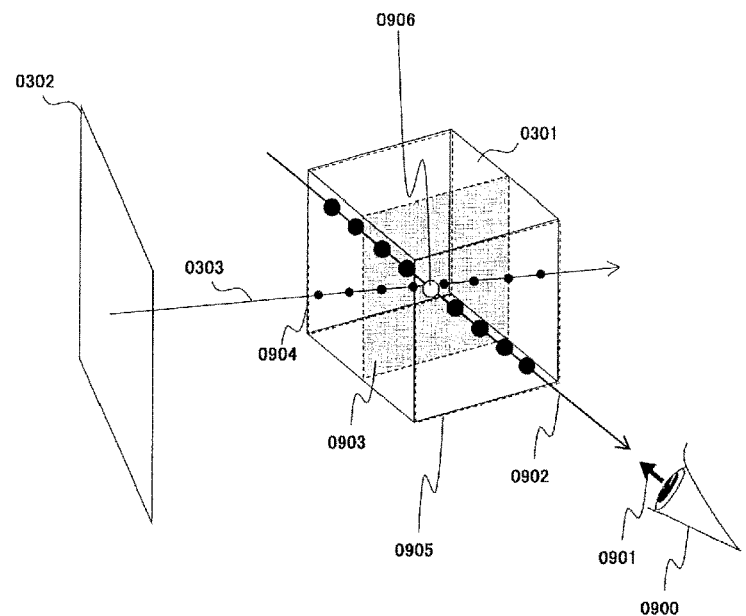
FIG. 9 is a conceptual diagram illustrating illumination calculation according to the modification example of the first embodiment.

FIG. 8 is a block diagram illustrating a modification example of the embodiment. FIG. 9 is a conceptual diagram illustrating illumination calculation according to the modification example of the embodiment. As illustrated in FIG. 8, the ultrasonic diagnostic device 0001 may include an illumination correction unit 0080, a correction optical characteristic setting unit 0081, and a correction light source information setting unit 0082 at the rear stage of the illumination calculation unit 0023. The ultrasonic diagnostic device 0001 according to the embodiment includes the correction light source information setting unit 0082 that sets an opposite direction to a visual line direction in the three-dimensional space as a correction light source direction and sets correction light source data indicating the characteristics of a correction light source radiating light in the correction light source direction, the correction optical characteristic setting unit 0081 that sets a weight coefficient indicating the optical characteristics of the luminance volume data in regard to the correction light source, and the illumination correction unit 0080 that calculates illumination of a position according to the coordinates of the volume data (luminance volume data) based on the correction light source data and the weight coefficient and generates correction illumination volume data based on the calculated correction illumination. The projection processing unit 0018 generates the three-dimensional image from the volume data and the correction illumination volume data.

The illumination volume data by the illumination calculation unit 0023 calculates disposition of the intensity of light in a direction from a proximal position to a distal position of the light source 0302. According to the modification example illustrated in FIGS. 8 and 9, on the other hand, illumination of a result from propagation of light in a direction from the distal position to the proximal position in a visual line direction 0901 of the observer can be added to illumination observed from a viewpoint 0900 of an observer.

The correction light source information setting unit 0082 sets a correction light source on the opposite side to the viewpoint 0900 and sets a correction light source direction 0902 in the opposite direction to the visual line direction 0901. That is, the correction light source information setting unit 0082 sets the opposite direction to the visual line direction 0901 in a three-dimensional space as the correction light source direction 0902 and sets the correction light source data indicating the characteristics of the correction light source radiating light in the correction light source direction 0902.

The correction optical characteristic setting unit 0081 sets the weight coefficient in the opposite direction (the correction light source direction 0902) to the visual line direction 0901. That is, the correction optical characteristic setting unit 0081 sets the weight coefficient indicating the optical characteristics of the luminance volume data in regard to the correction light source.

The illumination correction unit 0080 performs illumination correction calculation to generate correction illumination volume data corrected from the illumination volume data in the direction from the distal position to the proximal position of the visual line direction. That is, the illumination correction unit 0080 calculates the illumination of the position according to the coordinates of the luminance volume data based on the correction light source data and the weight coefficient and generates the correction illumination volume data based on the calculated correction illumination.

As illustrated in FIG. 9, the light source 0302 and the light source direction 0303 are set in the luminance volume data 0301, as in FIG. 3. When the illumination volume data is generated and the visual line direction 0901 is set, the correction light source information setting unit 0082 sets the correction light source on the opposite side to the viewpoint 0900 and sets the correction light source direction 0902 in the opposite direction to the visual line direction.

A plane 0904 indicates a position of a plane in which the luminance volume data 0301 first intersects (comes into contact with) an orthogonal plane in the correction light source direction 0902, is a plane including the first voxel on the correction light source direction 0902, and indicates an illumination calculation start position. A plane 0905 indicates a position of a plane in which the luminance volume data 0301 finally intersects (comes into contact with) an orthogonal plane in the correction light source direction 0902, is a plane including the final voxel on the correction light source direction 0902, and indicates an illumination calculation end position.

The illumination correction unit 0080 performs illumination correction on the plane orthogonal in the correction light source direction 0902. As illustrated in FIG. 9, the illumination correction unit 0080 performs the illumination correction in a scope from the plane 0904 to the plane 0905 and performs, for example, illumination correction calculation on the plane 0903 in illumination correction of a sample 0906 located at the correction light source direction 0902.

Figure 10:
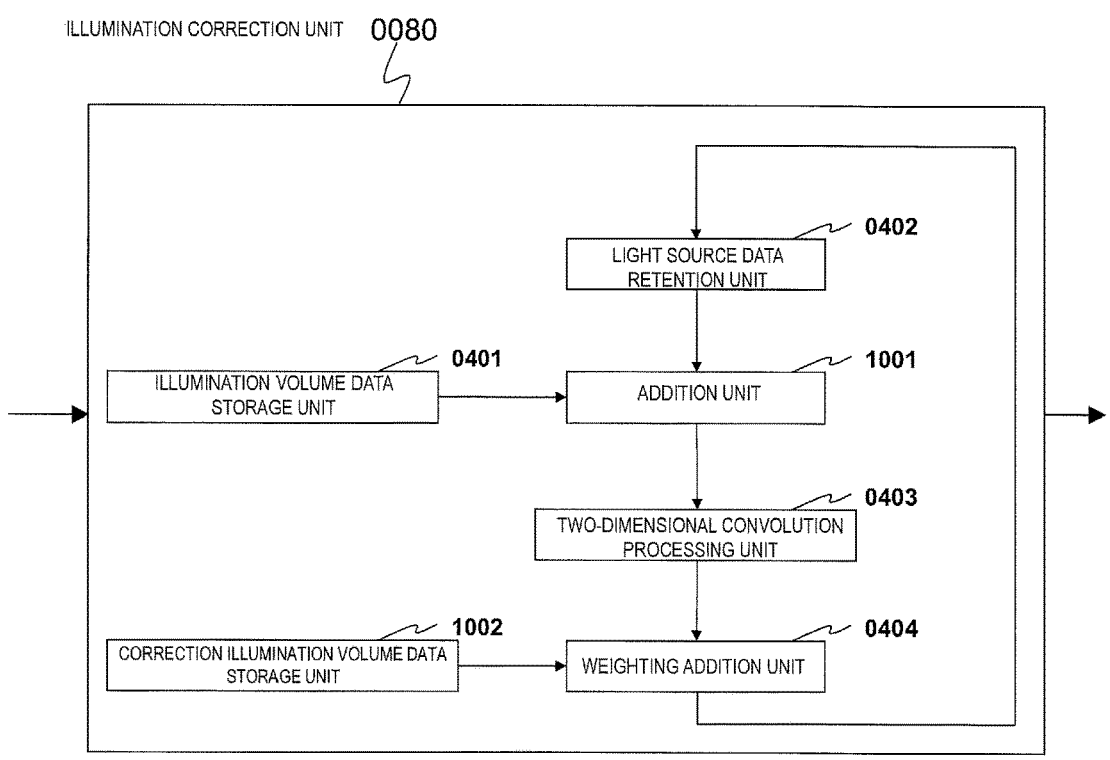
FIG. 10 is a block diagram illustrating an example of an illumination correction unit.

Next, the configuration of the illumination correction unit 0080 will be described with reference to FIG. 10. As illustrated in FIG. 10, the illumination correction unit 0080 includes an addition unit 1001, a correction illumination volume data storage unit 1002, an illumination volume data storage unit 0401, a light source data retention unit 0402, a two-dimensional convolution processing unit 0403, and a weighting addition unit 0404. The constituent elements denoted by the same numbers in FIGS. 4 and 10 have the same functions unless mentioned otherwise.

The illumination correction unit 0080 includes the addition unit 1001 that adds the correction light source data and the illumination volume data, the two-dimensional convolution processing unit 0403 that generates two-dimensional convolution integrated data by performing two-dimensional convolution integration on an added value of the correction light source data and the illumination volume data, and a weighting addition unit 0404 that generates the correction illumination volume data by performing weighting addition on the correction light source data and the two-dimensional convolution integrated data based on the weight coefficient.

The illumination correction unit 0080 reads the output illumination data at the coordinates of the input light source data (correction light source data) stored in the light source data retention unit 0402 from the illumination volume data storage unit 0401 and adds the output illumination data to the input light source data (correction light source data). That is, the addition unit 1001 adds the correction light source data and the illumination volume data. However, since the light source data retention unit 0402 of the illumination correction unit 0080 has no initial value, the light source data retention unit 0402 differs from the light source data retention unit 0402 of the illumination calculation unit 0023.

In the illumination correction unit 0080, the addition unit 1001 adds the input light source data stored in the light source data retention unit 0402 and the output illumination data at the coordinates of the input light source data read from the illumination volume data storage unit 0401, and then updates and stores the input light source data.

The two-dimensional convolution processing unit 0403 performs two-dimensional convolution integration on the input light source data retained in the addition unit 1001. That is, the two-dimensional convolution processing unit 0403 generates two-dimensional convolution integrated data by performing two-dimensional convolution integration on the added value of the correction light source data and the illumination volume data stored in the illumination volume data storage unit 0401.

The weighting addition unit 0404 inputs the two-dimensional convolution integrated data which is an output result of the two-dimensional convolution processing unit 0403 and inputs the updated input light source data retained by the addition unit 1001. The weighting addition unit 0404 performs weighing addition on the output result of the two-dimensional convolution processing unit 0403 and the updated input light source data retained by the addition unit 1001. That is, the weighting addition unit 0404 generates the correction illumination volume data by performing the weighting addition on the correction light source data and the two-dimensional convolution integrated data based on the weight coefficient. Here, the weight coefficient used by the weighting addition unit 0404 is set by the correction optical characteristic setting unit 0081 set for the correction. As described above, the weight coefficient may be referred to in the two-dimensional table in which the luminance value of the luminance volume data and the distance from a body surface (or the surface of a tissue) are expressed as two indexes two-dimensionally.

The correction illumination volume data storage unit 1002 stores the result of the weighting addition unit 0404 along with positional information according to the voxel coordinates. The result of the weighting addition unit 0404 is input to the light source data retention unit 0402 and is stored (retained) as the input light source data.

According to the modification example illustrated in FIGS. 8 to 10, the illumination of the result from propagation of light in the direction from the distal position to the proximal position in the visual line direction 0901 of the observer can be added to the illumination observed from the viewpoint 0900 of the observer, and the correction illumination volume data in which the illumination in two directions, the light source directions 0303 and the correction light source direction 0902, is calculated can be generated. The correction illumination volume data storage unit 1002 is configured to be independent from the illumination volume data storage unit 0401, but a common memory region may be used.

When the reality of the correction illumination volume data generated by the illumination correction unit 0080 is further improved as in the above-described embodiment, the illumination calculation (or the illumination correction calculation) may be performed for each wavelength of the light source. In this case, as in the embodiment, the illumination calculation (or the illumination correction calculation) is repeatedly performed for each of the set wavelengths, and thus the correction illumination volume data of each of the set wavelengths is generated. For example, when the light source 0302 is the three primary colors of additive color mixture, the illumination correction unit 0080 sets three sets of weight coefficients (or three kinds of two-dimensional weight coefficient tables) corresponding to the wavelengths of the R, G, and B components and generates three kinds of pieces of correction illumination volume data. Then, the projection processing unit 0018 generates a three-dimensional image from the three kinds of pieces of correction illumination volume data generated by the illumination correction unit 0080 and the luminance volume data stored in the luminance volume data storage unit 0015. That is, the projection processing unit 0018 generates the three-dimensional image from the luminance volume data and the correction illumination volume data.

In this way, by calculating the illumination in the two directions, the light source direction 0303 and the correction light source direction 0902, the illumination based on the more natural shade can be calculated, and thus the three-dimensional image of which reality is improved can be generated in a volume rendering method.

Figure 11:
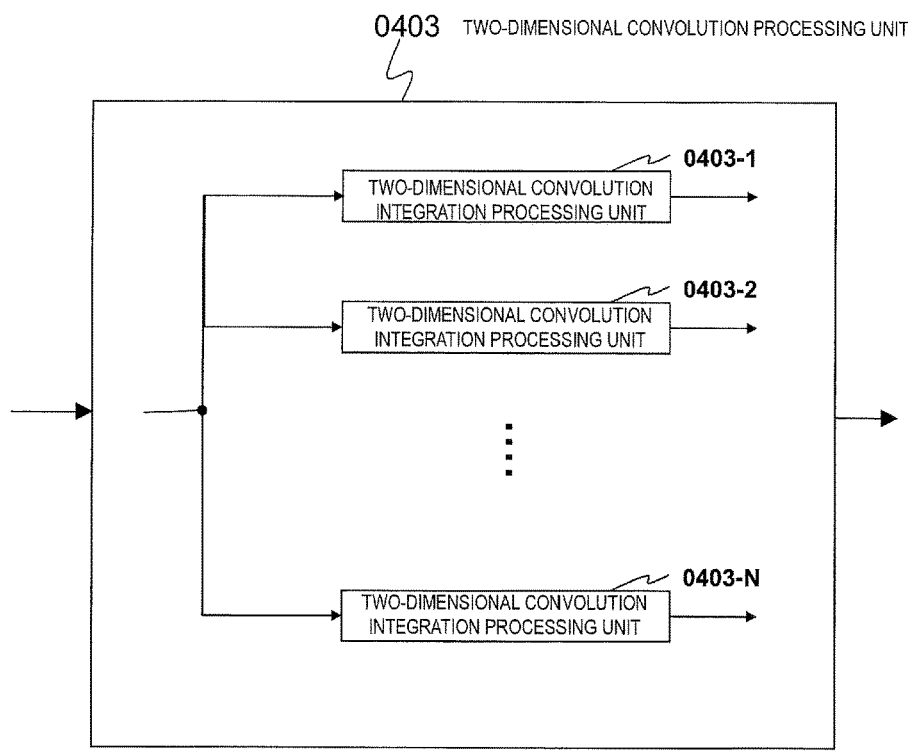
FIG. 11 is a block diagram illustrating a two-dimensional convolution processing unit according to another modification example of the first embodiment.

Another modification example will be described with reference to FIG. 11. As illustrated in FIG. 11, according to another modification example, the two-dimensional convolution processing unit 0403 has a characteristic structure. Accordingly, the two-dimensional convolution processing unit 0403 will be mainly described.

As illustrated in FIG. 11, the two-dimensional convolution processing unit 0403 reads the input light source data from the light source data retention unit 0402 in the illumination calculation unit 0023, performs a two-dimensional convolution integration process, and outputs the two-dimensional convolution integrated data to the weighting addition unit 0404. The two-dimensional convolution processing unit 0403 generates two or more, that is, a plurality of pieces of two-dimensional convolution integrated data. That is, the two-dimensional convolution processing unit 0403 generates the plurality of pieces of two-dimensional convolution integrated data by performing two-dimensional convolution integration on the light source data a plurality of times.

The weighting addition unit 0404 generates the output illumination data by performing the weight addition process on the input light source data read from the light source data retention unit 0402 and the plurality of pieces of two-dimensional convolution integrated data generated by the two-dimensional convolution processing unit 0403 and stores the output illumination data at the voxel coordinates of the illumination volume data storage unit 0401.

The configuration of the two-dimensional convolution processing unit 0403 illustrated in FIG. 11 will be described. The two-dimensional convolution processing unit 0403 includes two or more, that is, a plurality of two-dimensional convolution processing units. The two-dimensional convolution processing units 0403-1 to 0403-N output different pieces of two-dimensional convolution integrated data in regard to the input light source data and each output the two-dimensional convolution integrated data to the weighting addition unit 0404. In this case, for the weight coefficients in the weighting addition unit 0404, coefficients for the input light source data and the plurality of two-dimensional convolution integrated data generated by the two-dimensional convolution processing units 0403 (0403-1 to 0403-N) are retained. The different weight coefficient for each of the output results of the respective two-dimensional convolution processing units 0403 (0403-1 to 0403-N) may be referred to in the two-dimensional table and may be used by the weighting addition unit 0404.

In this way, the ultrasonic diagnostic device 0001 includes the plurality of two-dimensional convolution processing units 0403-1 to 0403-N, and thus can express a plurality of shade effects according to a behavior of light. Thus, in a volume rendering method, the three-dimensional image in which the illumination based on a behavior (for example, diffusion) of more natural light is calculated can be generated.

Figure 12:
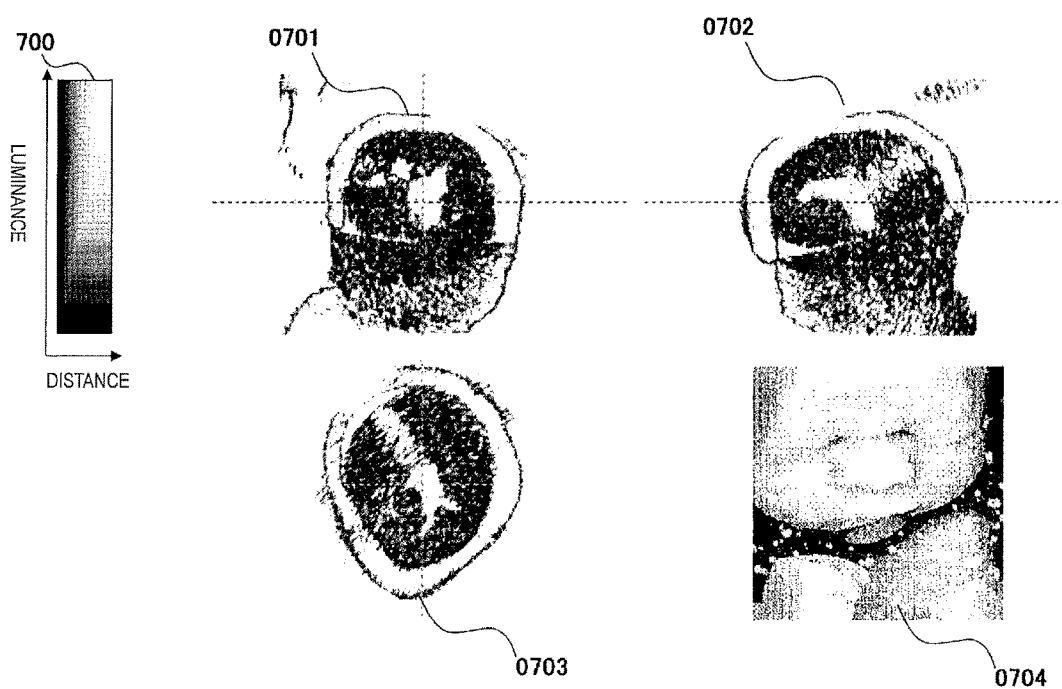
FIG. 12 is a diagram illustrating a color map displayed by a display unit.

The display unit 0009 may display a color map showing a color tone which can be obtained according to the luminance and the distance from a body surface. That is, the display unit 0009 displays a color map in which a voxel value (luminance) of volume data (luminance volume data) and a distance from the surface of a target object are set as indexes according to a two-dimensional weight coefficient table regulating the weight coefficient. FIG. 12 is a diagram illustrating a color map in a display example according to the embodiment. As illustrated in FIG. 12, three cross-sectional surfaces 0701 to 0703 orthogonal to each other and a three-dimensional image 0704 are displayed simultaneously, as in FIG. 7. Further, a color map 700 is displayed. The color map 700 is a pseudo color map for visually recognizing a color tone of a three-dimensional image realized by the two-dimensional weight coefficient table 0501.

In the color map 700, a luminance voxel value is disposed on the vertical axis. In the color map 700, as described with reference to FIGS. 4 and 5, the number of repetitions (corresponding to the distance from the surface of a tissue) of the illumination calculation performed based on the two-dimensional weight coefficient table 0501 according to the distance from the surface of a tissue is disposed on the horizontal axis. In this way, the color map 700 is a reference image indicating the color tone which can be obtained by the luminance and the distance from a body surface.

An operator can recognize which color tone can be assigned to the three-dimensional image (illumination three-dimensional image) 0704 by confirming the color map 700. For example, the operator can recognize whether a displayed region is a bone or a soft tissue. The direction of the axis of the color map 700 can also be transposed or the axis can also be reversed.

Figure 13:
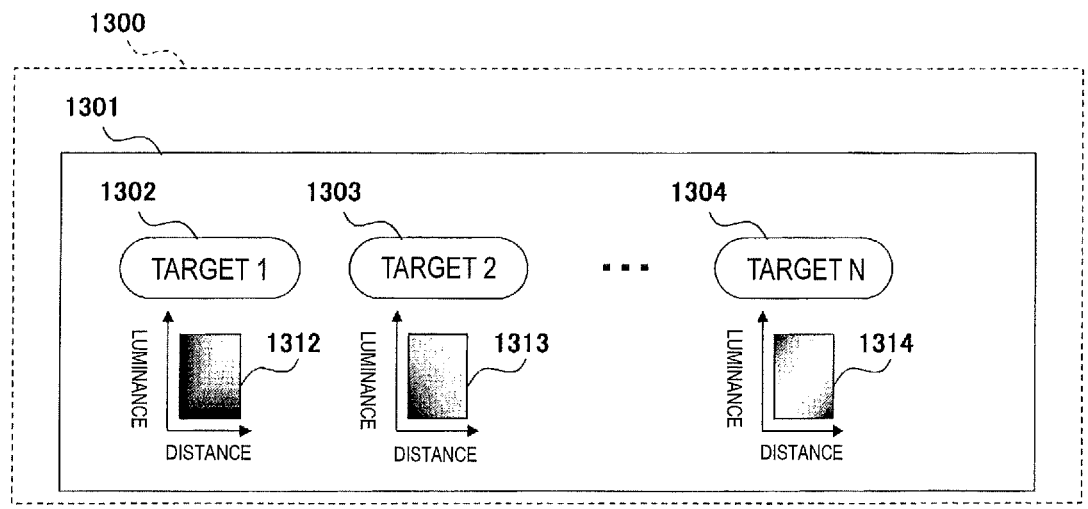
FIG. 13 is a diagram illustrating an example of a method of selecting a color map.

The color map 700 may also be selected from among a plurality of color maps. For example, the display unit 0009 may selectively display a plurality of color maps corresponding to the plurality of two-dimensional weight coefficient tables regulating the weight coefficients according to a tissue of a target object (a facial region, a bony region, or the like of an unborn child). FIG. 13 is a diagram illustrating a method of selecting the color map 700. As illustrated in FIG. 13, the color map 700 can be selected by operating a graphical interface 1300 for selecting a region displayed on the display unit 0009 by the operation unit 0004 (a pointer, a track ball, an encoder, and the like).

A selection screen 1301 in FIG. 13 is an example of buttons displayed at the time of inspection and a button according to a target can be selected. For example, by selecting the button according to the target from among a button 1302 for target 1, a button 1303 for target 2, . . . , and a button 1304 for target N, the three-dimensional image according to the target can be generated.

When the button 1302 for target 1 designates the face of an unborn child and the button 1302 for target 1 is selected, a proper weight coefficient (the two-dimensional weight coefficient table 0501) to the face of the unborn child is selected and set in the optical characteristic setting unit 0022 or the correction optical characteristic setting unit 0081, and thus a color map 1312 corresponding to the button 1302 for target 1 is displayed.

When the button 1303 for target 2 designates a bone of an unborn child and the button 1303 for target 2 is selected, a proper weight coefficient (the two-dimensional weight coefficient table 0501) to a bony region is selected and set in the optical characteristic setting unit 0022 or the correction optical characteristic setting unit 0081, and thus a color map 1313 corresponding to the button 1303 for target is displayed. The graphical interface 1300 for region selection can also display the selected color maps 1312 to 1314.

The color maps 1312 to 1314 are color maps generated based on the two-dimensional weight coefficient table 0501 selected by the target buttons 1302 to 1304, respectively. By simultaneously displaying the target buttons 1302 to 1304, the operator can select a proper color map without hesitation.

Figure 14:
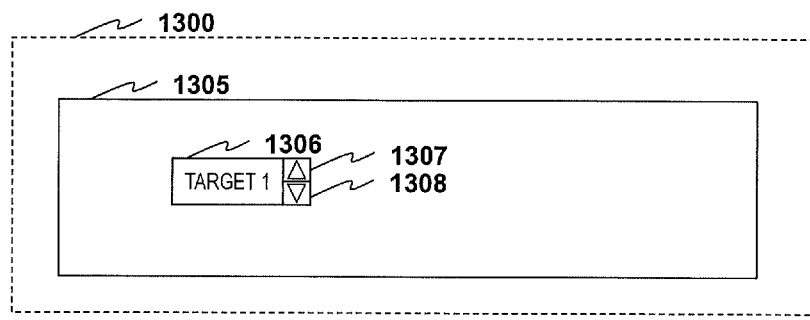
FIG. 14 is a diagram illustrating another example of the method of selecting a color map.

As illustrated in FIG. 14, a selection screen 1305 may be displayed in the graphical interface 1300 for region selection. The selection screen 1305 is an example in which a button displayed at the time of inspection is different and includes a target display region 1306 displaying the name of a selected target, an up target selection button 1307, and a down target selection button 1308. A plurality of targets prepared in advance can be switched using the up target selection button 1307 and the down target selection button 1308. Accordingly, the operator can generate a three-dimensional image according to a target by operating the up target selection button 1307 or the down target selection button 1308. For example, when target 1 (button for target 1) designates the face of the unborn child and target 2 (button for target 2) designates a bone of the unborn child, the target is switched sequentially by the up target selection button 1307 or the down target selection button 1308. In this case, when target 1 (button for target 1) is selected, a proper weight coefficient for the face of the unborn child is selected and set in the optical characteristic setting unit 0022 or the correction optical characteristic setting unit 0081, and thus the color map 700 is switched. Next, when target 2 (button for target 2) is selected by the down target selection button 1308, a proper weight coefficient for a bony region is selected and set in the optical characteristic setting unit 0022 or the correction optical characteristic setting unit 0081, and thus the color map 700 is switched.

The input light source data can also be switched in accordance with a target and the input light source data according to the target can also be set in the light source information setting unit 0021. A target selection screen can be prepared for the weight coefficient and the input light source data and can also be selected (or controlled) independently from the weight coefficient and the input light source data.

Second Embodiment

Hereinafter, the ultrasonic diagnostic device 0001 according to a second embodiment of the present invention will be described with reference to the drawings. The ultrasonic diagnostic device 0001 generates a three-dimensional image of which reality is improved by expressing a behavior of light in a tissue and expressing interaction of the light between tissues with different natures. When the tissues with different natures are adjacent, a behavior of light has a mutual influence on the adjacent tissues by interaction of light and an influence occurs in decoloring or the like. For example, when a blood vessel is present between a light source and a muscular or fat tissue (a blood vessel and a muscular or fat tissue are adjacent back and forth in a light source direction), the muscular or fat tissue colors red by passing light the blood vessel despite the fact that the color of the muscular or fat tissue is not red. Even when a blood vessel and a muscular or fat tissue are adjacent back and forth in a light source direction, diffusion of light occurs by interaction of the light in the blood vessel and the muscular or fat tissue and the muscular or fat tissue colors red. In this way, the ultrasonic diagnostic device 0001 generates a three-dimensional image of which reality is improved by expressing the interaction of the light between tissues with different natures (for example, tissues of a blood vessel and a muscular or fat tissue).

Figure 15:
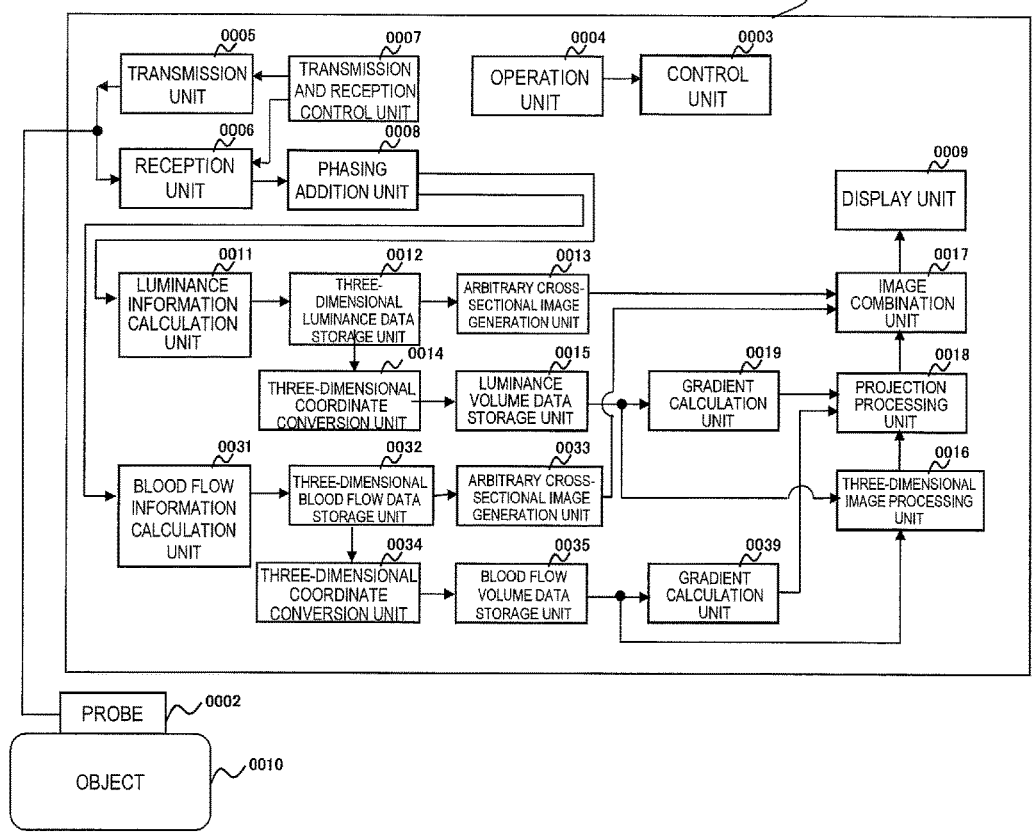
FIG. 15 is a block diagram illustrating an example of an ultrasonic diagnostic device according to a second embodiment.

FIG. 15 is a block diagram illustrating an example of the ultrasonic diagnostic device 0001 according to the embodiment. As illustrated in FIG. 15, the ultrasonic diagnostic device 0001 includes a control unit 0003, an operation unit 0004, a transmission unit 0005, a reception unit 0006, a transmission and reception control unit 0007, a phasing addition unit 0008, a display unit 0009, a luminance information calculation unit 0011, a three-dimensional luminance data storage unit 0012, an arbitrary cross-sectional image generation unit 0013, a three-dimensional coordinate conversion unit 0014, a luminance volume data storage unit 0015, a three-dimensional image processing unit 0016, an image combination unit 0017, a projection processing unit 0018, and a gradient calculation unit 0019.

The ultrasonic diagnostic device 0001 includes a blood flow information calculation unit 0031, a three-dimensional blood flow data storage unit 0032, an arbitrary cross-sectional image generation unit 0033, a three-dimensional coordinate conversion unit 0034, a blood flow volume data storage unit 0035, and a gradient calculation unit 0039. The ultrasonic diagnostic device 0001 displays a three-dimensional image of a target object based on luminance volume data and blood flow volume data (including blood flow rate volume data, blood flow amplitude volume data, and blood flow dispersion volume data). The blood flow dispersion volume data includes blood flow rate dispersion volume data and blood flow amplitude dispersion volume data. An ultrasonic probe 0002 is connected to the ultrasonic diagnostic device 0001.

The ultrasonic probe 0002 is brought into contact with the object 0010 for use. The ultrasonic probe 0002 is formed such that a plurality of vibrators are arranged and has a function of transmitting and receiving ultrasonic waves via the vibrators to and from the object 0010. The ultrasonic probe 0002 is configured to include the plurality of vibrators formed in a one-dimensional straight-line shape or linear shape, and can electrically transmit and receive ultrasonic waves in the arrangement direction of the probe and simultaneously transmit and receive ultrasonic waves three-dimensionally by mechanically vibrating or manually moving the vibrators in a direction perpendicular to the arrangement direction of the plurality of vibrators. The ultrasonic probe 0002 may be configured such that the plurality of vibrators are arranged two-dimensionally and can electrically control transmission and reception of ultrasonic waves.

The control unit 0003 controls each constituent element of the ultrasonic diagnostic device 0001 and the ultrasonic probe 0002. The operation unit 0004 performs various inputs to the control unit 0003. The operation unit 0004 includes a keyboard or a track ball.

The transmission unit 0005 repeatedly transmits ultrasonic waves to the object 0010 via the ultrasonic probe 0002 at constant time intervals. The transmission unit 0005 drives the vibrators of the ultrasonic probe 0002 to generate transmission wave pulses for generating ultrasonic waves. The transmission unit 0005 has a function of setting a convergent point of the ultrasonic waves to be transmitted at a certain depth. The reception unit 0006 receives reflected echo signals reflected from the object 0010. The reception unit 0006 amplifies the reflected echo signals received by the ultrasonic probe 0002 at a predetermined gain to generate RF signals, that is, received signals. The transmission and reception control unit 0007 controls the transmission unit 0005 and the reception unit 0006.

The phasing addition unit 0008 performs phasing addition on the reflected echo signals received by the reception unit 0006. The phasing addition unit 0008 controls the phases of the RF signals amplified by the reception unit 0006 to form ultrasonic beams at one convergent point or a plurality of convergent points and generates RF signal frame data (corresponding to RAW data). The luminance information calculation unit 0011 constructs a luminance tomographic image based on the RF signal frame data generated by the phasing addition unit 0008. The three-dimensional luminance data storage unit 0012 stores a plurality of luminance tomographic images formed by the luminance information calculation unit 0011. The arbitrary cross-sectional image generation unit 0013 generates an arbitrary cross-sectional image based on the acquired shape of the luminance tomographic image. The three-dimensional coordinate conversion unit 0014 performs three-dimensional coordinate conversion based on the acquired shape of the luminance tomographic image to generate luminance volume data and stores the luminance volume data in the luminance volume data storage unit 0015.

The blood flow information calculation unit 0031 constructs blood flow tomographic images based on the RF signal frame data generated by the phasing addition unit 0008. The three-dimensional blood flow data storage unit 0032 stores the plurality of blood flow tomographic images constructed by the blood flow information calculation unit 0031. The arbitrary cross-sectional image generation unit 0033 generates arbitrary cross-sectional images based on the acquired shapes of the blood flow tomographic images. The three-dimensional coordinate conversion unit 0034 performs three-dimensional coordinate conversion based on the acquired shapes of the blood flow tomographic images to generate blood flow volume data (including blood flow rate volume data, blood flow amplitude volume data, and blood flow dispersion volume data) and stores the blood flow volume data in the blood flow volume data storage unit 0035.

The three-dimensional image processing unit 0016 generates illumination volume data using the luminance volume data stored in the luminance volume data storage unit 0015 and the blood flow volume data stored in the blood flow volume data storage unit 0035.

The gradient calculation unit 0019 generates luminance gradient volume data using the luminance volume data stored in the luminance volume data storage unit 0015. The gradient calculation unit 0039 generates blood flow gradient volume data using the blood flow volume data stored in the blood flow volume data storage unit 0035. A gradient value of the gradient volume data (the blood flow gradient volume data) is a value indicating a slope (for example, a slope of a normal line in a three-dimensional shape or an angle between of the normal line in the three-dimensional shape and a visual line direction) of a three-dimensional shape calculated based on a luminance value.

The projection processing unit 0018 generates a three-dimensional image by performing a rendering process using the illumination volume data, the luminance volume data, and the luminance gradient volume data. The projection processing unit 0018 generates a three-dimensional image by performing a rendering process using the luminance volume data, the blood flow volume data, and the blood flow gradient volume data. The projection processing unit 0018 selects luminance or blood flow for each voxel. When the luminance is selected, the rendering calculation is performed on the voxel using the illumination volume data, the luminance volume data, and the luminance gradient volume data. When the blood flow is selected, the rendering calculation is performed on the voxel using the illumination volume data, the blood flow volume data, and the blood flow gradient volume data. The projection processing unit 0018 generates a three-dimensional image by integrating the results of the rendering calculation on the voxels in accordance with the luminance or the blood flow into the entire volume.

The image combination unit 0017 combines the three-dimensional image generated by the projection processing unit 0018, the arbitrary cross-sectional image of three-dimensional luminance data generated by the arbitrary cross-sectional image generation unit 0013, and the arbitrary cross-sectional image of the three-dimensional blood flow data generated by the arbitrary cross-sectional image generation unit 0033. The display unit 0009 displays a display image generated by the image combination unit 0017.

Next, a process for the three-dimensional luminance data and the three-dimensional blood flow data will be described. The ultrasonic probe 0002 can transmit and receive the ultrasonic waves and can perform measurement along two axes of, for example, $\theta$ and $\phi$ while switching transmission and reception directions two-dimensionally. The luminance information calculation unit 0011 constructs two-dimensional luminance data by inputting the RF signal frame data output from the phasing addition unit 0008 based on a setting condition in the control unit 0003 and performing signal processing such as gain correction, log compression, detection, contour enhancement, and a smoothing process. The blood flow information calculation unit 0031 constructs two-dimensional blood flow data by inputting the RF signal frame data output from the phasing addition unit 0008 based on a setting condition in the control unit 0003 and performing processes such as blood flow rate estimation, blood flow amplitude estimation, blood flow dispersion estimation (including blood flow rate dispersion estimation and blood flow amplitude dispersion estimation), contour enhancement, noise removal, and a smoothing process. The two-dimensional blood flow data may be constructed by at least one of a blood flow rate, a blood flow amplitude, and blood flow rate dispersion.

The three-dimensional luminance data storage unit 0012 has a function of storing a plurality of pieces of two-dimensional luminance data, which is output data of the luminance information calculation unit 0011, in transmission and reception directions corresponding to acquisition positions. For example, a plurality of pieces of two-dimensional luminance data obtained by driving and acquiring two-dimensional luminance tomographic images, generated from measurement results when time-series ultrasonic data sampled in a depth direction is transmitted and received in a $\theta$ direction, in a $\phi$ direction orthogonal to the $\theta$ direction in association with $\phi$ are stored as three-dimensional luminance data.

The three-dimensional blood flow data storage unit 0032 has a function of storing a plurality of pieces of two-dimensional blood flow data which is output data of the blood flow information calculation unit 0031 based on transmission and reception directions corresponding to acquisition positions. For example, a plurality of pieces of two-dimensional blood flow data obtained by driving and acquiring two-dimensional blood flow tomographic images, generated from measurement results when time-series ultrasonic data sampled in the depth direction is transmitted and received in the θ direction, in the φ direction orthogonal to the θ direction in association with φ are stored as three-dimensional blood flow data.

The three-dimensional coordinate conversion unit 0014 performs three-dimensional coordinate conversion on coordinates in a space based on the acquisition positions (depth, θ, φ) using the three-dimensional luminance data stored in the three-dimensional luminance data storage unit 0012, generates luminance volume data, and stores the luminance volume data in the luminance volume data storage unit 0015.

The three-dimensional coordinate conversion unit 0034 performs three-dimensional coordinate conversion on coordinates in a space based on the acquisition positions (depth, θ, φ) using the three-dimensional blood flow data stored in the three-dimensional blood flow data storage unit 0032, generates blood flow volume data, and stores the blood flow volume data in the blood flow volume data storage unit 0035.

The arbitrary cross-sectional image generation unit 0013 generates an arbitrary cross-sectional image of the three-dimensional luminance data on an arbitrary plane in a three-dimensional space set by the control unit 0003 and the operation unit 0004 based on the acquisition positions (depth, θ, φ) using the three-dimensional luminance data stored in the three-dimensional luminance data storage unit 0012.

The arbitrary cross-sectional image generation unit 0033 generates an arbitrary cross-sectional image of the three-dimensional blood flow data on an arbitrary plane in a three-dimensional space set by the control unit 0003 and the operation unit 0004 based on the acquisition positions (depth, θ, φ) using the three-dimensional blood flow data stored in the three-dimensional blood flow data storage unit 0032.

The gradient calculation unit 0019 generates volume data in which a gradient in a visual line direction at respective voxel coordinates is calculated based on the luminance volume data stored in the luminance volume data storage unit 0015.

The gradient calculation unit 0039 generates volume data in which a gradient in a visual line direction at respective voxel coordinates is calculated based on the blood flow volume data stored in the blood flow volume data storage unit 0035.

Next, a process of the three-dimensional image processing unit 0016 will be described. The three-dimensional image processing unit 0016 is a characteristic processing unit of the ultrasonic diagnostic device 0001 according to the embodiment and generates illumination volume data based on a light source in the three-dimensional space set by the control unit 0003 and the operation unit 0004, using the luminance volume data stored in the luminance volume data storage unit 0015 and the blood flow volume data stored in the blood flow volume data storage unit 0035.

Figure 16:
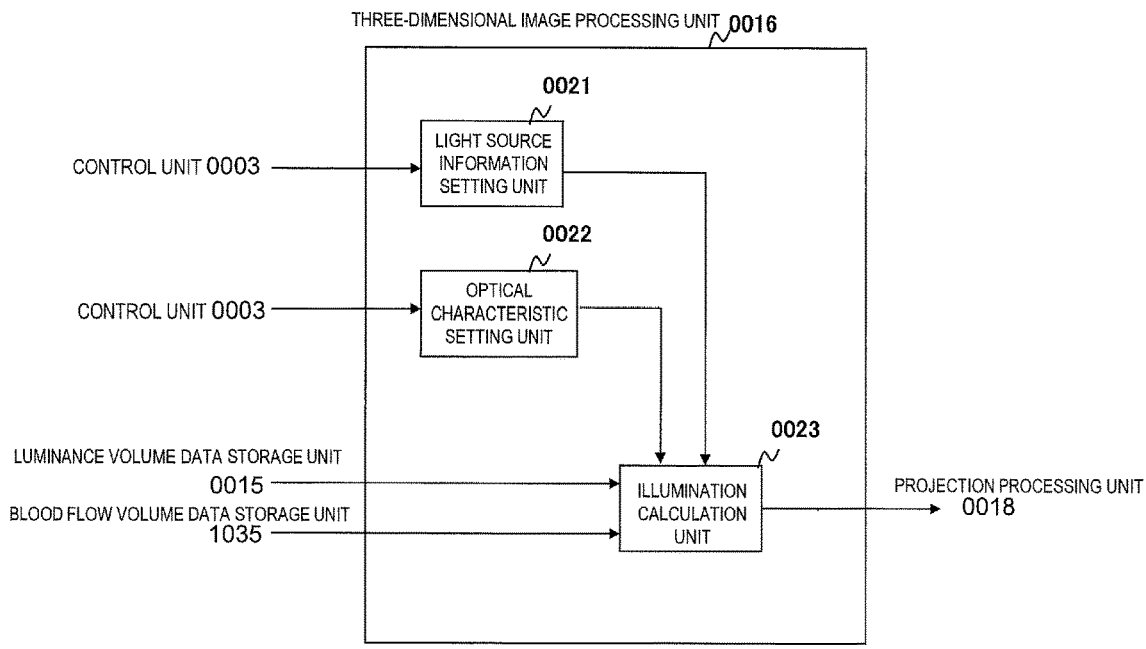
FIG. 16 is a block diagram illustrating an example of a three-dimensional image processing unit according to the second embodiment.

FIG. 16 is a block diagram illustrating an example of the three-dimensional image processing unit 0016. As illustrated in FIG. 16, the three-dimensional image processing unit 0016 includes a light source information setting unit 0021, an optical characteristic setting unit 0022, and an illumination calculation unit 0023.

The ultrasonic diagnostic device 0001 according to the embodiment is the ultrasonic diagnostic device 0001 that displays a three-dimensional image of a target object based on the luminance volume data and the blood flow volume data. The ultrasonic diagnostic device 0001 includes the light source information setting unit 0021 that sets light source data indicating the characteristics of a light source set in a three-dimensional space, the optical characteristic setting unit 0022 that sets a weight coefficient indicating optical characteristics of the luminance volume data and a weight coefficient indicating optical characteristics of the blood flow volume data in regard to the light source, the illumination calculation unit 0023 that calculates at least one of illumination of a position according to coordinates of the luminance volume data and illumination of a position according to coordinates of the blood flow volume data based on the light source data and the weight coefficients and generates illumination volume data based on the calculated illumination, and the projection processing unit 0018 that generates the three-dimensional image from at least one of the luminance volume data and the blood flow volume data and the illumination volume data.

A method of generating an ultrasonic three-dimensional image according to the embodiment is an ultrasonic wave three-dimensional image generation method of displaying a three-dimensional image of a target object based on the luminance volume data and the blood flow volume data. The method includes setting light source data indicating characteristics of a light source set in a three-dimensional space, setting a weight coefficient indicating optical characteristics of the luminance volume data and a weigh coefficient indicating the optical characteristics of the blood flow volume data in regard to the light source, calculating at least one of illumination of a position according to coordinates of the luminance volume data and illumination of a position according to coordinates of the blood flow volume data based on the light source data and the weight coefficients, generating illumination volume data based on the calculated illumination, and generating the three-dimensional image from at least one of the luminance volume data and the blood flow volume data and the illumination volume data.

The light source information setting unit 0021 sets (generates) light source data indicating the characteristics of the light source set in the three-dimensional space of the three-dimensional image. For example, the light source information setting unit 0021 sets light source data indicating strength of the light source. The light source information setting unit 0021 can also adjust at least one of the strength of the light source, a position of the light source in the three-dimensional space, a direction of the light source, color tone of the light source, and a shape of the light source to set the light source data. The optical characteristic setting unit 0022 sets the optical characteristics of the luminance volume data and the blood flow volume data set by the control unit 0003 and the operation unit 0004. The optical characteristic setting unit 0022 sets weight coefficients indicating the optical characteristics of the luminance volume data and the blood flow volume data in regard to the light source. The illumination calculation unit 0023 calculates illumination corresponding to the coordinates of voxels on the output illumination volume data using at least one of the luminance volume data and the blood flow volume data based on the light source data set by the light source information setting unit 0021 and the optical characteristics set by the optical characteristic setting unit 0022 and generates illumination volume data.

That is, the illumination calculation unit 0023 calculates the illumination based on the light source data, the weight coefficients, and the volume data (the luminance volume data or the blood flow volume data) and generates the illumination volume data based on the calculated illumination.

Next, light source information set by the light source information setting unit 0021, optical characteristics set by the optical characteristic setting unit 0022, and a method of generating the illumination volume data in the illumination calculation unit 0023 will be described.

Figure 17:
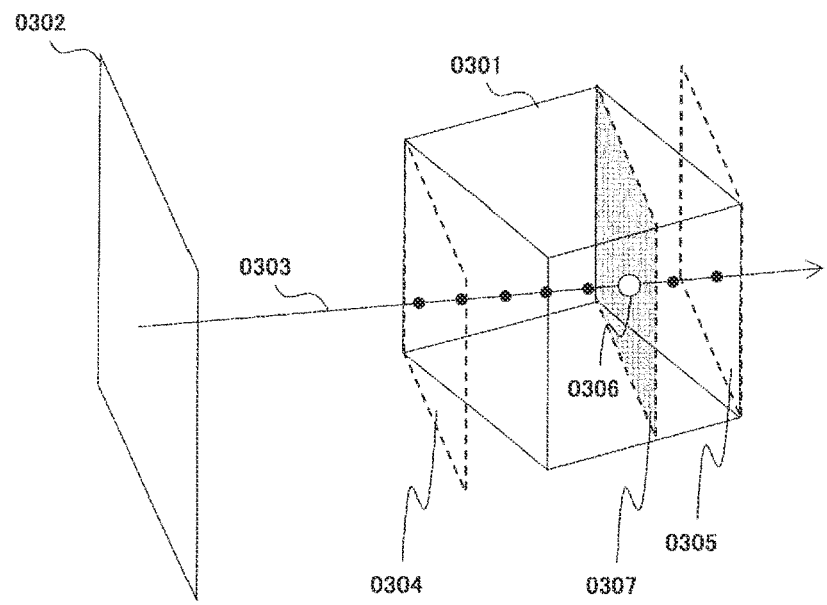
FIG. 17 is a conceptual diagram schematically illustrating a positional relation between luminance volume data or blood flow volume data and a light source.

FIG. 17 is a conceptual diagram schematically illustrating a positional relation between the luminance volume data or the blood flow volume data and the light source. As illustrated in FIG. 17, a light source (parallel light source) 0302 is set in a light source direction 0303 in luminance volume data or blood flow volume data 0301 in the luminance volume data storage unit 0015 by the control unit 0003 and the operation unit 0004. The position of the light source 0302, the light source direction 0303, and light source data in a three-dimensional space are generated by the light source information setting unit 0021.

A plane 0304 indicates a position of a plane in which the volume data (the luminance volume data or the blood flow volume data) 0301 first intersects (comes into contact with) an orthogonal plane in the light source direction 0303 and indicates an illumination calculation start position. A plane 0305 indicates a position of a plane in which the volume data (the luminance volume data or the blood flow volume data) 0301 finally intersects (comes into contact with) an orthogonal plane in the light source direction 0303 and indicates an illumination calculation end position.

The illumination calculation unit 0023 performs illumination calculation on a plane (an orthogonal plane in the light source direction 0303) orthogonal in the light source direction 0303. In FIG. 17, the illumination calculation unit 0023 performs the illumination calculation in a scope from the plane 0304 to the plane 0305. For example, the illumination calculation unit 0023 performs illumination calculation on a plane 0307 in illumination calculation of a sample 0306 located in the light source direction 0303.

Figure 18:
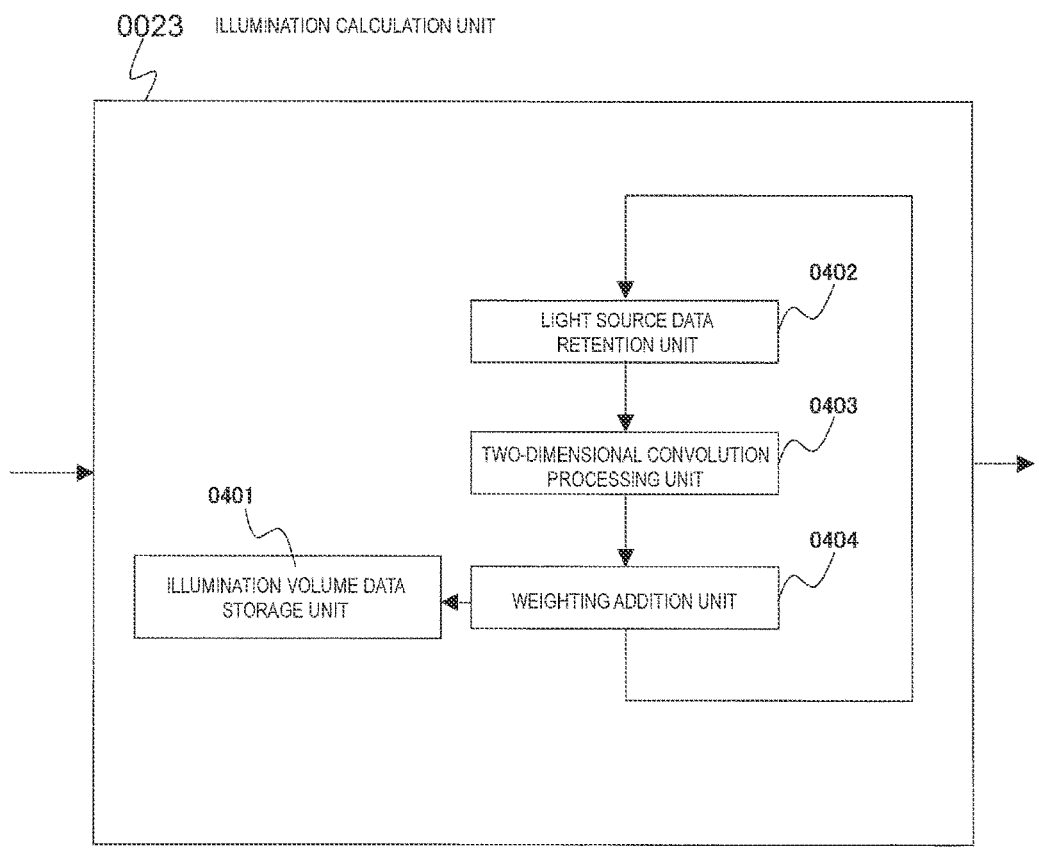
FIG. 18 is a block diagram illustrating an example of the configuration of an illumination calculation unit according to the second embodiment.

Next, an example of the configuration of the illumination calculation unit 0023 will be described with reference to FIG. 18. As illustrated in FIG. 18, the illumination calculation unit 0023 includes an illumination volume data storage unit 0401, a light source data retention unit 0402, a two-dimensional convolution processing unit 0403, and a weighting addition unit 0404. The illumination calculation unit 0023 includes the two-dimensional convolution processing unit 0403 that generates two-dimensional convolution integrated data by performing two-dimensional convolution integration on the light source data and the weighting addition unit 0404 that generates the illumination volume data by performing weighting addition on the light source data and the two-dimensional convolution integrated data based on the weight coefficient.

The illumination calculation unit 0023 includes the light source data retention unit 0402 that retains an initial value of the light source data and a result of the weighting addition obtained by the weighting addition unit as input light source data. The illumination calculation unit 0023 generates two-dimensional convolution integrated data by performing two-dimensional convolution integration on the input light source data while switching voxels from the illumination calculation start position to the illumination calculation end position of the luminance volume data, and generates the illumination volume data by performing weighting addition on the input light source data and the two-dimensional convolution integrated data based on the weight coefficient which is based on at least one of the luminance value and the blood flow value.

The light source data retention unit 0402 inputs the light source data generated by the light source information setting unit 0021 and retains the light source data as an initial value. Hereinafter, the light source data retained by the light source data retention unit 0402 is referred to as "input light source data". The two-dimensional convolution processing unit 0403 generates the two-dimensional convolution integrated data by performing the two-dimensional convolution integration on the input light source data (light source data). The two-dimensional convolution integration process indicates convolution integration on a two-dimensional plane and is performed on, for example, the plane 0307.

The weighting addition unit 0404 inputs the two-dimensional convolution integrated data which is an output result of the two-dimensional convolution processing unit 0403 and inputs the input light source data retained by the light source data retention unit 0402. The weighting addition unit 0404 generates the illumination volume data by performing the weighting addition on the input light source data (light source data) and the two-dimensional convolution integrated data based on the weight coefficient. The weight coefficient used by the weighting addition unit 0404 is set as the optical characteristics of the volume data (the luminance volume data or the blood flow volume data) in regard to the light source by the optical characteristic setting unit 0022. Hereinafter, a weighting addition result generated by the weighting addition unit 0404 is referred to as "output illumination data".

The output illumination data is stored at a position according to the coordinates of the voxels of the illumination volume data storage unit 0401. The output illumination data is input to the light source data retention unit 0402 and is stored (retained) as input light source data. That is, the light source data retention unit 0402 retains the initial value of the light source data and the result of the weighting addition by the weighting addition unit 0404 as the input light source data.

Here, the input light source data of the initial value is light source data set by the light source information setting unit 0021, and is input to the light source data retention unit 0402 to be set (retained) before the illumination calculation unit 0023 starts the illumination calculation.

The two-dimensional convolution processing unit 0403 and the weighting addition unit 0404 in the illumination calculation unit 0023 generate the two-dimensional convolution integrated data by performing the two-dimensional convolution integration on the input light source data, while switching the voxels corresponding to coordinates to be referred to from the illumination calculation start position (the plane 0304) to the illumination calculation end position (the plane 0305) of the luminance volume data or the blood flow volume data, and generate the illumination volume data by performing the weighting addition on the input light source data and the two-dimensional convolution integrated data using the weight coefficient which is based on the luminance value or the blood flow value, while changing the luminance value or the blood flow value corresponding to the coordinates to be referred to.

Figure 19:
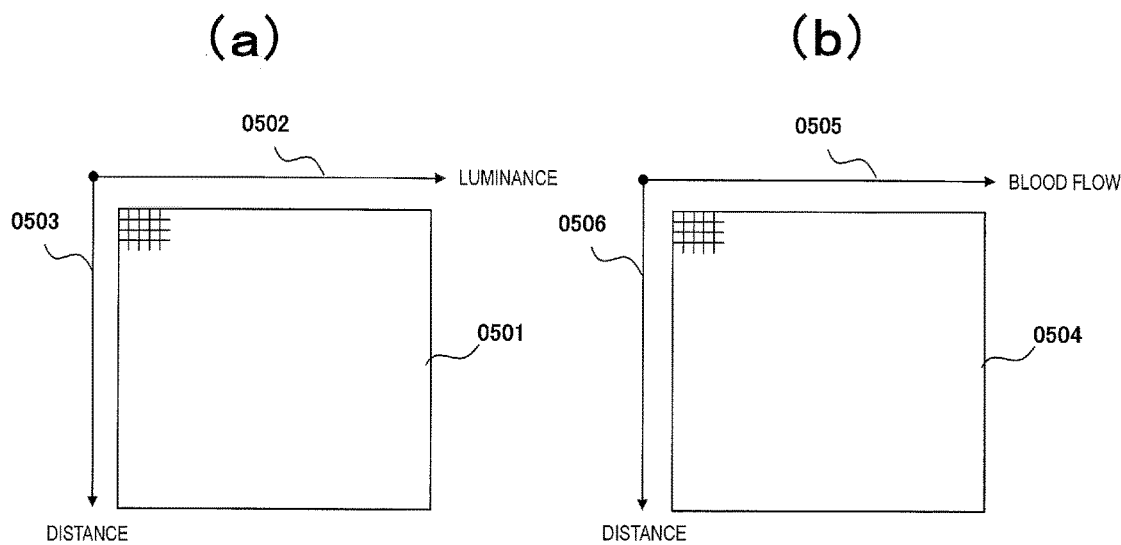
FIG. 19 is a diagram illustrating an example of a luminance two-dimensional weight coefficient table and a blood flow two-dimensional weight coefficient table according to the second embodiment.

Next, a method of setting the weight coefficient used by the weighting addition unit 0404 will be described with reference to FIG. 19. As illustrated in FIG. 19(*a*), a luminance two-dimensional weight coefficient table 0501 is a two-dimensional table which includes the weight coefficient (the weight coefficient based on the luminance value) set by the control unit 0003 and which is used to refer to the weight coefficient in which a luminance value 0502 of the luminance volume data and a distance 0503 from a body surface (or the surface of a tissue) are stored two-dimensionally as two indexes. As illustrated in FIG. 19(*b*), a blood flow two-dimensional weight coefficient table 0504 is a two-dimensional table which includes the weight coefficient (the weight coefficient based on the blood flow value) set by the control unit 0003 and which is used to refer to the weight coefficient in which a blood flow value (voxel value) 0505 of the blood flow volume data and a distance 0506 from a body surface (or the surface of a tissue) are stored two-dimensionally as two indexes. That is, the weight coefficients are regulated by the luminance two-dimensional weight coefficient table 0501 in which the luminance value of the luminance volume data and the distance from the surface of a target object are set as indexes and the blood flow two-dimensional weight coefficient table 0504 in which the blood flow value of the blood flow volume data and the distance from the surface of a target object are set as indexes. In this case, the optical characteristic setting unit 0022 sets the weight coefficients regulated by the luminance two-dimensional weight coefficient table 0501 and the blood flow two-dimensional weight coefficient table 0504. The optical characteristic setting unit 0022 sets the weight coefficient according to the luminance of the luminance volume data and the distance from the surface of the target object. The optical characteristic setting unit 0022 sets the weight coefficient according to the blood flow value of the blood flow volume data and the distance from the surface of a target object. That is, the optical characteristic setting unit 0022 sets the weight coefficient according to at least one voxel value of the plurality of pieces of volume data and the distance from the surface of the target object.

The optical characteristics according to the embodiment are regulated by the weight coefficient set so that a behavior (action) of light is replicated based on the optical characteristics of a tissue and are set by the optical characteristic setting unit 0022. The optical characteristic setting unit 0022 sets the luminance two-dimensional weight coefficient table 0501 that includes the weight coefficient as the optical characteristics of the luminance volume data and the blood flow two-dimensional weight coefficient table 0504 that includes the weight coefficient as the optical characteristics of the blood flow volume data.

As illustrated in FIG. 19(*a*), two weight coefficients a1 and b1 are referred to from the luminance two-dimensional weight coefficient table 0501 based on the two indexes, the luminance value of the luminance volume data and the distance from a body surface (or the surface of a tissue). As illustrated in FIG. 19(*b*), two weight coefficients a2 and b2 are referred to from the blood flow two-dimensional weight coefficient table 0504 based on the two indexes, the blood flow value of the blood flow volume data and the distance from a body surface (or the surface of a tissue). In the embodiment, a case in which one of the luminance two-dimensional weight coefficient table 0501 and the blood flow two-dimensional weight coefficient table 0504 is selected by a threshold value will be described. For example, either of the luminance two-dimensional weight coefficient table 0501 or the blood flow two-dimensional weight coefficient table 0504 is selected based on a luminance threshold value c1 by comparing the luminance threshold value c1 to the luminance value corresponding to coordinates to be referred to.

The weight coefficients a1 and a2 are weight coefficients having an influence on (multiplied to) the input light source data and the weight coefficients b1 and b2 are weight coefficients having an influence on (multiplied to) the two-dimensional convolution integrated data. When the luminance two-dimensional weight coefficient table 0501 is selected by the luminance threshold value c1, the weight coefficients a1 and b1 referred to from the luminance two-dimensional weight coefficient table 0501 are multiplied to the input light source data and the two-dimensional convolution integrated data. In this case, a behavior (the degree of diffusion or the like) of light in the luminance volume data can be simply set by adjusting the magnitudes of the weight coefficients a1 and b1. When the blood flow two-dimensional weight coefficient table 0504 is selected by the luminance threshold value c1, the weight coefficients a2 and b2 referred to from the blood flow two-dimensional weight coefficient table 0504 are multiplied to the input light source data and the two-dimensional convolution integrated data. In this case, a behavior of light in the blood flow volume data can be simply set by adjusting the magnitudes of the weight coefficients a2 and b2.

A relation between the luminance volume data and the blood flow volume data can be adjusted by adjusting the luminance threshold value c1. For example, when the luminance value of the luminance volume data corresponding to coordinates to be referred to is equal to or greater than the luminance threshold value c1, the weight coefficient at the coordinates is referred to from the luminance two-dimensional weight coefficient table 0501. When the luminance value of the luminance volume data corresponding to the coordinates to be referred to is less than the luminance threshold value c1, the weight coefficient at the coordinates is referred to from the blood flow two-dimensional weight coefficient table 0504. As a result, the relation between the luminance volume data and the blood flow volume data (the relation between the luminance two-dimensional weight coefficient table 0501 and the blood flow two-dimensional weight coefficient table 0504) can be adjusted by the luminance threshold value c1.

Either of the luminance two-dimensional weight coefficient table 0501 or the blood flow two-dimensional weight coefficient table 0504 may be selected based on the blood flow threshold value c2 instead of the luminance threshold value c1 by comparing the blood flow threshold value c2 to the blood flow value corresponding to the coordinates to be referred to. For example, when the blood flow value of the blood flow volume data corresponding to coordinates to be referred to is equal to or greater than the blood flow threshold value c2, the weight coefficient at the coordinates is referred to from the blood flow two-dimensional weight coefficient table 0504. When the blood flow value of the blood flow volume data corresponding to the coordinates to be referred to is less than the blood flow threshold value c2, the weight coefficient at the coordinates is referred to from the luminance two-dimensional weight coefficient table 0501. As a result, the relation between the luminance volume data and the blood flow volume data (the relation between the luminance two-dimensional weight coefficient table 0501 and the blood flow two-dimensional weight coefficient table 0504) can be adjusted by the blood flow threshold value c2.

The luminance threshold value c1 and the blood flow threshold value c2 may be combined and either of the luminance two-dimensional weight coefficient table 0501 or the blood flow two-dimensional weight coefficient table 0504 may be selected. Either of the luminance two-dimensional weight coefficient table 0501 or the blood flow two-dimensional weight coefficient table 0504 may be selected by the plurality of luminance threshold values c1 or the plurality of blood flow threshold value c2. A new weight coefficient may be calculated by calculating an average or a weighted average of the weight coefficients of the luminance two-dimensional weight coefficient table 0501 and the blood flow two-dimensional weight coefficient table 0504.

The referred weight coefficient and a weighted sum (a result of the weighting addition) added after the weight coefficients are respectively applied to the light source data and the two-dimensional convolution integrated data are output to the illumination volume data storage unit 0401. By setting the sum value of the referred weight coefficients (the weight coefficients a1 and b1 referred from the luminance two-dimensional weight coefficient table 0501 or the weight coefficients a2 and b2 referred to from the blood flow two-dimensional weight coefficient table 0504) to be large, it is possible to set reinforced illumination. By setting the sum value of the weight coefficients to be small, it is possible to set weak illumination.

In the embodiment, the two-dimensional weight coefficient table 0501 includes the luminance and the distance from a body surface (or the surface of a tissue) as two reference indexes. In the case of ultrasonic data, luminance reflecting acoustic impedance of a tissue can be useful information reflecting the characteristics of a biological tissue. Luminance in ultrasonic data reflects the amplitude of a reflected wave obtained by reflecting a radiated ultrasonic wave from a diffusing body, and thus is normally attenuated with propagation of the ultrasonic wave in a deep portion. Thus, in regard to the ultrasonic data, it is difficult to classify tissues based on only the luminance. Accordingly, by adding a distance from the body surface of a target object (or the surface of a tissue) as an index, it is possible to classify tissues in regard to the ultrasonic data.

For example, when a target object is an unborn child and an ultrasonic wave arriving at an arm of the unborn child via an amniotic water is considered, the luminance of the ultrasonic wave reflected from a diaphysis (hard tissue) of the arm is well known to be high.

However, the luminance at the moment at which the ultrasonic wave arrives at the surface of the arm is not attenuated even when the surface of the arm is a soft tissue. Therefore, the luminance is well known to be high as in a diaphysis. Thus, when only the luminance is used as an index, it is difficult to distinguish a soft tissue from a diaphysis (hard tissue). Accordingly, a distance from the body surface of a target object is added as an index. A diaphysis is present inside a tissue of an unborn child. Therefore, by setting the characteristics of the tissue using both of luminance and a distance from a body surface (or the surface of a tissue), it is possible to discriminate the tissue.

For example, in regard to a distance from a body surface (or the surface of a tissue), when the luminance of a certain voxel is higher than a preset threshold value, the luminance is determined to correspond to a tissue, and thus a distance corresponding to 1 voxel is added as the value of the distance from the body surface (or the surface of the tissue). Conversely, when the luminance of a certain voxel is lower than the preset threshold value, the luminance is determined not to correspond to a tissue, and thus the value of the distance from the body surface (or the surface of the tissue) in the voxel is initialized.

A distance from a body surface (or the surface of a tissue) can be used as the index of the weight coefficient. Then, when a soft tissue with high luminance is present on the surface of a tissue as in an arm of an unborn child and a diaphysis with substantially the same luminance as the soft tissue is present at a deep position from the surface of a tissue, a different optical effect can be provided depending on a tissue despite substantially the same luminance by setting a different weight coefficient according to a distance from the body surface (or the surface of the tissue). That is, by distinguishing a soft tissue from a diaphysis (hard tissue) according to a distance from a body surface (or the surface of a tissue) and setting a different weight coefficient, a behavior (diffusion, absorption, reflection, and the like) of light in a tissue can be expressed so that the soft tissue is distinguished from the diaphysis (hard tissue), and thus an image of which reality is improved can be obtained in a volume rendering method. By using a characteristic weight coefficient according to the characteristics of a tissue, a proper optical effect can be provided even when it is difficult to specify the characteristics (or kind) of the tissue by only the luminance value as in ultrasonic data.

In this way, by setting the two-dimensional weight coefficient table reflecting the characteristics of tissues without performing complicated calculation and adjusting a behavior (the degree of diffusion or the like) of light based on the two-dimensional weight coefficient table, optical effects in the tissues can be provided simply or arbitrarily, and thus a three-dimensional image of which reality is improved can be generated according to the characteristics (for example, hardness or softness of tissues) of the tissues.

In the embodiment, the two-dimensional weight coefficient table 0504 includes a blood flow value and a distance from a blood vessel (or the surface of a blood flow) as two reference indexes. In the case of ultrasonic data, it is determined in some cases that there is a blood flow even at a location at which a pseudo blood flow component is detected due to a motion of a tissue or a probe and a blood flow is not actually present. Thus, in the ultrasonic data, it is difficult to classify tissues based on only a blood flow value in some cases. Accordingly, by adding a distance from a blood flow surface (or the surface of a tissue) as an index, it is possible to classify tissues in regard to the ultrasonic data.

For example, when a blood flow value is equal to or greater than the blood flow threshold value c2 and the weight coefficient is referred to from the blood flow two-dimensional weight coefficient table 0504 and when a distance from the surface of a blood vessel is greater than a predetermined threshold value, the blood flow value corresponding to coordinates to be referred to is considered to be caused from a pseudo blood flow component rather than an actual blood flow. Therefore, by setting the weight coefficients a2 and b2 in the blood flow two-dimensional weight coefficient table 0504 to be the same as weight coefficients of a peripheral tissue and expressing a behavior (diffusion, absorption, reflection, or the like) of light in a tissue without distinction of the peripheral tissue, the weight coefficients can be set so that the behavior (action) of the light is not reflected to a portion having the blood flow value caused due to a pseudo blood flow component. Thus, it is possible to generate the three-dimensional image of which reality is improved.

The illumination calculation unit 0023 repeatedly performs the foregoing illumination calculation process while switching a voxel corresponding to the coordinates to be referred to by the weighting addition unit 0404 from the illumination calculation start position (the plane 0304) to the illumination calculation end position (the plane 0305) and switching a luminance value corresponding to coordinates to be referred to. The illumination calculation unit 0023 selects one piece of volume data from two pieces of volume data (the luminance volume data and the blood flow volume data) for respective coordinates of the volume data, calculates illumination of a position according to the coordinates based on the optical characteristics (or the weight coefficients) of the selected volume data, and generates the illumination volume data based on the calculated illumination.

The illumination calculation unit 0023 performs the calculation up to the illumination calculation end position to generate illumination volume data in which all of the illumination corresponding to voxel coordinates on the volume data are calculated, and then stores the illumination volume data in the illumination volume data storage unit 0401.

The behavior characteristics of light differ depending on a wavelength of a light source according to the law of nature. Accordingly, when the reality is further improved in conformity to the law of nature, the illumination calculation is performed for each wavelength of the light source. In this case, the weight coefficients differ for each wavelength of the light source.

The light source information setting unit 0021 sets the light source data according to a plurality of wavelengths of the light source. The optical characteristic setting unit 0022 sets the weight coefficients for each of the plurality of wavelengths.

The illumination calculation unit 0023 performs the illumination calculation for each of the plurality of wavelengths of the light source 0302 to generate the illumination volume data. For example, when the light source 0302 is 7 colors of the visible light, the illumination calculation unit 0023 sets 7 kinds of weight coefficients (or two-dimensional weight coefficient tables) and generates 7 kinds of pieces of illumination volume data. When the light source 0302 is the three primary colors of additive color mixture, the illumination calculation unit 0023 sets three sets of weight coefficients (or three kinds of two-dimensional weight coefficient tables) corresponding to wavelengths of the R, G, and B components and generates three kinds of pieces of illumination volume data. That is, the light source information setting unit 0021 sets the light source data according to the plurality of wavelengths of the light source, the optical characteristic setting unit 0022 sets the weight coefficient for each of the plurality of wavelengths, and the illumination calculation unit 0023 generates the illumination volume data for each of the plurality of wavelengths.

In the embodiment, a case will be described in which the light source 0302 is the three primary colors of additive color mixture, three sets of weight coefficients (or three kinds of two-dimensional weight coefficient tables) are set, and three kinds of pieces of illumination volume data are generated. An initial value of the light source data is set for each wavelength of the light source 0302. That is, the same number of initial values of the light source data as the number of effective wavelengths is set by the light source information setting unit 0021. Accordingly, in the embodiment, three kinds of pieces of light source data corresponding to the wavelengths of the R, G, and B components are set and are each retained as independent input light source data by the light source data retention unit 0402. The initial values of the three kinds of pieces of light source data may be initial values selected via the operation unit 0004 by an operator or may be initial values set using an image.

The illumination calculation unit 0023 calculates the illumination disposed on the luminance volume data based on the three kinds of light source data and three kinds of optical characteristics (the weight coefficient or two-dimensional coefficient table) and generates three kinds of pieces of illumination volume data.

The projection processing unit 0018 generates a three-dimensional image based on opacity referred to by the illumination of the illumination volume data and the voxel value of the luminance volume data (the luminance value of the luminance volume data or the blood flow value of the blood flow volume data). When the light source 0302 is the three primary colors, the projection processing unit 0018 generates the three-dimensional image from the three kinds of pieces of illumination volume data generated by the illumination calculation unit 0023, the luminance volume data stored in the luminance volume data storage unit 0015, and the blood flow volume data stored in the blood flow volume data storage unit 0035. A projection process in the projection processing unit 0018 is performed based on illumination (voxel value), opacity α[i], and gradient values S[i] in illumination volume data L_r[k], L_g[k], and L_b[k] of the respective wavelengths (the R, G, and B components), as shown in equations (4) to (6) below, to generate the three-dimensional image. That is, the three-dimensional image is generated by multiplying voxel values in illumination volume data L_r[k], L_g[k], and L_b[k] of the respective wavelengths by opacity terms obtained by opacity α[i] and values of gradient values S[i] and performing summation in a visual line direction. In the equations, "k" indicates voxel coordinates in the visual line direction. The visual line direction is set as a direction in which an ultrasonic image is observed via the control unit 0003 by the operation unit 0004.

Here, the opacity α[i] and the gradient value S[i] are preferably set from the opacity referred to by either of the luminance volume data or the blood flow volume data and the gradient value of either of the luminance gradient volume data or the blood flow gradient volume data according to selection of the luminance two-dimensional weight coefficient table 0501 and the blood flow two-dimensional weight coefficient table 0504 referred to by the weighting addition unit 0404. The opacity α[i] and the gradient value S[i] are set for each voxel. For example, when the weight coefficient is referred to from the luminance two-dimensional weight coefficient table 0501 in an i-th voxel in the visual line direction, the opacity α[i] referred to by the luminance volume data and the gradient value S[i] of the luminance gradient volume data are set. Further, when the weight coefficient is referred to from the blood flow two-dimensional weight coefficient table 0504 in an i-th voxel in the visual line direction, the opacity α[i] referred to by the blood flow volume data and the gradient value S[i] of the blood flow gradient volume data are set.

$$\text{OUT\_}R[K] = \Sigma^{k=0:k}((L\_r[k] \cdot S[k]) \cdot \alpha[k] \cdot \Pi^{m=0:k-1}(1-\alpha[m])) \quad (4)$$

$$\text{OUT\_}G[K] = \Sigma^{k=0:k}((L\_g[k] \cdot S[k]) \cdot \alpha[k] \cdot \Pi^{m=0:k-1}(1-\alpha[m])) \quad (5)$$

$$\text{OUT\_}B[K] = \Sigma^{k=0:k}((L\_b[k] \cdot S[k]) \cdot \alpha[k] \cdot \Pi^{m=0:k-1}(1-\alpha[m])) \quad (6)$$

The three-dimensional image generated by the three-dimensional image processing unit 0016 is disposed on the same screen as an arbitrary cross-sectional image by the image combination unit 0017 and is displayed by the display unit 0009.

In the embodiment, the ultrasonic diagnostic device 0001 includes the gradient calculation units 0019 and 0039, but may also exclude the gradient calculation units 0019 and 0039. In this case, the terms of gradient values S[i] in equations (4) to (6) are excluded from equations (4) to (6) (or are treated as "1.0") so that these terms do not contribute to the three-dimensional image to be generated.

Figure 20:
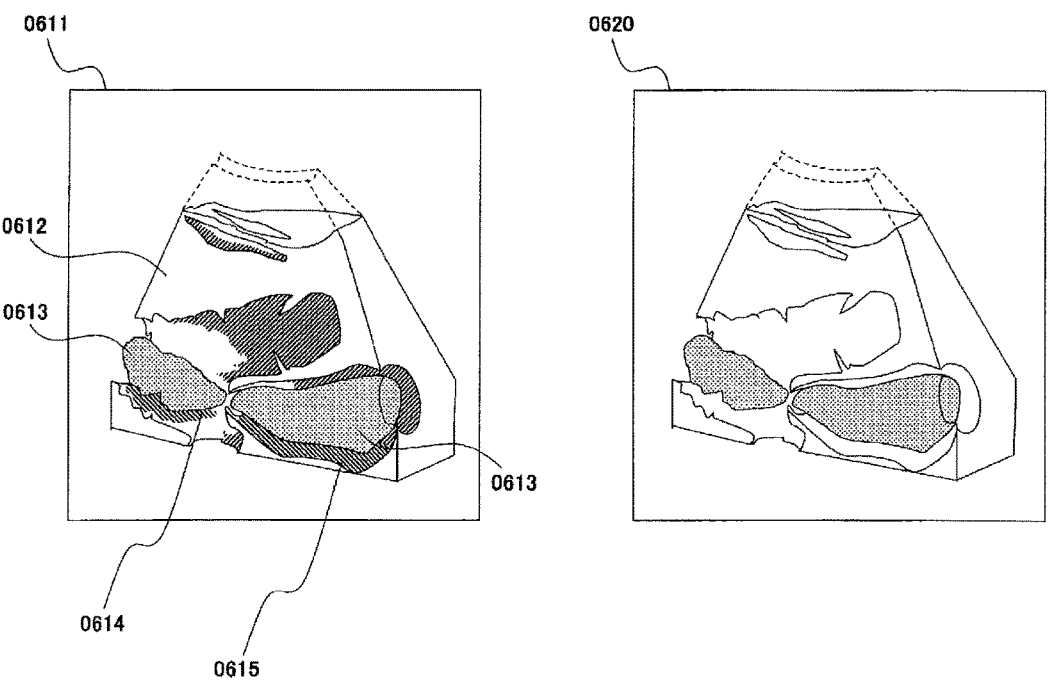
FIG. 20 is a diagram for describing characteristics of a three-dimensional image according to the second embodiment.

Next, the characteristics of the three-dimensional image according to the embodiment will be described with reference to FIG. 20. A three-dimensional image 0611 in FIG. 20 is a three-dimensional image constructed according to a method according to the embodiment. As illustrated in FIG. 20, a bright portion 0612 on the three-dimensional image 0611 indicates a muscle tissue of a heart and a dark portion 0613 indicates a blood flow. When the method according to the embodiment is used, light passes through a blood vessel so that a portion 0614 in a muscle portion colors red is generated. When the method according to the embodiment is used, light passes through both of a blood vessel and a muscle tissue so that diffusion and absorption of light occur by interaction of the light, and thus a portion 0615 in which a muscle tissue is dark and colors red is generated. In this way, the behavior of the light occurring by passing the light through the blood vessel or the interaction of light in the adjacent tissue can be expressed. A three-dimensional image 0620 is an example of a general three-dimensional image in which the method according to the embodiment is not used. When the three-dimensional image 0611 generated using the method according to the embodiment is compared to the three-dimensional image 0620, the three-dimensional image 0611 can be known to be a stereoscopic and realistic three-dimensional image compared to the three-dimensional image 0620. Accordingly, by using the method according to the embodiment, it is possible to obtain a natural image of which reality is improved in a volume rendering method.

Figure 21:
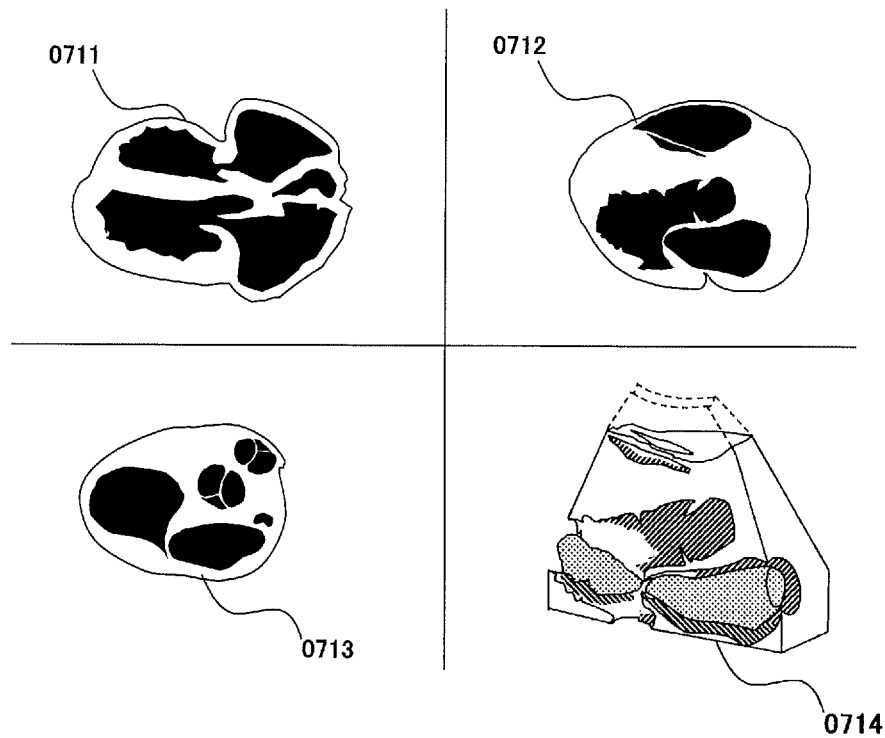
FIG. 21 is a diagram illustrating display examples according to the second embodiment.

FIG. 21 is a diagram illustrating a display example according to the embodiment. As illustrated in FIG. 21, three cross-sectional surfaces 0711, 0712, and 0713 of which planes are orthogonal to each other and a three-dimensional image 0714 are simultaneously displayed. The three-dimensional image generated by the three-dimensional image processing unit 0016 is disposed on the same screen as the three orthogonal cross-sectional surfaces (or arbitrary cross-sectional images) 0711, 0712, and 0713 by the image combination unit 0017 to be displayed by the display unit 0009. By observing the surface by the three-dimensional image with reference to each cross-sectional surface, it is possible to improve inspection precision and efficiency.

The embodiment has been described above, but the present invention is not limited thereto and is alternated and modified within the scope described in the claims.

Figure 22:
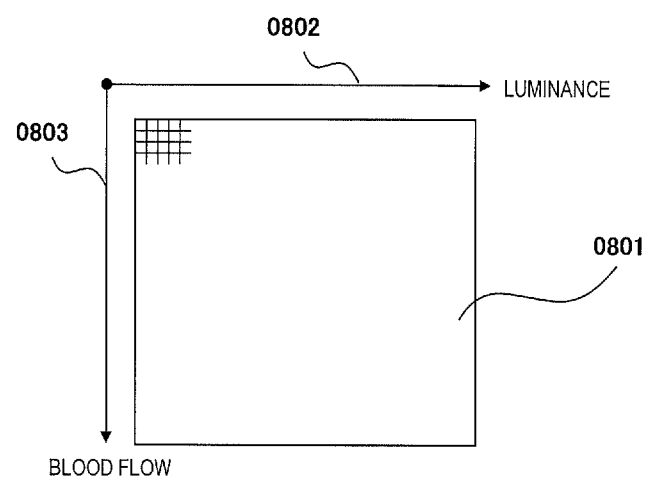
FIG. 22 is a diagram illustrating a modification example of a luminance blood flow two-dimensional weight coefficient table according to the second embodiment.

FIG. 22 is a diagram illustrating a modification example of the two-dimensional weight coefficient table according to the embodiment. As illustrated in FIG. 22, instead of the two two-dimensional weight coefficient tables (the luminance two-dimensional weight coefficient table 0501 and the blood flow two-dimensional weight coefficient table 0504), a luminance blood flow two-dimensional weight coefficient table 0801 may be used in the weighting addition unit 0404. The luminance blood flow two-dimensional weight coefficient table 0801 is a two-dimensional table which includes weight coefficients (weight coefficients based on a luminance value and a blood flow value) set by the control unit 0003 and is used to refer to the weight coefficients in which a luminance value 0802 of the luminance volume data and a blood flow value 0803 of the blood flow volume data are stored as two indexes two-dimensionally. That is, the weight coefficients are regulated by the luminance blood flow two-dimensional weight coefficient table 0801 in which the luminance value of the luminance volume data and the blood flow value of the blood flow volume data are set as indexes. In this case, the optical characteristic setting unit 0022 sets the weight coefficients regulated by the luminance blood flow two-dimensional weight coefficient table 0801. The optical characteristic setting unit 0022 sets the weight coefficients according to the luminance of the luminance volume data and the blood flow value of the blood flow volume data. The optical characteristics in the embodiment are regulated by the weight coefficients set so that a behavior (action) of light is replicated based on the optical characteristics of a tissue, and are set by the optical characteristic setting unit 0022. The optical characteristic setting unit 0022 sets the luminance blood flow two-dimensional weight coefficient table 0801 which includes the weight coefficients as the optical characteristics of the luminance volume data and the blood flow volume data. As illustrated in FIG. 22, two weight coefficients a3 and b3 are referred to from the luminance blood flow two-dimensional weight coefficient table 0801 based on the two indexes, the luminance of the luminance volume data and the blood flow value of the blood flow volume data. The weight coefficient a3 is a weight coefficient having an influence on (multiplied to) the input light source data and the weight coefficient b3 is a weight coefficient having an influence on (multiplied to) the two-dimensional convolution integrated data. In this case, a behavior of light in the luminance volume data and a behavior of light in the blood flow volume data can be simply set by adjusting the magnitudes of the weight coefficients a3 and b3. Further, it is not necessary to select either of the luminance two-dimensional weight coefficient table 0501 or the blood flow two-dimensional weight coefficient table 0504 by the threshold values c1 and c2 or the like, and thus it is possible to simply set the behavior of light corresponding to the luminance and the blood flow can be simply set using the single luminance blood flow two-dimensional weight coefficient table 0801.

Figure 23:
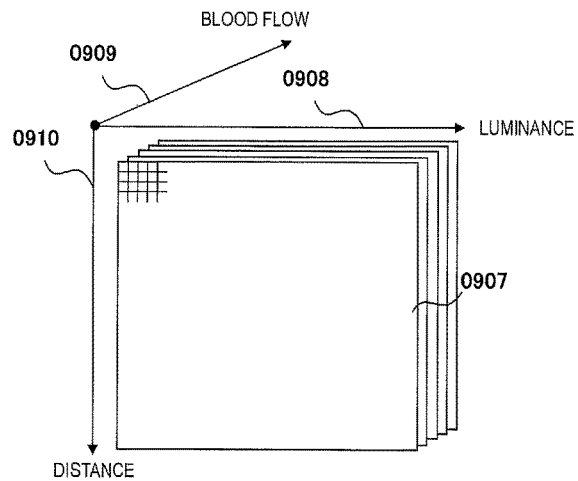
FIG. 23 is a diagram illustrating an example of a luminance blood flow three-dimensional weight coefficient table according to the second embodiment.

FIG. 23 is a diagram illustrating another modification example of the weight coefficient table according to the embodiment. As illustrated in FIG. 23, instead of the two-dimensional weight coefficient table, a luminance blood flow three-dimensional weight coefficient table 0907 may be used in the weighting addition unit 0404. The luminance blood flow three-dimensional weight coefficient table 0907 is a three-dimensional table which includes weight coefficients (weight coefficients based on a luminance value and a blood flow value) set by the control unit 0003 and which is used to refer to the weight coefficients in which a luminance value 0908 of the luminance volume data, a blood flow value 0909 of the blood flow volume data, and a distance 0910 from a body surface (or the surface of a tissue) are stored as three indexes three-dimensionally. That is, the weight coefficients are regulated by the luminance blood flow three-dimensional weight coefficient table 0907 in which the luminance value of the luminance volume data, the blood flow value of the blood flow volume data, and the distance from the surface of a target object are set as indexes. In this case, the optical characteristic setting unit 0022 sets the weight coefficients regulated by the luminance blood flow three-dimensional weight coefficient table 0907. The optical characteristic setting unit 0022 sets the weight coefficients according to the luminance value of the luminance volume data, the blood flow value of the blood flow volume data, and the distance from the surface of a target object. That is, the optical characteristic setting unit 0022 sets the weight coefficients according to at least two voxel values of the plurality of pieces of volume data and the distance from the surface of the target object.

The optical characteristics in the embodiment are regulated by the weight coefficients set so that a behavior (action) of light is replicated based on the optical characteristics of a tissue, and are set by the optical characteristic setting unit 0022. The optical characteristic setting unit 0022 sets the luminance blood flow three-dimensional weight coefficient table 0907 which includes the weight coefficients as the optical characteristics of the luminance volume data and the blood flow volume data. As illustrated in FIG. 23, two weight coefficients a4 and b4 are referred to from the luminance blood flow three-dimensional weight coefficient table 0907 based on the three indexes, the luminance of the luminance volume data, the blood flow value of the blood flow volume data, and the distance from the surface of a target object. The weight coefficient a4 is a weight coefficient having an influence on (multiplied to) the input light source data and the weight coefficient b4 is a weight coefficient having an influence on (multiplied to) the two-dimensional convolution integrated data. In this case, a behavior of light in the luminance volume data and a behavior of light in the blood flow volume data can be simply set by adjusting the magnitudes of the weight coefficients a4 and b4. Further, it is not necessary to select either of the luminance two-dimensional weight coefficient table 0501 or the blood flow two-dimensional weight coefficient table 0504 by the threshold values c1 and c2 or the like, and thus it is possible to simply set the behavior of light corresponding to the luminance and the blood flow can be simply set using the single luminance blood flow three-dimensional weight coefficient table 0907. Thus, a tissue can be distinguished and expressed according to the distance.

Third Embodiment

Figure 24:
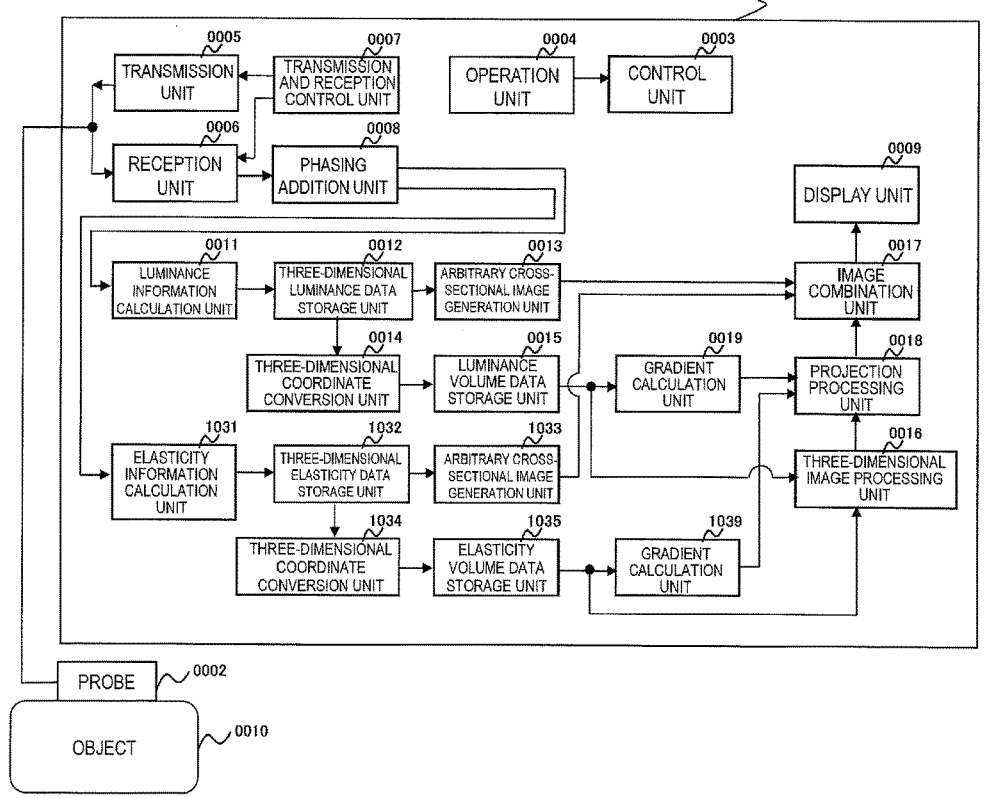
FIG. 24 is a block diagram illustrating an example of an ultrasonic diagnostic device according to a third embodiment.

Hereinafter, the ultrasonic diagnostic device 0001 according to a third embodiment of the present invention will be described with reference to the drawings. FIG. 24 is a block diagram illustrating an example of the ultrasonic diagnostic device according to the embodiment. In the embodiment, differences from the second embodiment will be mainly described and the other portions are the same as those of the second embodiment. The constituent elements denoted by the same reference numerals as those of the second embodiment have the same functions and operations as those of the second embodiment. As illustrated in FIG. 24, the ultrasonic diagnostic device 0001 includes a control unit 0003, an operation unit 0004, a transmission unit 0005, a reception unit 0006, a transmission and reception control unit 0007, a phasing addition unit 0008, a display unit 0009, a luminance information calculation unit 0011, a three-dimensional luminance data storage unit 0012, an arbitrary cross-sectional image generation unit 0013, a three-dimensional coordinate conversion unit 0014, a luminance volume data storage unit 0015, a three-dimensional image processing unit 0016, an image combination unit 0017, a projection processing unit 0018, and a gradient calculation unit 0019.

The ultrasonic diagnostic device 0001 includes an elasticity information calculation unit 1031, a three-dimensional elasticity data storage unit 1032, an arbitrary cross-sectional image generation unit 1033, a three-dimensional coordinate conversion unit 1034, an elasticity volume data storage unit 1035, and a gradient calculation unit 1039. The ultrasonic diagnostic device 0001 displays a three-dimensional image of a target object based on luminance volume data and elasticity volume data. An ultrasonic probe 0002 is connected to the ultrasonic diagnostic device 0001.

The elasticity information calculation unit 1031 constructs elasticity tomographic images based on the RF signal frame data generated by the phasing addition unit 0008. The three-dimensional elasticity data storage unit 1032 stores the plurality of elasticity tomographic images constructed by the elasticity information calculation unit 1031. The arbitrary cross-sectional image generation unit 1033 generates arbitrary cross-sectional images based on the acquired shapes of the elasticity tomographic images. The three-dimensional coordinate conversion unit 1034 performs three-dimensional coordinate conversion based on the acquired shapes of the elasticity tomographic images to generate elasticity volume data and stores the elasticity volume data in the elasticity volume data storage unit 1035.

The three-dimensional image processing unit 0016 generates illumination volume data using the luminance volume data stored in the luminance volume data storage unit 0015 and the elasticity volume data stored in the elasticity volume data storage unit 1035.

The gradient calculation unit 1039 generates elasticity gradient volume data using the elasticity volume data stored in the elasticity volume data storage unit 1035. A gradient value of the gradient volume data (the elasticity gradient volume data) is a value indicating a slope (for example, a slope of a normal line in a three-dimensional shape or an angle between of the normal line in the three-dimensional shape and a light source direction) of a three-dimensional shape calculated based on an elasticity value.

The projection processing unit 0018 generates a three-dimensional image by performing a rendering process using the illumination volume data, the luminance volume data, and the luminance gradient volume data to generate a three-dimensional image. The projection processing unit 0018 generates a three-dimensional image by performing a rendering process using the illumination volume data, the elasticity volume data, and the elasticity gradient volume data. The projection processing unit 0018 selects luminance or elasticity for each voxel. When the luminance is selected, the rendering calculation is performed on the voxel using the illumination volume data, the luminance volume data, and the luminance gradient volume data. When the elasticity is selected, the rendering calculation is performed on the voxel using the illumination volume data, the elasticity volume data, and the elasticity gradient volume data. The projection processing unit 0018 generates a three-dimensional image by integrating the results of the rendering calculation on the voxels in accordance with the luminance or the elasticity into the entire volume. The image combination unit 0017 combines the three-dimensional image generated by the projection processing unit 0018, the arbitrary cross-sectional image of three-dimensional luminance data generated by the arbitrary cross-sectional image generation unit 0013, and the arbitrary cross-sectional image of the three-dimensional elasticity data generated by the arbitrary cross-sectional image generation unit 1033. The display unit 0009 displays a display image generated by the image combination unit 0017.

Next, a process for the three-dimensional luminance data and the three-dimensional elasticity data will be described. The ultrasonic probe 0002 can transmit and receive the ultrasonic waves and can perform measurement along two axes of, for example, $\theta$ and $\phi$ while switching transmission and reception directions two-dimensionally. The luminance information calculation unit 0011 constructs two-dimensional luminance data by inputting the RF signal frame data output from the phasing addition unit 0008 based on a setting condition in the control unit 0003 and performing signal processing such as gain correction, log compression, detection, contour enhancement, and a smoothing process.

An elasticity value is measured from frame data by calculating an amount of strain occurring when a probe is manually or mechanically pressed against an object upward and downward. The elasticity information calculation unit 1031 stores the RF signal frame data output from the phasing addition unit 0008, measures displacement of a biological tissue from at least two pieces of frame data, and generates displacement information. The elasticity information calculation unit 1031 performs elasticity information calculation of obtaining strain or modulus of elasticity from the displacement information and performs a process such as contour enhancement and a smoothing process to construct two-dimensional elasticity data. The two-dimensional elasticity data is configured to include at least an amount of displacement, an amount of strain, and modulus of elasticity.

The three-dimensional elasticity data storage unit 1032 has a function of storing a plurality of pieces of two-dimensional elasticity data, which is output data of the elasticity information calculation unit 1031, based on transmission and reception directions corresponding to acquisition positions. For example, a plurality of pieces of two-dimensional elasticity data obtained by driving and acquiring two-dimensional elasticity tomographic images, generated from measurement results when time-series ultrasonic data sampled in a depth direction is transmitted and received in a θ direction, in a φ direction orthogonal to the θ direction in association with φ are stored as three-dimensional elasticity data.

The three-dimensional coordinate conversion unit 1034 performs three-dimensional coordinate conversion on coordinates in a space based on the acquisition positions (depth, θ, φ) using the three-dimensional elasticity data stored in the three-dimensional elasticity data storage unit 1032, generates elasticity volume data, and stores the elasticity volume data in the elasticity volume data storage unit 1035.

The arbitrary cross-sectional image generation unit 1033 generates an arbitrary cross-sectional image of the three-dimensional elasticity data on an arbitrary plane in a three-dimensional space set by the control unit 0003 and the operation unit 0004 based on the acquisition positions (depth, θ, φ) using the three-dimensional elasticity data stored in the three-dimensional elasticity data storage unit 1032.

The gradient calculation unit 1039 generates volume data in which a gradient in a visual line direction at respective voxel coordinates is calculated based on the elasticity volume data stored in the elasticity volume data storage unit 1035.

Next, a process of the three-dimensional image processing unit 0016 will be described. The three-dimensional image processing unit 0016 is a characteristic processing unit of the ultrasonic diagnostic device 0001 according to the embodiment and generates illumination volume data based on a light source in the three-dimensional space set by the control unit 0003 and the operation unit 0004, using the luminance volume data stored in the luminance volume data storage unit 0015 and the elasticity volume data stored in the elasticity volume data storage unit 1035.

Figure 25:
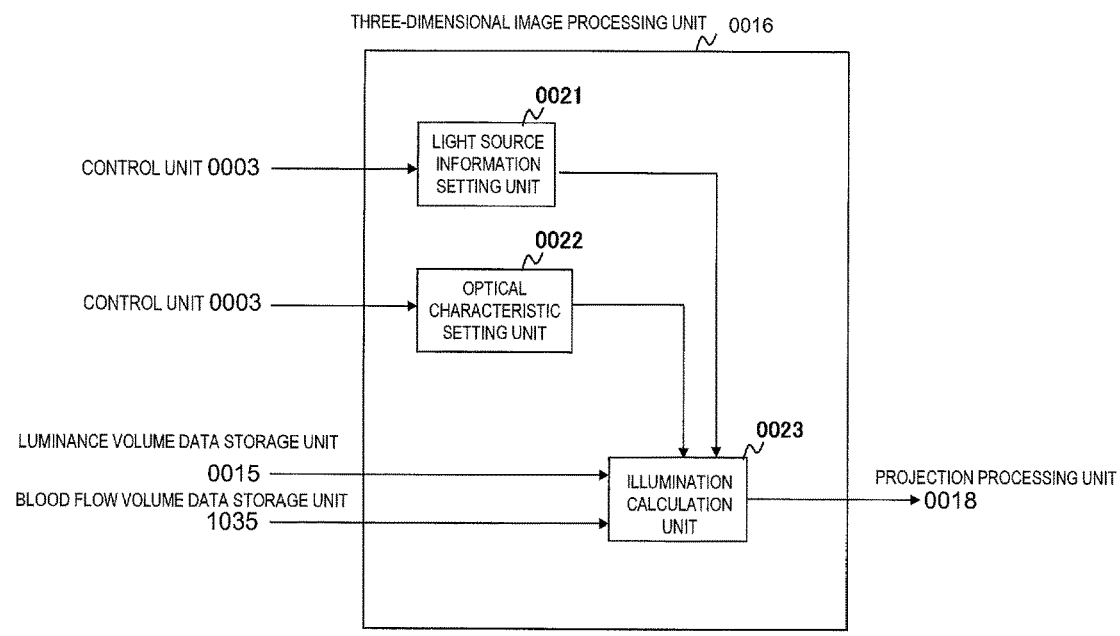
FIG. 25 is a block diagram illustrating an example of a three-dimensional image processing unit according to the third embodiment.

FIG. 25 is a block diagram illustrating an example of the three-dimensional image processing unit 0016. As illustrated in FIG. 25, the three-dimensional image processing unit 0016 includes a light source information setting unit 0021, an optical characteristic setting unit 0022, and an illumination calculation unit 0023.

The ultrasonic diagnostic device 0001 according to the embodiment is the ultrasonic diagnostic device 0001 that displays a three-dimensional image of a target object based on luminance volume data and the elasticity volume data. The ultrasonic diagnostic device 0001 includes the light source information setting unit 0021 that sets light source data indicating the characteristics of a light source set in a three-dimensional space, the optical characteristic setting unit 0022 that sets a weight coefficient indicating optical characteristics of the luminance volume data and a weight coefficient indicating optical characteristics of the elasticity volume data in regard to the light source, the illumination calculation unit 0023 that calculates at least one of illumination of a position according to coordinates of the luminance volume data and illumination of a position according to coordinates of the elasticity volume data based on the light source data and the weight coefficients and generates illumination volume data based on the calculated illumination, and the projection processing unit 0018 that generates the three-dimensional image from at least one of the luminance volume data and the elasticity volume data and the illumination volume data.

A method of generating an ultrasonic three-dimensional image according to the embodiment is an ultrasonic wave three-dimensional image generation method of displaying a three-dimensional image of a target object based on the luminance volume data and the elasticity volume data. The method includes setting light source data indicating characteristics of a light source set in a three-dimensional space, setting a weight coefficient indicating optical characteristics of the luminance volume data and a weigh coefficient indicating the optical characteristics of the elasticity volume data in regard to the light source, calculating at least one of illumination of a position according to coordinates of the luminance volume data and illumination of a position according to coordinates of the elasticity volume data based on the light source data and the weight coefficients, generating illumination volume data based on the calculated illumination, and generating the three-dimensional image from at least one of the luminance volume data and the elasticity volume data and the illumination volume data.

The light source information setting unit 0021 sets (generates) light source data indicating the characteristics of the light source set in the three-dimensional space of the three-dimensional image. For example, the light source information setting unit 0021 sets light source data indicating strength of the light source. The light source information setting unit 0021 can also adjust at least one of the strength of the light source, a position of the light source in the three-dimensional space, a direction of the light source, color tone of the light source, and a shape of the light source to set the light source data. The optical characteristic setting unit 0022 sets the optical characteristics of the luminance volume data and the elasticity volume data set by the control unit 0003 and the operation unit 0004. The optical characteristic setting unit 0022 sets weight coefficients indicating the optical characteristics of the luminance volume data and the elasticity volume data in regard to the light source. The illumination calculation unit 0023 calculates illumination corresponding to the coordinates of voxels on the output illumination volume data using at least one of the luminance volume data and the elasticity volume data based on the light source data set by the light source information setting unit 0021 and the optical characteristics set by the optical characteristic setting unit 0022 and generates illumination volume data.

That is, the illumination calculation unit 0023 calculates the illumination based on the light source data, the weight coefficients, the luminance volume data, and the volume data (the luminance volume data or the elasticity volume data) and generates the illumination volume data based on the calculated illumination.

Next, light source information set by the light source information setting unit 0021, optical characteristics set by the optical characteristic setting unit 0022, and a method of generating the illumination volume data in the illumination calculation unit 0023 will be described.

Figure 26:
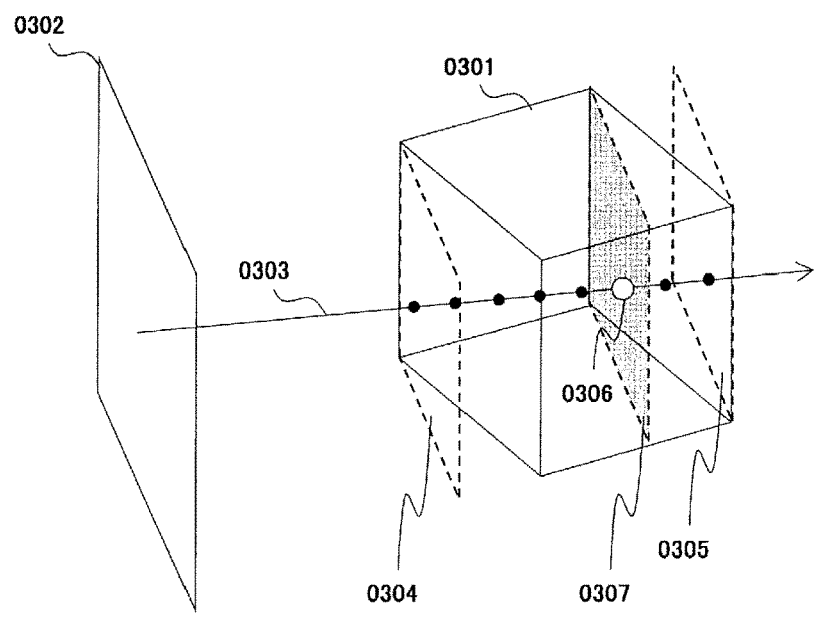
FIG. 26 is a conceptual diagram schematically illustrating a positional relation between luminance volume data or elasticity volume data and a light source.

FIG. 26 is a conceptual diagram schematically illustrating a positional relation between the luminance volume data or the elasticity volume data and the light source. As illustrated in FIG. 26, a light source (parallel light source) 0302 is set in a light source direction 0303 in luminance volume data or elasticity volume data 0301 in the luminance volume data storage unit 0015 by the control unit 0003 and the operation unit 0004. The position of the light source 0302, the light source direction 0303, and light source data in a three-dimensional space are generated by the light source information setting unit 0021.

A plane 0304 indicates a position of a plane in which the volume data (the luminance volume data or the elasticity volume data) 0301 first intersects (comes into contact with) an orthogonal plane in the light source direction 0303 and indicates an illumination calculation start position. A plane 0305 indicates a position of a plane in which the volume data (the luminance volume data or the elasticity volume data) 0301 finally intersects (comes into contact with) an orthogonal plane in the light source direction 0303 and indicates an illumination calculation end position.

The illumination calculation unit 0023 performs illumination calculation on a plane (an orthogonal plane in the light source direction 0303) orthogonal in the light source direction 0303. In FIG. 26, the illumination calculation unit 0023 performs the illumination calculation in a scope from the plane 0304 to the plane 0305. For example, the illumination calculation unit 0023 performs illumination calculation on a plane 0307 in illumination calculation of a sample 0306 located in the light source direction 0303.

Figure 27:
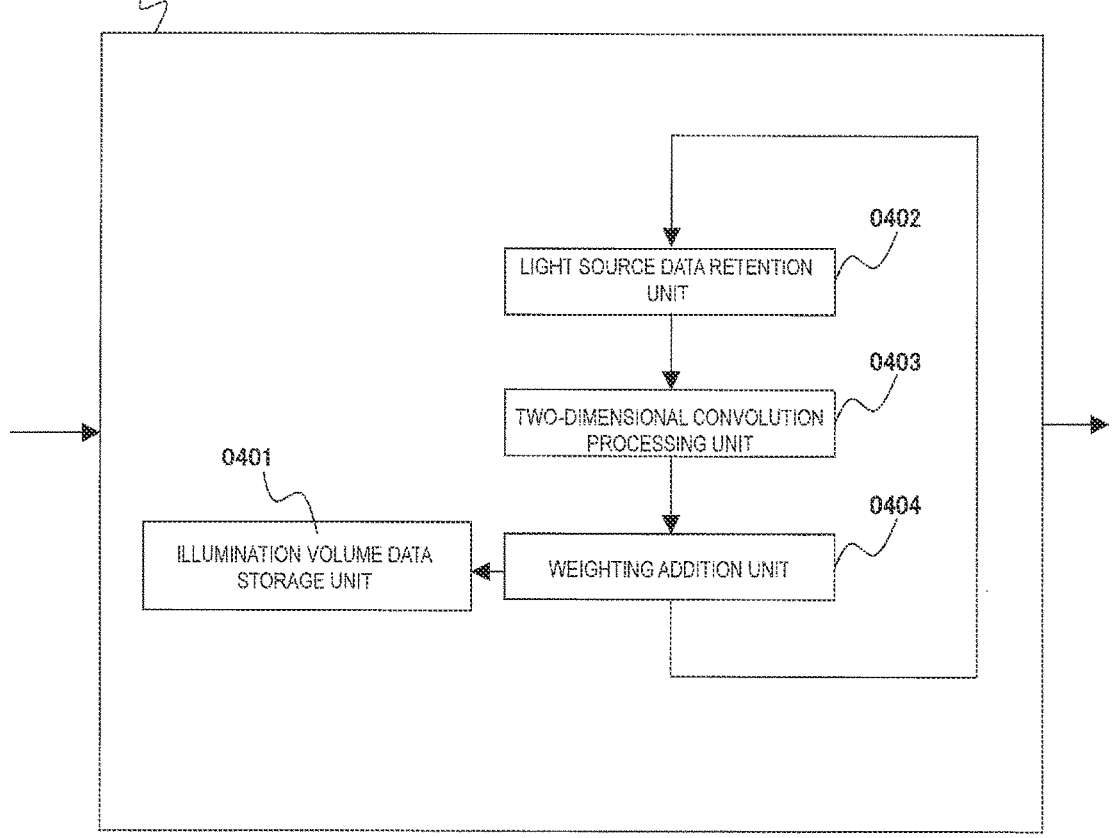
FIG. 27 is a block diagram illustrating an example of the configuration of an illumination calculation unit according to the third embodiment.

Next, an example of the configuration of the illumination calculation unit 0023 will be described with reference to FIG. 27. As illustrated in FIG. 27, the illumination calculation unit 0023 includes an illumination volume data storage unit 0401, a light source data retention unit 0402, a two-dimensional convolution processing unit 0403, and a weighting addition unit 0404. The illumination calculation unit 0023 includes the two-dimensional convolution processing unit 0403 that generates two-dimensional convolution integrated data by performing two-dimensional convolution integration on the light source data and the weighting addition unit 0404 that generates the illumination volume data by performing weighting addition on the light source data and the two-dimensional convolution integrated data based on the weight coefficient which is based on at least one of the luminance value and the elasticity value.

The illumination calculation unit 0023 includes the light source data retention unit 0402 that retains an initial value of the light source data and a result of the weighting addition obtained by the weighting addition unit as input light source data. The illumination calculation unit 0023 generates two-dimensional convolution integrated data by performing two-dimensional convolution integration on the input light source data while switching voxels from the illumination calculation start position to the illumination calculation end position of the luminance volume data, and generates the illumination volume data by performing weighting addition on the input light source data and the two-dimensional convolution integrated data based on the weight coefficient which is based on at least one of the luminance value and the elasticity value.

The light source data retention unit 0402 inputs the light source data generated by the light source information setting unit 0021 and retains the light source data as an initial value. Hereinafter, the light source data retained by the light source data retention unit 0402 is referred to as "input light source data". The two-dimensional convolution processing unit 0403 generates the two-dimensional convolution integrated data by performing the two-dimensional convolution integration on the input light source data (light source data). The two-dimensional convolution integration process indicates convolution integration on a two-dimensional plane and is performed on, for example, the plane 0307.

The weighting addition unit 0404 inputs the two-dimensional convolution integrated data which is an output result of the two-dimensional convolution processing unit 0403 and inputs the input light source data retained by the light source data retention unit 0402. The weighting addition unit 0404 generates the illumination volume data by performing the weighting addition on the input light source data (light source data) and the two-dimensional convolution integrated data based on the weight coefficient. The weight coefficient used by the weighting addition unit 0404 is set as the optical characteristics of the volume data (the luminance volume data or the elasticity volume data) in regard to the light source by the optical characteristic setting unit 0022. Hereinafter, a weighting addition result generated by the weighting addition unit 0404 is referred to as "output illumination data".

The output illumination data is stored at a position according to the coordinates of the voxels of the illumination volume data storage unit 0401. The output illumination data is input to the light source data retention unit 0402 and is stored (retained) as input light source data. That is, the light source data retention unit 0402 retains the initial value of the light source data and the result of the weighting addition by the weighting addition unit 0404 as the input light source data.

Here, the input light source data of the initial value is light source data set by the light source information setting unit 0021, and is input to the light source data retention unit 0402 to be set (retained) before the illumination calculation unit 0023 starts the illumination calculation.

The two-dimensional convolution processing unit 0403 and the weighting addition unit 0404 in the illumination calculation unit 0023 generate the two-dimensional convolution integrated data by performing the two-dimensional convolution integration on the input light source data, while switching the voxels corresponding to coordinates to be referred to from the illumination calculation start position (the plane 0304) to the illumination calculation end position (the plane 0305) of the luminance volume data or the elasticity volume data, and generate the illumination volume data by performing the weighting addition on the input light source data and the two-dimensional convolution integrated data using the weight coefficient, while switching the luminance value or the elasticity value corresponding to the coordinates to be referred to.

Figure 28:
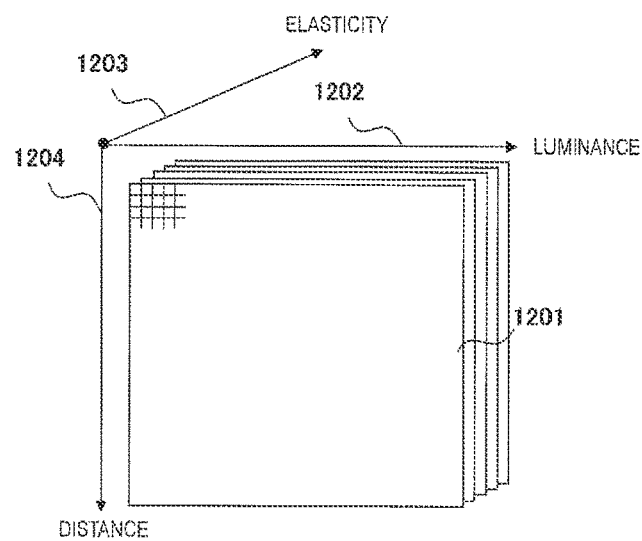
FIG. 28 is a diagram illustrating an example of a luminance elasticity three-dimensional weight coefficient table according to the third embodiment.

Next, a method of setting the weight coefficient used by the weighting addition unit 0404 will be described with reference to FIG. 28. FIG. 28 is a diagram illustrating a weight coefficient table according to the embodiment. As illustrated in FIG. 28, a luminance elasticity three-dimensional weight coefficient table 1201 is used by the weighting addition unit 0404. The luminance elasticity three-dimensional weight coefficient table 1201 is a three-dimensional table which includes the weight coefficients (the weight coefficients based on the luminance value and the elasticity value) set by the control unit 0003 and which is used to refer to the weight coefficients in which a luminance value 1202 of the luminance volume data, an elasticity value (voxel value) 1203 of the elasticity volume data, and a distance 1204 from a body surface (or the surface of a tissue) are stored three-dimensionally as three indexes. That is, the weight coefficients are regulated by the luminance elasticity three-dimensional weight coefficient table 1201 in which the luminance value of the luminance volume data, the elasticity value of the elasticity volume data, and the distance from the surface of a target object are set as indexes. In this case, the optical characteristic setting unit 0022 sets the weight coefficient regulated by the luminance elasticity three-dimensional weight coefficient table 1201. The optical characteristic setting unit 0022 sets the weight coefficients according to the luminance value of the luminance volume data, the elasticity value of the elasticity volume data, and the distance from the surface of a target object. That is, the optical characteristic setting unit 0022 sets the weight coefficients according to at least two voxel values of the plurality of pieces of volume data and the distance from the surface of the target object.

The optical characteristics according to the embodiment are regulated by the weight coefficient set so that a behavior (action) of light is replicated based on the optical characteristics of a tissue and are set by the optical characteristic setting unit 0022. The optical characteristic setting unit 0022 sets the luminance elasticity three-dimensional weight coefficient table 1201 that includes the weight coefficients as the optical characteristics of the luminance volume data and the elasticity volume data. As illustrated in FIG. 28, two weight coefficients a5 and b5 are referred to from the luminance elasticity three-dimensional weight coefficient table 1201 based on the three indexes, the luminance value of the luminance volume data, the elasticity value of the elasticity volume data, and the distance from the surface of a target object. The weight coefficient a5 is a weight coefficient having an influence on (multiplied to) the input light source data and the weight coefficient b5 is a weight coefficient having an influence on (multiplied to) the two-dimensional convolution integrated data. In this case, a behavior of light in the luminance volume data and a behavior of light in the elasticity volume data can be simply set by adjusting the magnitudes of the weight coefficients a5 and b5.

A weighted sum of the two-dimensional convolution integrated data and the input light source data based on the weight coefficients a5 and b5 are output to the illumination volume data storage unit 0401. By setting the sum value of the weight coefficients a5 and b5 to be large, it is possible to set reinforced illumination. By setting the sum value of the weight coefficients a5 and b5 to be small, it is possible to set weak illumination. In the case of ultrasonic data, luminance reflecting acoustic impedance of a tissue can be useful information reflecting the characteristics of a biological tissue. Luminance in ultrasonic data reflects the amplitude of a reflected wave obtained by reflecting a radiated ultrasonic wave from a diffusing body, and thus is normally attenuated with propagation of the ultrasonic wave in a deep portion. Thus, in regard to the ultrasonic data, it is difficult to classify tissues based on only the luminance. Accordingly, by adding a distance from the body surface of a target object (or the surface of a tissue) as an index, it is possible to classify tissues in regard to the ultrasonic data.

For example, when a target object is a breast containing a tumor part and an ultrasonic wave arriving at the tumor via a fatty layer is considered, it is known that luminance is relatively high in a mammary gland interposed between the fatty layer and the tumor and luminance of the ultrasonic wave is low in the tumor and the fatty layer. Accordingly, when only the luminance is used as an index, it is difficult to distinguish the tumor from the fatty layer in some cases. Accordingly, a distance from a body surface of a target object is added as an index. Further, an elasticity value is low in a tumor part and an elasticity value is considered to be an index of a malignant tumor. However, a hard region is measured artificially due to pressure against to an object in measurement of an elasticity value in some cases. For example, since no strain occurs in a region to which pressures are not transferred in a deep part of an object, a hard region is determined to be present artificially in some cases. Thus, when only elasticity is used as an index, it is difficult to distinguish a tumor in some cases. Accordingly, a distance from the body surface of a target object is added as an index. By setting the weight coefficients a5 and b5 of the luminance elasticity three-dimensional weight coefficient table 1201 for which volume data satisfying conditions that a luminance value is low, an elasticity value is low, and a distance from a body surface is equal to or less than a constant value are volume data corresponding to a tumor, it is possible to reflect optical characteristics of a tumor part. That is, by setting the weight coefficients a5 and b5 using the luminance elasticity three-dimensional weight coefficient table 1201 which are based on three indexes of luminance, elasticity, and a distance, a behavior of light can be expressed so that a tissue is distinguished. In a volume rendering method, it is possible to obtain an image (three-dimensional image) of which reality is improved. For example, an optical effect of a tumor is not given to an artificial hard region (a region mistaken for a tumor).

The illumination calculation unit 0023 repeatedly performs the foregoing illumination calculation process while switching coordinates to be referred to by the weighting addition unit 0404 from the illumination calculation start position (the plane 0304) to the illumination calculation end position (the plane 0305) and switching the corresponding luminance and elasticity values. The illumination calculation unit 0023 selects one piece of volume data from two pieces of volume data (the luminance volume data and the elasticity volume data) for respective coordinates of the volume data, calculates illumination of a position according to the coordinates based on the optical characteristics (or the weight coefficients) of the selected volume data, and generates the illumination volume data based on the calculated illumination.

The illumination calculation unit 0023 performs the calculation up to the illumination calculation end position to generate illumination volume data in which all of the illumination corresponding to voxel coordinates on the volume data are calculated, and then stores the illumination volume data in the illumination volume data storage unit 0401.

The behavior characteristics of light differ depending on a wavelength of a light source according to the law of nature. Accordingly, when the reality is further improved in conformity to the law of nature, the illumination calculation is performed for each wavelength of the light source. In this case, the weight coefficients differ for each wavelength of the light source.

The light source information setting unit 0021 sets the light source data according to a plurality of wavelengths of the light source. The optical characteristic setting unit 0022 sets the weight coefficients for each of the plurality of wavelengths.

The illumination calculation unit 0023 performs the illumination calculation for each of the plurality of wavelengths of the light source 0302 to generate the illumination volume data. For example, when the light source 0302 is 7 colors of the visible light, the illumination calculation unit 0023 sets 7 kinds of weight coefficients (or two-dimensional weight coefficient tables) and generates 7 kinds of pieces of illumination volume data. When the light source 0302 is the three primary colors of additive color mixture, the illumination calculation unit 0023 sets three sets of weight coefficients (or three kinds of two-dimensional weight coefficient tables) corresponding to wavelengths of the R, G, and B components and generates three kinds of pieces of illumination volume data. That is, the light source information setting unit 0021 sets the light source data according to the plurality of wavelengths of the light source, the optical characteristic setting unit 0022 sets the weight coefficient for each of the plurality of wavelengths, and the illumination calculation unit 0023 generates the illumination volume data for each of the plurality of wavelengths.

In the embodiment, a case will be described in which the light source 0302 is the three primary colors of additive color mixture, three sets of weight coefficients (or three kinds of two-dimensional weight coefficient tables) are set, and three kinds of pieces of illumination volume data are generated. An initial value of the light source data is set for each wavelength of the light source 0302. That is, the same number of initial values of the light source data as the number of effective wavelengths is set by the light source information setting unit 0021. Accordingly, in the embodiment, three kinds of pieces of light source data corresponding to the wavelengths of the R, G, and B components are set and are each retained as independent input light source data by the light source data retention unit 0402. The initial values of the three kinds of pieces of light source data may be initial values selected via the operation unit 0004 by an operator or may be initial values set using an image.

The illumination calculation unit 0023 calculates the illumination disposed on the luminance volume data based on the three kinds of light source data and three kinds of optical characteristics (the weight coefficient or two-dimensional weight coefficient table) and generates three kinds of pieces of illumination volume data.

The projection processing unit 0018 generates a three-dimensional image based on opacity referred to by the illumination of the illumination volume data and the voxel value of the volume data (the luminance value of the luminance volume data or the elasticity value of the elasticity volume data). When the light source 0302 is the three primary colors, the projection processing unit 0018 generates the three-dimensional image from the three kinds of pieces of illumination volume data generated by the illumination calculation unit 0023, the luminance volume data stored in the luminance volume data storage unit 0015, and the elasticity volume data stored in the elasticity volume data storage unit 1035. A projection process in the projection processing unit 0018 is performed based on illumination (voxel value), opacity $\alpha[i]$, and gradient values $S[i]$ in illumination volume data $L\_r[k]$, $L\_g[k]$, and $L\_b[k]$ of the respective wavelengths (the R, G, and B components), as shown in equations (7) to (9) below, to generate the three-dimensional image. That is, the three-dimensional image is generated by multiplying voxel values in illumination volume data $L\_r[k]$, $L\_g[k]$, and $L\_b[k]$ of the respective wavelengths by opacity terms obtained by opacity $\alpha[i]$ and values of gradient values $S[i]$ and performing summation in a visual line direction. In the equations, "k" indicates voxel coordinates in the visual line direction. The visual line direction is set as a direction in which an ultrasonic image is observed via the control unit 0003 by the operation unit 0004.

Here, the opacity $\alpha[i]$ and the gradient value $S[i]$ are preferably set from the opacity referred to by either of the luminance volume data or the elasticity volume data and the gradient value of either of the luminance gradient volume data or the elasticity gradient volume data which are selected based on a threshold value of at least one of the luminance value and the elasticity value. The opacity $\alpha[i]$ and the gradient value $S[i]$ are set for each voxel. For example, based on the threshold value of the luminance value in an i-th voxel in the visual line direction, the opacity $\alpha[i]$ referred to by the luminance volume data and the gradient value $S[i]$ of the luminance gradient volume data are set. Further, based on the threshold value of the elasticity value in an i-th voxel in the visual line direction, the opacity $\alpha[i]$ referred to by the elasticity volume data and the gradient value $S[i]$ of the elasticity gradient volume data are set.

$$OUT\_R[K]=\Sigma^{k=0:k}((L\_r[k]\cdot S[k])\cdot\alpha[k]\cdot\Pi^{m=0:k-1}(1-\alpha[m])) \quad (7)$$

$$OUT\_G[K]=\Sigma^{k=0:k}((L\_g[k]\cdot S[k])\cdot\alpha[k]\cdot\Pi^{m=0:k-1}(1-\alpha[m])) \quad (8)$$

$$OUT\_B[K]=\Sigma^{k=0:k}((L\_b[k]\cdot S[k])\cdot\alpha[k]\cdot\Pi^{m=0:k-1}(1-\alpha[m])) \quad (9)$$

The three-dimensional image generated by the three-dimensional image processing unit 0016 is disposed on the same screen as an arbitrary cross-sectional image by the image combination unit 0017 and is displayed by the display unit 0009.

In the embodiment, the ultrasonic diagnostic device 0001 includes the gradient calculation units 0019 and 1039, but may also exclude the gradient calculation units 0019 and 1039. In this case, the terms of gradient values $S[k]$ in equations (7) to (9) are excluded from equations (7) to (9) (or are treated as "1.0") so that these terms do not contribute to the three-dimensional image to be generated.

Figure 29:
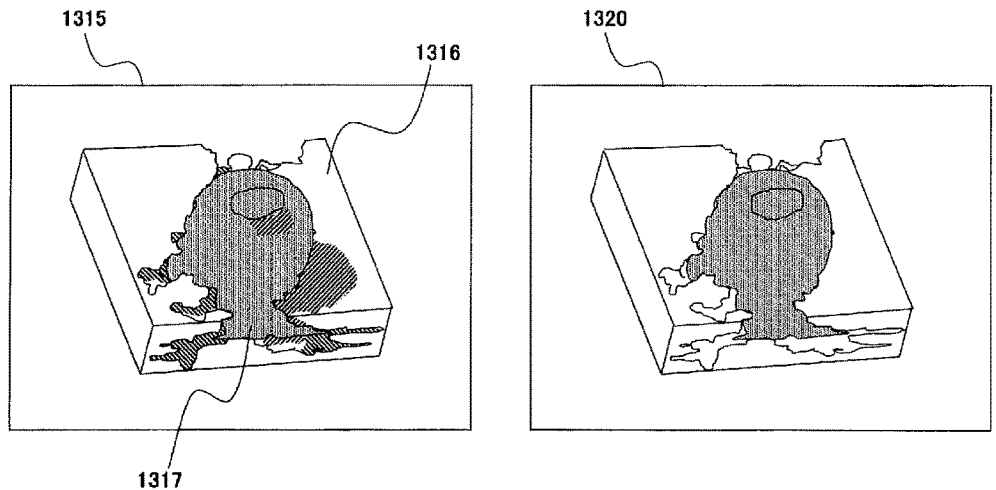
FIG. 29 is a diagram for describing characteristics of a three-dimensional image according to the third embodiment.

Next, the characteristics of the three-dimensional image according to the embodiment will be described with reference to FIG. 29. A three-dimensional image 1315 in FIG. 29 is a three-dimensional image constructed according to a method according to the embodiment. As illustrated in FIG. 29, an optical effect of a normal tissue is given to a normal tissue part 1316 on the three-dimensional image 1315 and an optical effect of a tumor is given to a tumor 1317. Thus, in the volume rendering method, it is possible to obtain a natural image of which reality is improved. A three-dimensional image 1320 is an example of a general three-dimensional image in which the method according to the embodiment is not used. When the three-dimensional image 1311 generated using the method according to the embodiment is compared to the three-dimensional image 1320, the three-dimensional image 1311 can be known to be a stereoscopic and realistic three-dimensional image compared to the three-dimensional image 1320. Accordingly, by using the method according to the embodiment, it is possible to obtain a natural image of which reality is improved in a volume rendering method.

Figure 30:
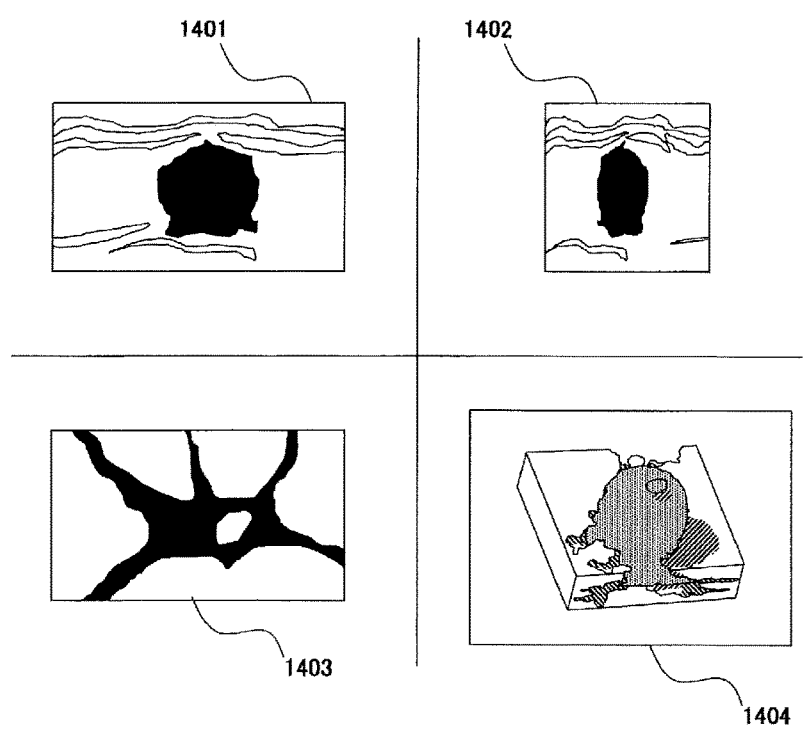
FIG. 30 is a diagram illustrating display examples according to the third embodiment.

FIG. 30 is a diagram illustrating a display example of the display unit 0009 according to the embodiment. As illustrated in FIG. 30, the display unit 0009 displays three orthogonal cross-sectional surfaces 1401, 1402, and 1403 of which planes are orthogonal to each other and a three-dimensional image 1404. The three-dimensional image 1404 generated by the three-dimensional image processing unit 0016 is disposed on the same screen as the three orthogonal cross-sectional surfaces (or arbitrary cross-sectional images) 1401, 1402, and 1403 by the image combination unit 0017 to be displayed. Since the three-dimensional image 1404 can be observed with reference to the orthogonal cross-sectional surfaces (or the arbitrary cross-sectional images) 1401, 1402, and 1403, it is possible to improve inspection precision and efficiency.

Fourth Embodiment

Figure 31:
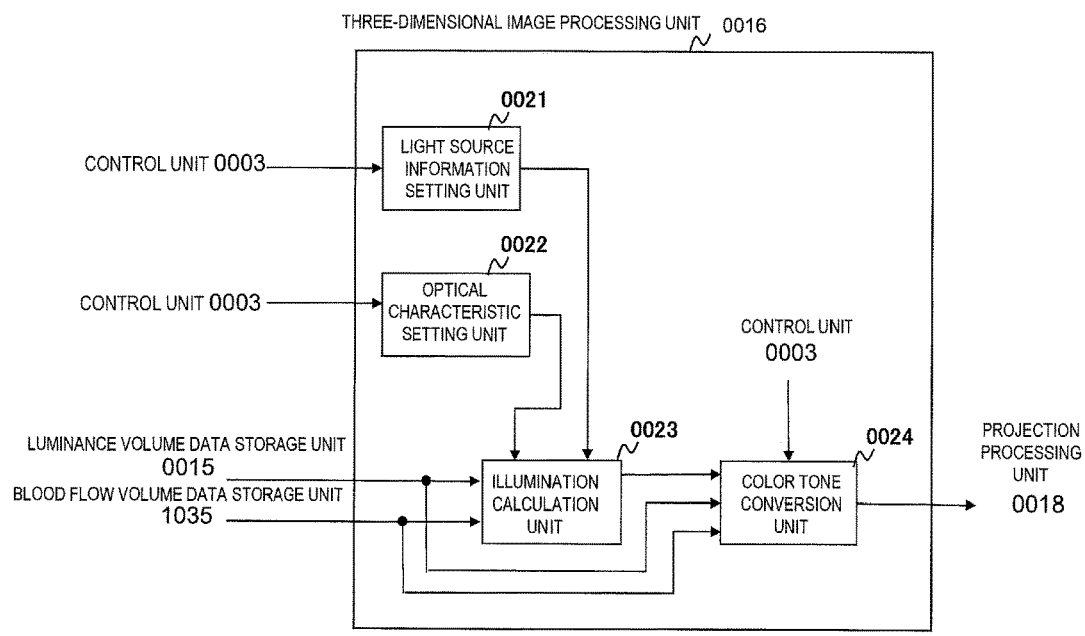
FIG. 31 is a block diagram illustrating an example of a three-dimensional image processing unit according to a fourth embodiment.

A fourth embodiment is a modification example of the second embodiment. Hereinafter, an ultrasonic diagnostic device 0001 according to the fourth embodiment will be described mainly focusing on differences from the second embodiment with reference to the drawings. FIG. 31 is a block diagram illustrating an example of the three-dimensional image processing unit 0016 which is characteristics of the embodiment. As illustrated in FIG. 31, the three-dimensional image processing unit 0016 corresponds to the three-dimensional image processing unit 0016 in the ultrasonic diagnostic device 0001 according to the second embodiment in FIG. 15.

As illustrated in FIG. 31, the three-dimensional image processing unit 0016 includes a color tone conversion unit 0024 in addition to a light source information setting unit 0021, an optical characteristic setting unit 0022, and an illumination calculation unit 0023. The color tone conversion unit 0024 converts a color tone of the illumination volume data based on at least one of the luminance volume data, the blood flow volume data (including blood flow rate volume data, blood flow amplitude volume data, and blood flow dispersion volume data), and the elasticity volume data. The blood flow dispersion volume data includes blood flow rate dispersion volume data and blood flow amplitude dispersion volume data. In the fourth embodiment, the color tone conversion unit 0024 converts the color tone of the illumination volume data based on at least one of the luminance volume data, the blood flow rate volume data, the blood flow amplitude volume data, and the blood flow dispersion volume data. The color tone conversion unit 0024 refers to the luminance volume data from the luminance volume data storage unit 0015. The color tone conversion unit 0024 refers to at least one of blood flow volume data (blood flow rate volume data) regarding a blood flow rate in the blood flow data, blood flow volume data (blood flow amplitude volume data) regarding a blood flow amplitude in the blood flow data, and blood flow volume data (blood flow dispersion volume data) regarding a blood flow rate dispersion in the blood flow data from the blood flow volume data storage unit 0035, performs the color tone conversion on the illumination volume data output from the illumination calculation unit 0023, and outputs the processed illumination volume data.

The illumination calculation unit 0023 performs the illumination calculation for each of the plurality of wavelengths of the light source 0302 to generate the illumination volume data. In this case, the color tone conversion unit 0024 may perform the color tone conversion on the illumination volume data for each of the plurality of wavelengths of the light source 0302 by converting the value of the illumination volume data generated for each of the plurality of wavelengths of the light source 0302 and output the processed illumination volume data. For example, when the light source 0302 is retained with the three primary colors of additive color mixture (that is, the RGB color system), three pieces of illumination volume data of R (red), G (green), and B (blue) components can be obtained by the illumination calculation unit 0023. Thus, the color tone conversion unit 0024 performs the color tone conversion by converting the value of the illumination volume data with reference to at least one of the luminance volume data, the blood flow rate volume data, the blood flow amplitude volume data, and the blood flow dispersion volume data. The value of the illumination volume data is converted into a predetermined value through exchange (including replacement) of the value of each component (RGB) or addition and subtraction or multiplication and division of a predetermined value of a specific component (component arbitrarily selected from RGB) to perform the color tone conversion.

Next, a case will be described in which the color tone conversion unit 0024 performs the color tone conversion on the illumination volume data based on at least one of the luminance volume data, the blood flow rate volume data, and the blood flow amplitude volume data. The color tone conversion unit 0024 inputs three pieces of illumination volume data of the R, G, and B components from the illumination calculation unit 0023, inputs the luminance volume data from the luminance volume data storage unit 0015, and inputs the blood flow rate volume data and the blood flow amplitude volume data from the blood flow volume data storage unit 0035. The color tone conversion unit 0024 inputs a predetermined threshold value from the control unit 0003 and determines whether the illumination at the respective coordinates in the illumination volume data indicates a blood flow or a tissue, as in the illumination calculation unit 0023. For example, the color tone conversion unit 0024 compares the luminance value (voxel value) of the luminance volume data to the luminance threshold value $c_1$. When the luminance value (voxel value) of the luminance volume data exceeds the luminance threshold value $c_1$, the color tone conversion unit 0024 determines that the illumination indicates a tissue. When the luminance value (voxel value) of the luminance volume data is less than the luminance threshold value $c_1$, the color tone conversion unit 0024 determines that the illumination indicates the blood flow. The color tone conversion unit 0024 compares the blood flow amplitude value (voxel value) of the blood flow amplitude volume data to the blood flow amplitude threshold value $c_2$. When the blood flow amplitude value (voxel value) of the blood flow amplitude volume data exceeds the blood flow amplitude threshold value $c_2$, the color tone conversion unit 0024 determines that the illumination indicates the blood flow. When the blood flow amplitude value (voxel value) of the blood flow amplitude volume data is less than the blood flow amplitude threshold value $c_2$, the color tone conversion unit 0024 determines that the illumination indicates a tissue. The color tone conversion unit 0024 compares the blood flow rate value (voxel value) of the blood flow rate volume data to the blood flow rate threshold value $c_3$. When the blood flow rate value (voxel value) of the blood flow rate volume data exceeds the blood flow rate threshold value $c_3$, the color tone conversion unit 0024 determines that the illumination indicates the blood flow. When the blood flow rate value (voxel value) of the blood flow rate volume data is less than the blood flow rate threshold value $c_3$, the color tone conversion unit 0024 determines that the illumination indicates a tissue. The color tone conversion unit 0024 may combine the threshold values $c_1$, $c_2$, and $c_3$ to determine a blood flow and a tissue.

The color tone conversion unit 0024 converts the color tone by exchanging the values of the illumination of at least two pieces of illumination volume data among a plurality of pieces of illumination volume data. For example, when predetermined coordinates are determined to be the blood flow, the color tone conversion unit 0024 refers to the blood flow rate volume data at the coordinates. When a blood flow rate value (voxel value) is negative, the color tone conversion is performed by exchanging an illumination value (voxel value) of the illumination volume data of the R component and an illumination value (voxel value) of the illumination volume data of the B component. In this way, by exchanging the components according to a direction of the blood flow (positive or negative blood flow rate value), it is possible to give blood flow direction information while maintaining the optical effect calculated by the illumination calculation unit 0023. It is possible to obtain a three-dimensional image of which visibility is excellent and reality and diagnosability are improved.

Figure 32:
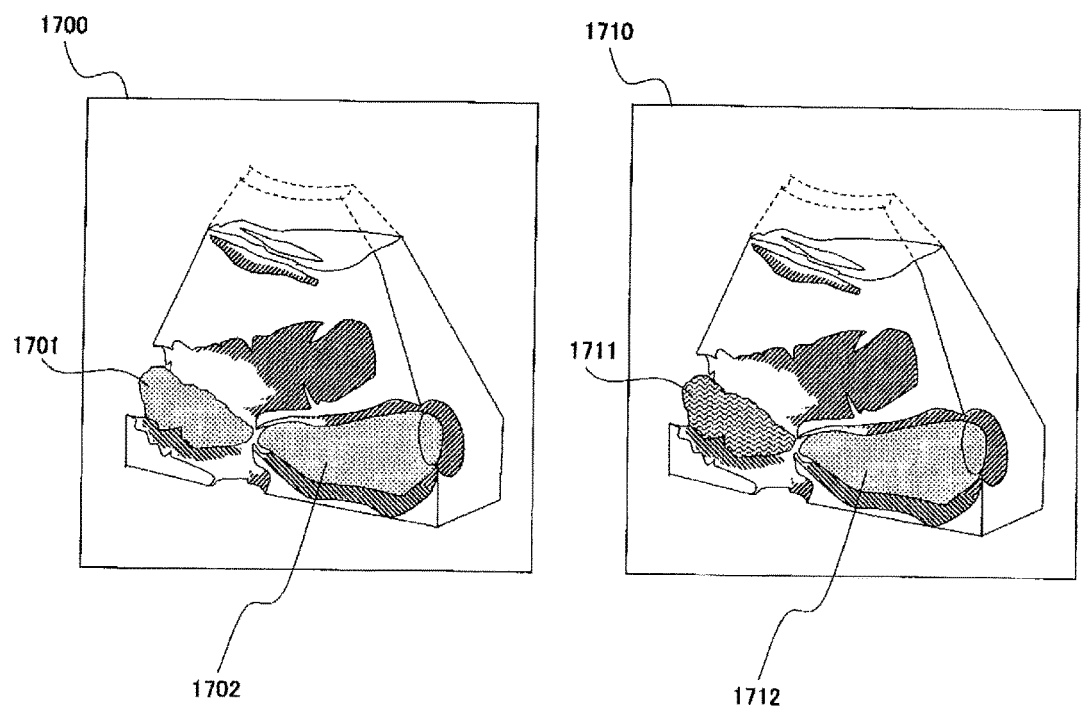
FIG. 32 is a schematic diagram illustrating effects of exchange of values of components (RGB).

FIG. 32 is a schematic diagram illustrating an effect of the exchange of the value of each component (RGB) by the color tone conversion unit 0024. A three-dimensional image 1700 in FIG. 32 is a three-dimensional image according to the second embodiment and a three-dimensional image 1710 is a three-dimensional image according to the fourth embodiment. When a blood flow 1701 in the three-dimensional image 1700 is in a negative opposite direction to a blood flow 1702, the color tone conversion is performed by the color tone conversion unit 0024 in the fourth embodiment. For example, a blood flow 1712 is displayed with a red color (R component) and a blood flow 1711 is displayed with a blue color (B component). That is, when the color tone conversion unit 0024 performs the color tone conversion, the blood flow 1711 and the blood flow 1712 are displayed with different colors according to the direction of the blood flow (positive or negative blood flow rate value), and thus visibility can be excellent and the diagnosability can be improved.

The color tone conversion unit 0024 performs the color tone conversion on the value of the illumination of at least one piece of illumination volume data among the plurality of pieces of illumination volume data by performing at least one of addition, subtraction, multiplication, and division of a predetermined value. For example, when predetermined coordinates are determined to indicate a blood flow, the color tone conversion unit 0024 refers to the blood flow dispersion volume data at the coordinates. When the blood flow rate dispersion value exceeds a predetermined threshold value, the illumination value (voxel value) of the illumination volume data of the G component is multiplied by a coefficient proportional to the magnitude of the blood flow rate dispersion value (voxel value) of the blood flow dispersion volume data. In this way, by multiplying the specific component (G component) by the predetermined coefficient according to the blood flow rate dispersion value for emphasis, it is possible to provide dispersion information of the blood flow rate, while maintaining the optical effect calculated by the illumination calculation unit 0023. It is possible to obtain a three-dimensional image of which visibility is excellent and reality and diagnosability are improved.

Figure 33:
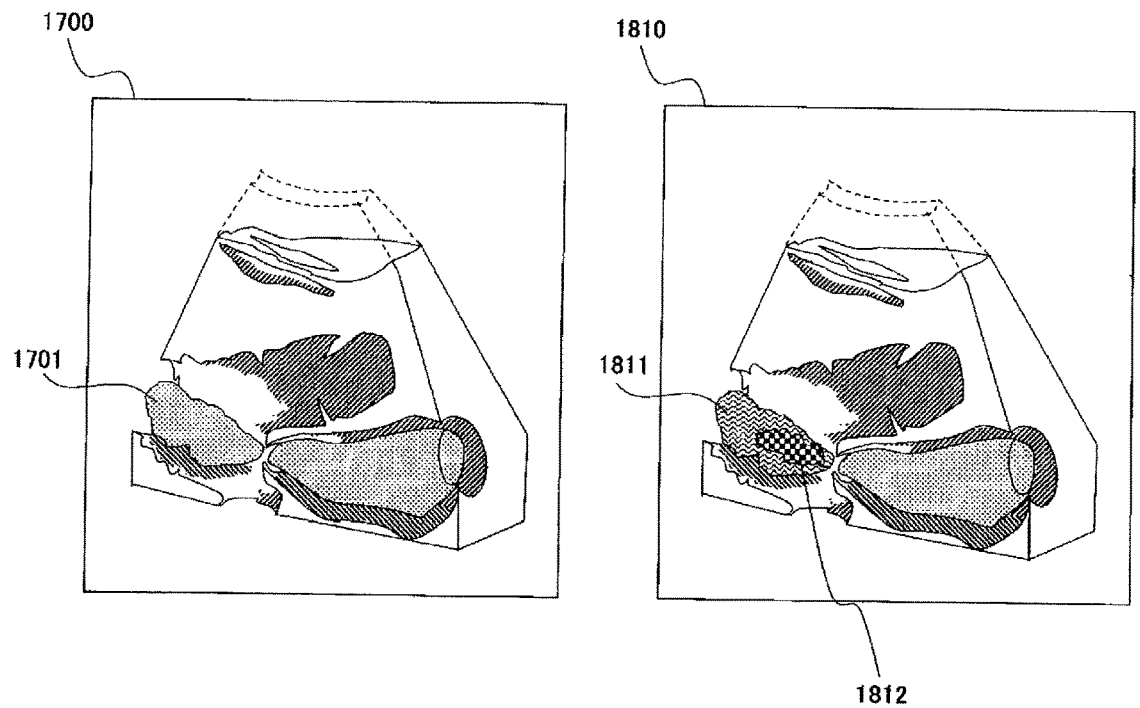
FIG. 33 is a schematic diagram illustrating effects of multiplication of the components by coefficients.

FIG. 33 is a schematic diagram illustrating an effect obtained by multiplying the component by the coefficient by the color tone conversion unit 0024. The three-dimensional image 1700 in FIG. 33 is a three-dimensional image according to the second embodiment and a three-dimensional image 1810 is a three-dimensional image according to the fourth embodiment. When blood flow rate dispersion values of front parts of blood flows 1701 and 1811 are considerably high and exceed a predetermined threshold value, the color tone conversion is performed by the color tone conversion unit 0024 in the fourth embodiment. For example, a blood flow 1812 to which the dispersion information of the blood flow rate is reflected can be displayed on the blood flow 1811 of the three-dimensional image 1810. That is, when the color tone conversion unit 0024 performs the color tone conversion, the blood flow 1811 and the blood flow 1812 are displayed with different colors according to the blood flow rate dispersion value, and thus visibility can be excellent and the diagnosability can be improved.

Fifth Embodiment

Figure 34:
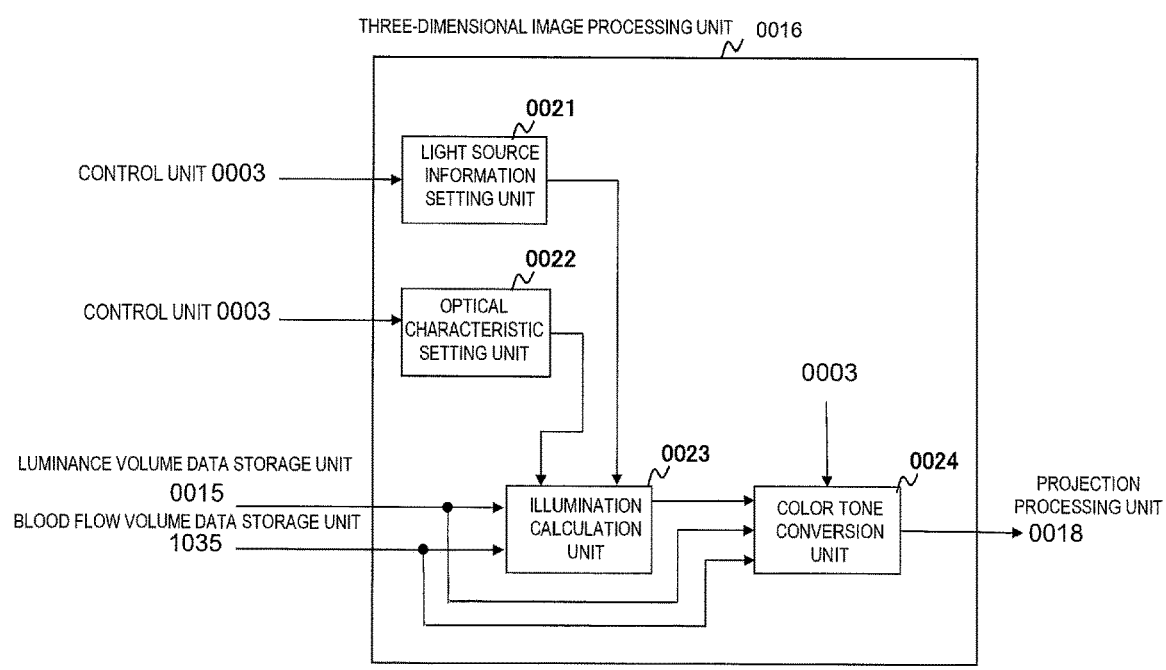
FIG. 34 is a block diagram illustrating an example of a three-dimensional image processing unit according to a fifth embodiment.

A fifth embodiment is a modification example of the third embodiment. Hereinafter, an ultrasonic diagnostic device 0001 according to the fifth embodiment of the present invention will be described mainly focusing on differences from the third embodiment with reference to the drawings. FIG. 34 is a block diagram illustrating an example of the three-dimensional image processing unit 0016 which is characteristics of the embodiment. As illustrated in FIG. 34, the three-dimensional image processing unit 0016 corresponds to the three-dimensional image processing unit 0016 in the ultrasonic diagnostic device 0001 according to the third embodiment in FIG. 24.

As illustrated in FIG. 34, the three-dimensional image processing unit 0016 includes a color tone conversion unit 0024 in addition to a light source information setting unit 0021, an optical characteristic setting unit 0022, and an illumination calculation unit 0023. The color tone conversion unit 0024 converts a color tone of the illumination volume data based on at least one of the luminance volume data, the blood flow volume data (including blood flow rate volume data, blood flow amplitude volume data, and blood flow dispersion volume data), and the elasticity volume data. The blood flow dispersion volume data includes blood flow rate dispersion volume data and blood flow amplitude dispersion volume data. In the fifth embodiment, the color tone conversion unit 0024 refers to the luminance volume data from the luminance volume data storage unit 0015. The color tone conversion unit 0024 refers to the elasticity volume data from the elasticity volume data storage unit 1035. The color tone conversion unit 0024 performs the color tone conversion on the illumination volume data output from the illumination calculation unit 0023 using at least one of the luminance volume data and the elasticity volume data and outputs the processed illumination volume data.

The illumination calculation unit 0023 performs the illumination calculation for each of the plurality of wavelengths of the light source 0302 to generate the illumination volume data. In this case, the color tone conversion unit 0024 may perform the color tone conversion on the illumination volume data for each of the plurality of wavelengths of the light source 0302 by converting the value of the illumination volume data generated for each of the plurality of wavelengths of the light source 0302 and output the processed illumination volume data. For example, when the light source 0302 is retained with the three primary colors of additive color mixture (that is, the RGB color system), three pieces of illumination volume data of R (red), G (green), and B (blue) components can be obtained by the illumination calculation unit 0023. Thus, the color tone conversion unit 0024 performs the color tone conversion by converting the value of the illumination volume data with reference to at least one of the luminance volume data and the elasticity volume data. The value of the illumination volume data is converted into a predetermined value through exchange (including replacement) of the value of each component (RGB) or addition and subtraction or multiplication and division of a predetermined value of a specific component (component arbitrarily selected from RGB) to perform the color tone conversion.

Next, a case will be described in which the color tone conversion unit 0024 performs the color tone conversion on the illumination volume data based on the luminance volume data and the elasticity volume data. The color tone conversion unit 0024 inputs three pieces of illumination volume data of the R, G, and B components from the illumination calculation unit 0023, inputs the luminance volume data from the luminance volume data storage unit 0015, and inputs the elasticity volume data from the elasticity volume data storage unit 1035. The color tone conversion unit 0024 inputs a predetermined threshold value from the control unit 0003 and determines whether the illumination at the respective coordinates in the illumination volume data indicates a hard tissue, as in the illumination calculation unit 0023. For example, the color tone conversion unit 0024 compares an elasticity value (voxel value) of the elasticity volume data to the elasticity threshold value d2 to determine whether a tissue is a hard tissue. When the color tone conversion unit 0024 determines that the elasticity value (voxel value) indicates the hard tissue, the color tone conversion unit 0024 can also further classify the hardness of the tissue based on the elasticity threshold value d3 different from the elasticity threshold value d2.

For example, when the corresponding coordinates indicate a region having specific hardness discriminated by the elasticity threshold value d3, the color tone conversion unit 0024 performs the color tone conversion by exchanging an illumination value (voxel value) of the illumination volume data of the R component and an illumination value (voxel value) of the illumination volume data of the B component at the corresponding coordinates. In this way, by exchanging the components according to the hardness of a tissue (whether the elasticity value exceeds the elasticity threshold value), it is possible to give tissue hardness information while maintaining the optical effect calculated by the illumination calculation unit 0023. It is possible to obtain a three-dimensional image of which visibility is excellent and reality and diagnosability are improved.

Figure 35:
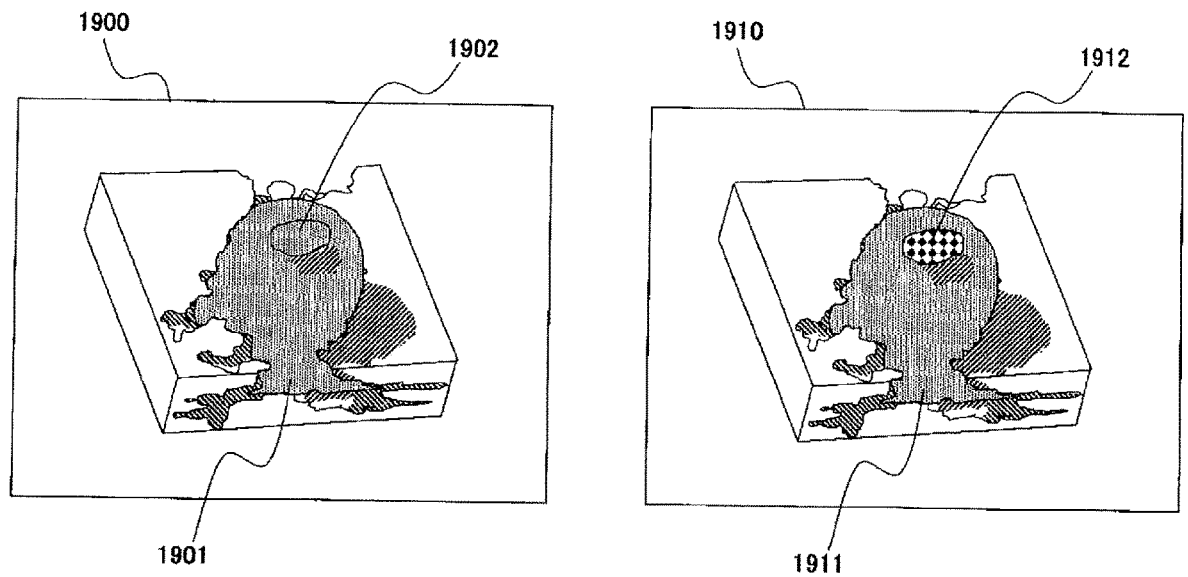
FIG. 35 is a schematic diagram illustrating effects of exchange of values of components (RGB).

FIG. 35 is a schematic diagram illustrating an effect of the exchange of the value of each component (RGB) by the color tone conversion unit 0024. A three-dimensional image 1900 in FIG. 35 is a three-dimensional image according to the third embodiment and a three-dimensional image 1910 is a three-dimensional image according to the fifth embodiment. When a tumor tissue 1902 in a tumor tissue 1901 of the three-dimensional image 1900 is particularly soft (when the elasticity value of the tumor tissue 1902 exceeds a predetermined elasticity threshold value or the elasticity value of the tumor tissue 1902 does not exceed the predetermined threshold value), the color tone conversion is performed by the color tone conversion unit 0024 in the fifth embodiment. For example, as illustrated in the three-dimensional image 1910, a tumor tissue 1911 is displayed with a blue color (B component) and a particular soft tumor tissue 1912 is displayed with a red color (R component). Further, when the tumor tissue 1902 in the tumor tissue 1901 of the three-dimensional image 1900 is particularly hard (when the elasticity value of the tumor tissue 1902 does not exceed the predetermined elasticity threshold value or the elasticity value of the tumor tissue 1902 exceeds the predetermined threshold value), the color tone conversion is performed by the color tone conversion unit 0024 in the fifth embodiment. For example, as illustrated in the three-dimensional image 1910, the tumor tissue 1911 is displayed with a blue color (B component) and the particularly hard tumor tissue 1912 is displayed with a red color (R component). That is, when the color tone conversion unit 0024 performs the color tone conversion, the soft tissue is displayed with a different color from the hard tissue according to the hardness of the tissue, and thus visibility can be excellent and the diagnosability can be improved.

The color tone conversion unit 0024 performs the color tone conversion on the value of the illumination of at least one piece of illumination volume data among the plurality of pieces of illumination volume data by performing at least one of addition, subtraction, multiplication, and division of a predetermined value. For example, when predetermined coordinates are determined to indicate a tissue, the color tone conversion unit 0024 refers to the elasticity volume data at the corresponding coordinates. When the elasticity value exceeds (or does not exceed) a predetermined threshold value, the illumination value (voxel value) of the illumination volume data of the G component is multiplied by a coefficient proportional to the magnitude of the elasticity value (voxel value) of the elasticity volume data. In this way, by multiplying the specific component (G component) according to the elasticity value for emphasis, it is possible to provide tissue elasticity information, while maintaining the optical effect calculated by the illumination calculation unit 0023. It is possible to obtain a three-dimensional image of which visibility is excellent and reality and diagnosability are improved.

The embodiments have been described, but the present invention is not limited thereto and can be altered and modified within the scope described in the claims.

Figure 36:
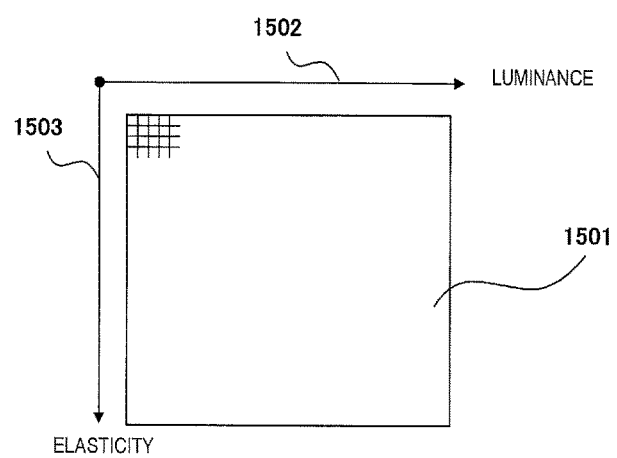
FIG. 36 is a diagram illustrating a modification example of a luminance elasticity two-dimensional weight coefficient table according to the third embodiment.

FIG. 36 is a diagram illustrating a modification example of the weight coefficient table according to the embodiment. As illustrated in FIG. 36, instead of the luminance elasticity three-dimensional weight coefficient table 1201, a luminance elasticity two-dimensional weight coefficient table 1501 may be used in the weighting addition unit 0404. The luminance elasticity two-dimensional weight coefficient table 1501 is a two-dimensional table which includes weight coefficients (weight coefficients based on a luminance value and an elasticity value) set by the control unit 0003 and is used to refer to the weight coefficients in which a luminance value 1502 of the luminance volume data and an elasticity value 1503 of the elasticity volume data are stored as two indexes two-dimensionally. That is, the weight coefficients are regulated by the luminance elasticity two-dimensional weight coefficient table 1501 in which the luminance value of the luminance volume data and the elasticity value of the elasticity volume data are set as indexes. In this case, the optical characteristic setting unit 0022 sets the weight coefficients regulated by the luminance elasticity two-dimensional weight coefficient table 1501. The optical characteristic setting unit 0022 sets the weight coefficients according to the luminance value of the luminance volume data and the elasticity value of the elasticity volume data. That is, the optical characteristic setting unit 0022 sets the weight coefficients according to at least two voxel values of the plurality of pieces of volume data.

The optical characteristics in the embodiment are regulated by the weight coefficients set so that a behavior (action) of light is replicated based on the optical characteristics of a tissue, and are set by the optical characteristic setting unit 0022. The optical characteristic setting unit 0022 sets the luminance elasticity two-dimensional weight coefficient table 1501 which includes the weight coefficients as the optical characteristics of the luminance volume data and the elasticity volume data. As illustrated in FIG. 36, two weight coefficients a6 and b6 are referred to from the luminance elasticity two-dimensional weight coefficient table 1501 based on the two indexes, the luminance value of the luminance volume data and the elasticity value of the elasticity volume data. The weight coefficient a6 is a weight coefficient having an influence on (multiplied to) the input light source data and the weight coefficient b6 is a weight coefficient having an influence on (multiplied to) the two-dimensional convolution integrated data. In this case, a behavior of light in the luminance volume data and a behavior of light in the elasticity volume data can be simply set by adjusting the magnitudes of the weight coefficients a6 and b6.

Figure 37:
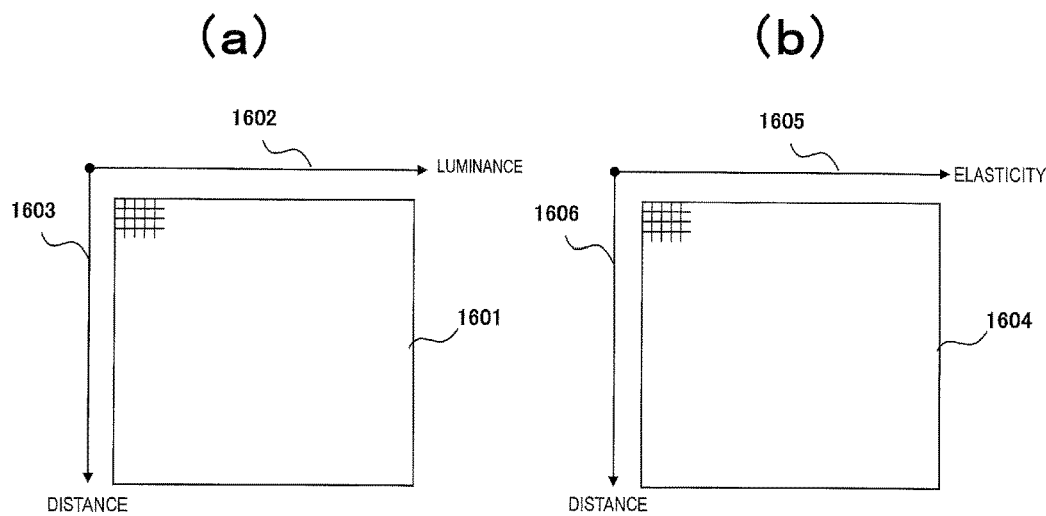
FIG. 37 is a diagram illustrating examples of a luminance two-dimensional weight coefficient table and an elasticity second-order weight coefficient table according to the third embodiment.

FIG. 37 is a diagram illustrating a modification example of the weight coefficient table according to the embodiment. As illustrated in FIG. 37(a), a luminance two-dimensional weight coefficient table 1601 is a two-dimensional table which includes a weight coefficient (a weight coefficient based on a luminance value) set by the control unit 0003 and is used to refer to the weight coefficients in which a luminance value 1602 of the luminance volume data and a distance 1603 from a body surface (or the surface of a tissue) are stored as two indexes two-dimensionally. As illustrated in FIG. 37(b), an elasticity two-dimensional weight coefficient table 1604 is a two-dimensional table which includes a weight coefficient (a weight coefficient based on an elasticity value) set by the control unit 0003 and is used to refer to the weight coefficients in which an elasticity value 1605 of the elasticity volume data and a distance 1606 from a body surface (or the surface of a tissue) are stored as two indexes two-dimensionally. That is, the weight coefficients are regulated by the luminance two-dimensional weight coefficient table 1601 in which the luminance value of the luminance volume data and the distance from the surface of a target object are set as indexes and the elasticity two-dimensional weight coefficient table 1604 in which the elasticity value of the elasticity volume data and the distance from the surface of a target object are set as indexes. In this case, the optical characteristic setting unit 0022 sets the weight coefficients regulated by the luminance two-dimensional weight coefficient table 1601 and the elasticity two-dimensional weight coefficient table 1604. The optical characteristic setting unit 0022 sets the weight coefficients according to the luminance value of the luminance volume data and the distance from the surface of a target object. The optical characteristic setting unit 0022 sets the weight coefficients according to the elasticity value of the elasticity volume data and the distance from the surface of a target object. That is, the optical characteristic setting unit 0022 sets the weight coefficients according to at least one voxel value of the plurality of pieces of volume data and the distance from the surface of the target object.

The optical characteristics in the embodiment are regulated by the weight coefficients set so that a behavior (action) of light is replicated based on the optical characteristics of a tissue, and are set by the optical characteristic setting unit 0022. The optical characteristic setting unit 0022 sets the luminance two-dimensional weight coefficient table 1601 which includes the weight coefficients as the optical characteristics of the elasticity volume data and the elasticity two-dimensional weight coefficient table 1604 which includes the weight coefficients as the optical characteristics of the elasticity volume data.

As illustrated in FIG. 37(a), two weight coefficients a7 and b7 are referred to from the luminance two-dimensional weight coefficient table 1601 based on the two indexes, the luminance value of the luminance volume data and the distance from a body surface (or the surface of a tissue). As illustrated in FIG. 37(b), two weight coefficients a8 and b8 are referred to from the elasticity two-dimensional weight coefficient table 1604 based on the two indexes, the elasticity value of the elasticity volume data and the distance from a body surface (or the surface of a tissue). In the embodiment, a case will be described in which either of the luminance two-dimensional weight coefficient table 1601 or the elasticity two-dimensional weight coefficient table 1604 is selected by a threshold value. For example, either of the luminance two-dimensional weight coefficient table 1601 or the elasticity two-dimensional weight coefficient table 1604 is selected based on the luminance threshold value d1 by comparing the luminance threshold value d1 to the luminance value corresponding to coordinates to be referred to.

The weight coefficients a7 and a8 are weight coefficients having an influence on (multiplied to) the input light source data and the weight coefficients b7 and b8 are weight coefficients having an influence on (multiplied to) the two-dimensional convolution integrated data. When the luminance two-dimensional weight coefficient table 1601 is selected by the luminance threshold value d1, the weight coefficients a7 and b7 referred to from the luminance two-dimensional weight coefficient table 1601 are multiplied to the input light source data and the two-dimensional convolution integrated data. In this case, a behavior (the degree of diffusion or the like) of light in the luminance volume data can be simply set by adjusting the magnitudes of the weight coefficients a7 and b7. When the elasticity two-dimensional weight coefficient table 1604 is selected by the luminance threshold value d1, the weight coefficients a8 and b8 referred to from the elasticity two-dimensional weight coefficient table 1604 are multiplied to the input light source data and the two-dimensional convolution integrated data. In this case, a behavior of light in the elasticity volume data can be simply set by adjusting the magnitudes of the weight coefficients a8 and b8.

A relation between the luminance volume data and the elasticity volume data can be adjusted by adjusting the luminance threshold value d1. For example, when the luminance value of the luminance volume data corresponding to coordinates to be referred to is equal to or greater than the luminance threshold value d1, the weight coefficient at the coordinates is referred to from the luminance two-dimensional weight coefficient table 1601. When the luminance value of the luminance volume data corresponding to the coordinates to be referred to is less than the luminance threshold value d1, the weight coefficient at the coordinates is referred to from the elasticity two-dimensional weight coefficient table 1604. As a result, the relation between the luminance volume data and the elasticity volume data (the relation between the luminance two-dimensional weight coefficient table 1601 and the elasticity two-dimensional weight coefficient table 1604) can be adjusted by the luminance threshold value d1.

Either of the luminance two-dimensional weight coefficient table 1601 or the elasticity two-dimensional weight coefficient table 1604 may be selected based on the elasticity threshold value d2 instead of the luminance threshold value d1 by comparing the elasticity threshold value d2 to the elasticity value corresponding to the coordinates to be referred to. For example, when the elasticity value of the elasticity volume data corresponding to coordinates to be referred to is equal to or greater than the elasticity threshold value d2, the weight coefficient at the coordinates is referred to from the elasticity two-dimensional weight coefficient table 1604. When the elasticity value of the elasticity volume data corresponding to the coordinates to be referred to is less than the elasticity threshold value d2, the weight coefficient at the coordinates is referred to from the luminance two-dimensional weight coefficient table 1601. As a result, the relation between the luminance volume data and the elasticity volume data (the relation between the luminance two-dimensional weight coefficient table 1601 and the elasticity two-dimensional weight coefficient table 1604) can be adjusted by the elasticity threshold value d2.

The luminance threshold value d1 and the elasticity threshold value d2 may be combined and either of the luminance two-dimensional weight coefficient table 1601 or the elasticity two-dimensional weight coefficient table 1604 may be selected. Either of the luminance two-dimensional weight coefficient table 1601 or the elasticity two-dimensional weight coefficient table 1604 may be selected by the plurality of luminance threshold values d1 or the plurality of elasticity threshold values d2. A new weight coefficient may be calculated by calculating an average or a weighted average of the weight coefficients of the luminance two-dimensional weight coefficient table 1601 and the elasticity two-dimensional weight coefficient table 1604.

Figure 38:
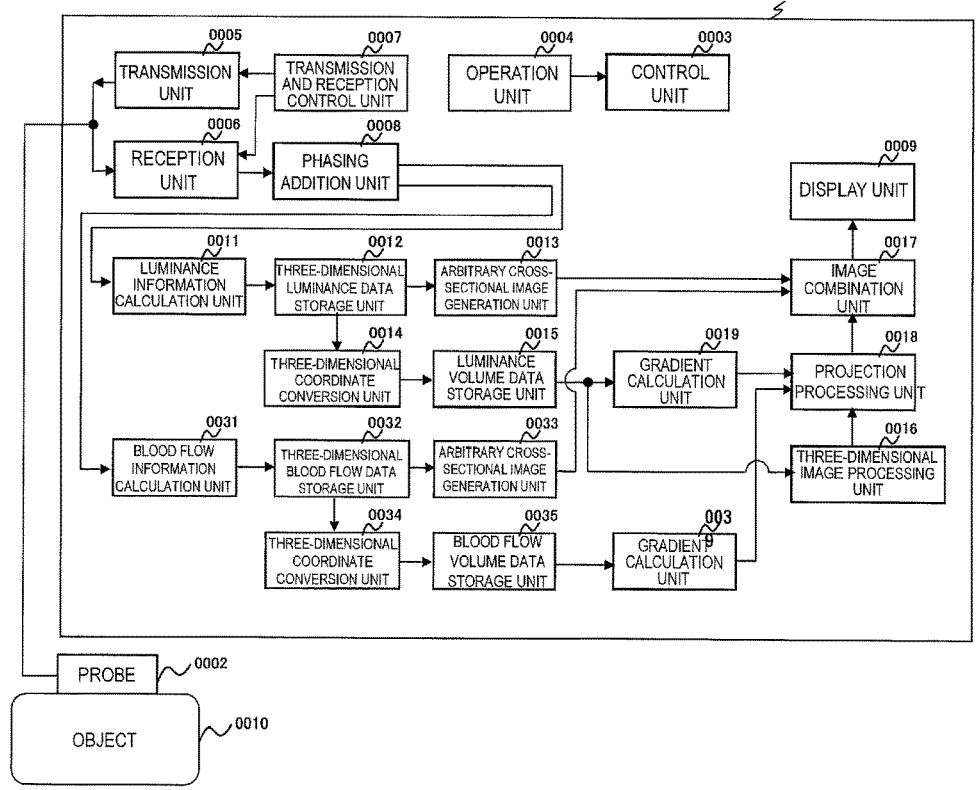
FIG. 38 is a block diagram illustrating a modification example of an ultrasonic diagnostic device.
Figure 39:
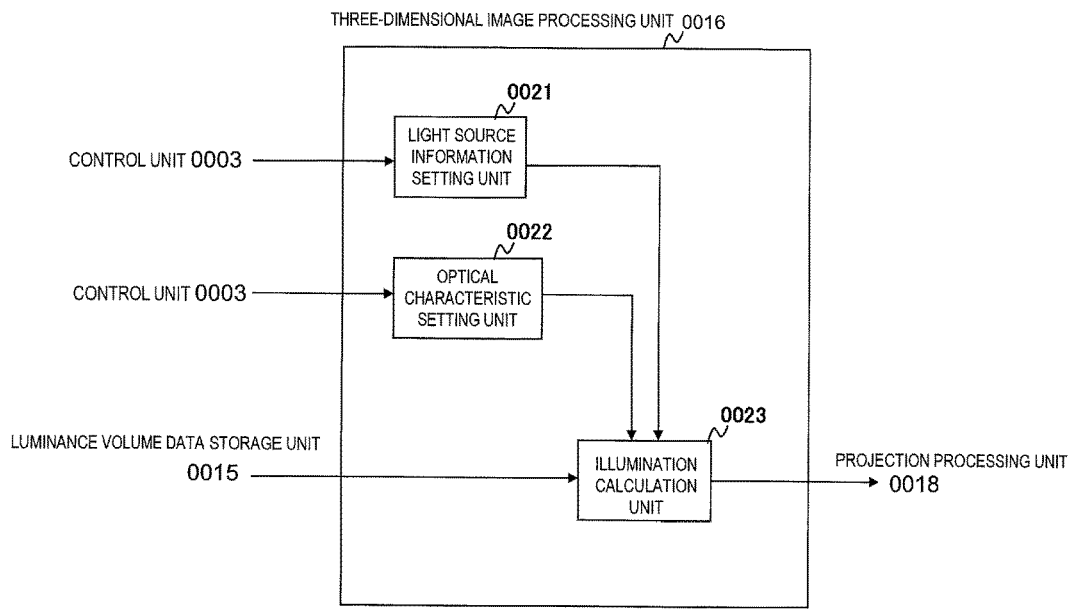
FIG. 39 is a block diagram illustrating a modification example of the three-dimensional image processing unit.

FIG. 38 is a block diagram illustrating a modification example of the embodiment. FIG. 39 is a conceptual diagram illustrating illumination calculation according to the modification example of the embodiment. As illustrated in FIGS. 38 and 39, unlike the second embodiment, the three-dimensional image processing unit 0016 inputs the luminance volume data from the luminance volume data storage unit 0015 and does not input the blood flow volume data from the blood flow volume data storage unit 0035. The three-dimensional image processing unit 0016 generates illumination volume data using the luminance volume data stored in the luminance volume data storage unit 0015 and does not generate the illumination volume data using the blood flow volume data stored in the blood flow volume data storage unit 0035. The blood flow volume data is subjected to a projection process by the projection processing unit 0018 without change.

The optical characteristic setting unit 0022 sets the weight coefficient indicating the optical characteristics of the luminance volume data in regard to the light source. The illumination calculation unit 0023 calculates the illumination of the position corresponding to coordinates of the luminance volume data based on the light source data and the weight coefficient and generates the illumination volume data based on the calculated illumination. The projection processing unit 0018 generates a three-dimensional image from a value of a color palette referred to from a blood flow value of the blood flow volume data and the illumination volume data.

The projection processing unit 0018 generates a three-dimensional image based on opacity to be referred to by the illumination of the illumination volume data and the value of the volume data (the luminance value of the luminance volume data or the blood flow value of the blood flow volume data) and a value of a color palette to be referred to from the blood flow value of the blood flow data. When the light source 0302 is the three primary colors, the projection processing unit 0018 generates the three-dimensional image from the three kinds of pieces of illumination volume data generated by the illumination calculation unit 0023, the luminance volume data stored in the luminance volume data storage unit 0015, and the blood flow volume data stored in the blood flow volume data storage unit 0035. A projection process in the projection processing unit 0018 is performed based on RGB values (r[k], g[k], and b[k]) for each voxel, opacity α[i], and gradient values S[i], as shown in equations (10) to (12) below, to generate the three-dimensional image. Here, the RGB values (r[k], g[k], and b[k]) for each voxel are values substituted with reference to either of the voxel values in the illumination volume data L_r[k], L_g[k], and L_b[k] of the respective wavelengths or the values (RGB values) of the color palette to be referred to from the blood flow value of the blood flow volume data. A three-dimensional image is generated by multiplying the RGB values (r[k], g[k], and b[k]) for each voxel, the opacity terms obtained by opacity α[i], and the value of the gradient values S[i] and performing accumulating in a visual line direction. In the equations, "k" indicates voxel coordinates in the visual line direction. The visual line direction is set as a direction in which an ultrasonic image is observed via the control unit 0003 by the operation unit 0004.

Here, the RGB values (r[k], g[k], and b[k]) for each voxel, the opacity α[i], and the gradient values S[i] are preferably set based on a threshold value (for example, the luminance threshold value c1 or the blood flow threshold value c2) from the opacity referred to by either of the luminance volume data or the blood flow volume data and the gradient value of either of the luminance gradient volume data or the blood flow gradient volume data. The opacity α[i] and the gradient value S[i] are set for each voxel. For example, when the luminance value of the luminance volume data corresponding to coordinates to be referred to in an i-th voxel in the visual line direction is equal to or greater than the luminance threshold value c1, the opacity α[i] referred to by the luminance volume data and the gradient value S[i] of the luminance gradient volume data are set. Further, when the blood flow value of the blood flow volume data corresponding to coordinates to be referred to in an i-th voxel in the visual line direction is equal to or greater than the blood flow threshold value c2, the opacity α[i] referred to by the blood flow volume data and the gradient value S[i] of the blood flow gradient volume data are set.

$$\mathrm{OUT\_}R[K]=\Sigma^{k=0:k}((r[k]\cdot S[k])\cdot \alpha[k]\cdot \Pi^{m=0:k-1}(1-\alpha[m])) \quad (10)$$

$$\mathrm{OUT\_}G[K]=\Sigma^{k=0:k}((g[k]\cdot S[k])\cdot \alpha[k]\cdot \Pi^{m=0:k-1}(1-\alpha[m])) \quad (11)$$

$$\mathrm{OUT\_}B[K]=\Sigma^{k=0:k}((b[k]\cdot S[k])\cdot \alpha[k]\cdot \Pi^{m=0:k-1}(1-\alpha[m])) \quad (12)$$

The three-dimensional image generated by the projection processing unit 0018 is disposed on the same screen as an arbitrary cross-sectional image by the image combination unit 0017 and is displayed by the display unit 0009. In this way, by superimposing the colors of the color palette to be referred to from the blood flow value of the blood flow volume data on a real three-dimensional image to which a behavior of light is added, it is possible to generate a three-dimensional image from which real shape information and functional information (blood flow information) can be simultaneously observed, thereby improving thus precision of ultrasonic inspection.

Figure 40:
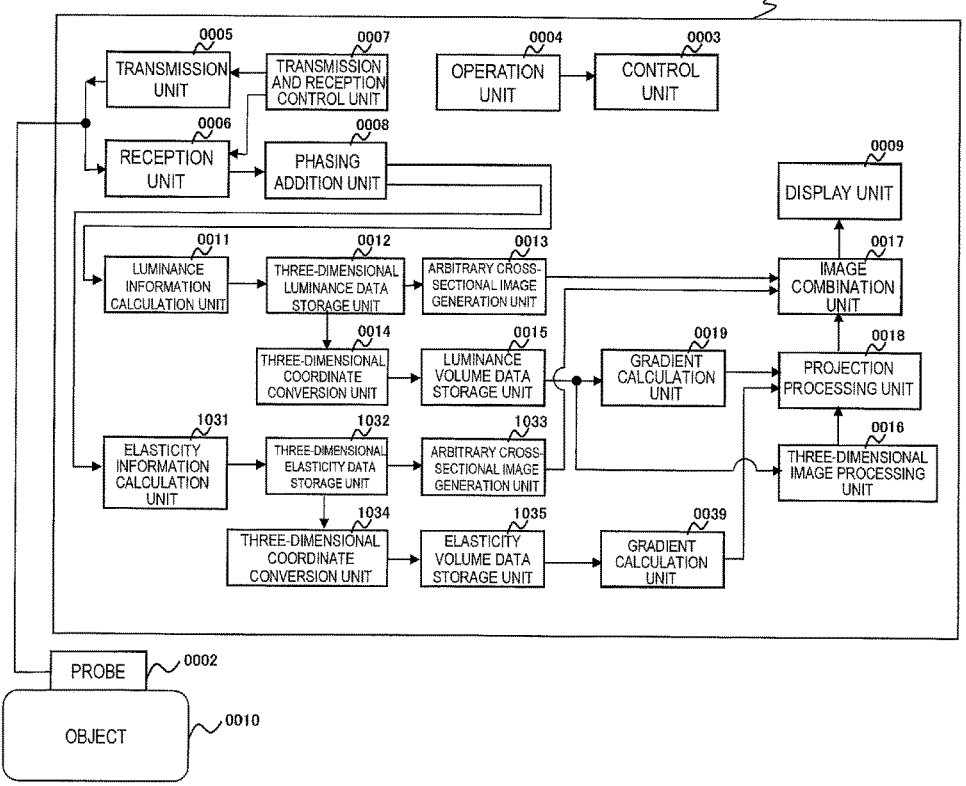
FIG. 40 is a block diagram illustrating another modification example of the ultrasonic diagnostic device.
Figure 41:
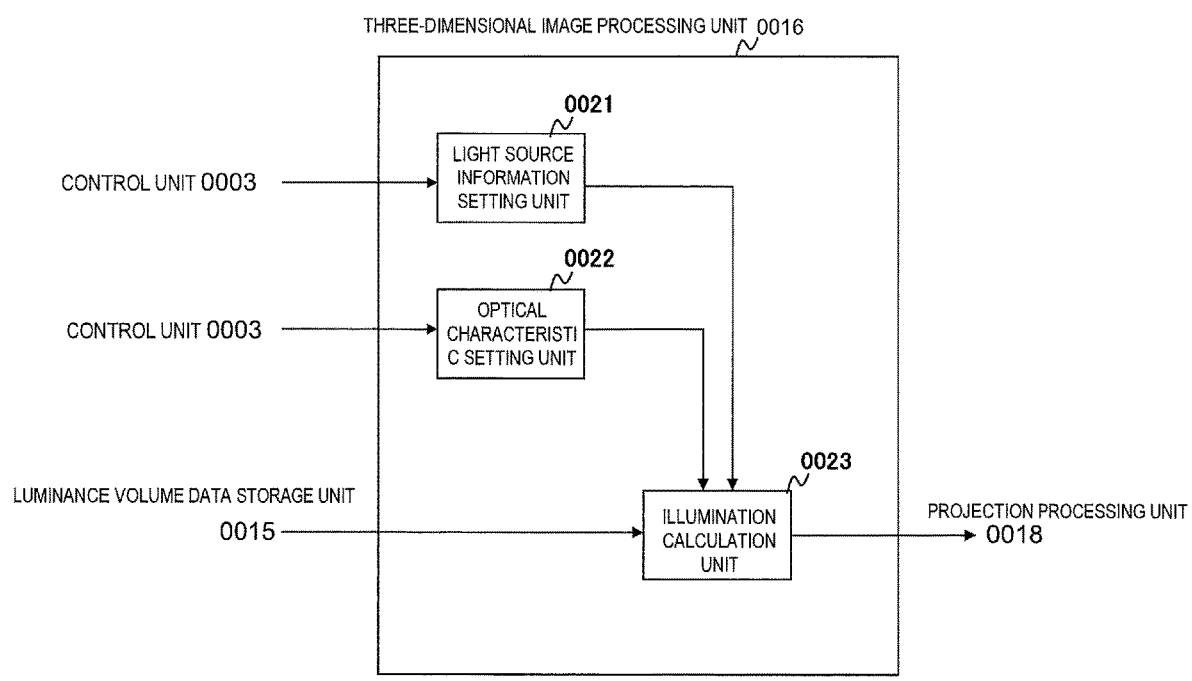
FIG. 41 is a block diagram illustrating another modification example of the three-dimensional image processing unit.

FIG. 40 is a block diagram illustrating a modification example of the embodiment. FIG. 41 is a conceptual diagram illustrating illumination calculation according to the modification example of the embodiment. As illustrated in FIGS. 40 and 41, unlike the third embodiment, the three-dimensional image processing unit 0016 inputs the luminance volume data from the luminance volume data storage unit 0015 and does not input the elasticity volume data from the elasticity volume data storage unit 1035. The three-dimensional image processing unit 0016 generates illumination volume data using the luminance volume data stored in the luminance volume data storage unit 0015 and does not generate the illumination volume data using the elasticity volume data stored in the elasticity volume data storage unit 1035. The elasticity volume data is subjected to a projection process by the projection processing unit 0018 without change. The optical characteristic setting unit 0022 sets the weight coefficient indicating the optical characteristics of the luminance volume data in regard to the light source. The illumination calculation unit 0023 calculates the illumination of the position corresponding to coordinates of the luminance volume data based on the light source data and the weight coefficient and generates the illumination volume data based on the calculated illumination. The projection processing unit 0018 generates a three-dimensional image from a value of a color palette referred to from an elasticity value of the elasticity volume data and the illumination volume data.

The projection processing unit 0018 generates a three-dimensional image based on opacity to be referred to by the illumination of the illumination volume data and the value of the volume data (the luminance value of the luminance volume data or the elasticity value of the elasticity volume data) and a value of a color palette to be referred to from the elasticity value of the elasticity volume data. When the light source 0302 is the three primary colors, the projection processing unit 0018 generates the three-dimensional image from the three kinds of pieces of illumination volume data generated by the illumination calculation unit 0023, the luminance volume data stored in the luminance volume data storage unit 0015, and the elasticity volume data stored in the elasticity volume data storage unit 1035. A projection process in the projection processing unit 0018 is performed based on RGB values (r[k], g[k], and b[k]) for each voxel, opacity α[i], and gradient values S[i], as shown in equations (13) to (15) below, to generate the three-dimensional image. Here, the RGB values (r[k], g[k], and b[k]) for each voxel are values substituted with reference to either of the voxel values in the illumination volume data L_r[k], L_g[k], and L_b[k] of the respective wavelengths or the values (RGB values) of the color palette to be referred to from the elasticity value of the elasticity volume data. A three-dimensional image is generated by multiplying the RGB values (r[k], g[k], and b[k]) for each voxel, the opacity terms obtained by opacity α[i], and the value of the gradient values S[i] and performing accumulating in a visual line direction. In the equations, "k" indicates voxel coordinates in the visual line direction. The visual line direction is set as a direction in which an ultrasonic image is observed via the control unit 0003 by the operation unit 0004.

Here, the RGB values (r[k], g[k], and b[k]) for each voxel, the opacity α[i], and the gradient values S[i] are preferably set based on a threshold value (for example, the luminance threshold value d1 or the elasticity threshold value d2) from the opacity referred to by either of the luminance volume data or the elasticity volume data and the gradient value of either of the luminance gradient volume data or the elasticity gradient volume data. The opacity α[i] and the gradient value S[i] are set for each voxel. For example, when the luminance value of the luminance volume data corresponding to coordinates to be referred to in an i-th voxel in the visual line direction is equal to or greater than the luminance threshold value d1, the opacity α[i] referred to by the luminance volume data and the gradient value S[i] of the luminance gradient volume data are set. Further, when the elasticity value of the elasticity volume data corresponding to coordinates to be referred to in an i-th voxel in the visual line direction is equal to or greater than the elasticity threshold value d2, the opacity α[i] referred to by the elasticity volume data and the gradient value S[i] of the elasticity gradient volume data are set.

$$\text{OUT\_}R[K]=\Sigma^{k=0:k}((r[k]\cdot S[k])\cdot\alpha[k]\cdot\Pi^{m=0:k-1}(1-\alpha[m])) \quad (13)$$

$$\text{OUT\_}G[K]=\Sigma^{k=0:k}((g[k]\cdot S[k])\cdot\alpha[k]\cdot\Pi^{m=0:k-1}(1-\alpha[m])) \quad (14)$$

$$\text{OUT\_}B[K]=\Sigma^{k=0:k}((b[k]\cdot S[k])\cdot\alpha[k]\cdot\Pi^{m=0:k-1}(1-\alpha[m])) \quad (15)$$

The three-dimensional image generated by the projection processing unit 0018 is disposed on the same screen as an arbitrary cross-sectional image by the image combination unit 0017 and is displayed by the display unit 0009.

In this way, by superimposing the colors of the color palette to be referred to from the elasticity value of the elasticity volume data on a real three-dimensional image to which a behavior of light is added, it is possible to generate a three-dimensional image from which real shape information and functional information (elasticity information) can be simultaneously observed, thereby improving thus precision of ultrasonic inspection.

In the second embodiment, the volume data is the luminance volume data and the blood flow volume data. In the third embodiment, the volume data is the luminance volume data and the elasticity volume data. However, the volume data may be at least two pieces of volume data among the luminance volume data, the blood flow volume data, and the elasticity volume data. In this case, the optical characteristic setting unit 0022 may set the weight coefficients according to at least one of the luminance volume data, the blood flow volume data, and the elasticity volume data and the distance from the surface of the target object. The optical characteristic setting unit 0022 may set the weight coefficients according to at least two pieces of volume data among the luminance volume data, the blood flow volume data, and the elasticity volume data. The optical characteristic setting unit 0022 may set the weight coefficients according to at least one of the luminance volume data, the blood flow volume data, and the elasticity volume data and the distance from the surface of the target object.

INDUSTRIAL APPLICABILITY

The present invention is useful as an ultrasonic diagnostic device and an ultrasonic three-dimensional image generation method that generate a three-dimensional image of which reality is improved by expressing interaction by diffusion, absorption, and the like of light in a tissue or between different tissues.

REFERENCE SIGNS LIST

0001 ultrasonic diagnostic device
0002 ultrasonic probe
0003 control unit
0004 operation unit
0005 transmission unit
0006 reception unit
0007 transmission and reception control unit
0008 phasing addition unit
0009 display unit
0011 luminance information calculation unit
0012 three-dimensional luminance data storage unit
0013, 0033, 1033 arbitrary cross-sectional image generation unit
0014, 0034, 1034 three-dimensional coordinate conversion unit
0015 luminance volume data storage unit
0016 three-dimensional image processing unit
0017 image combination unit
0018 projection processing unit
0019, 0039, 1039 gradient calculation unit
0021 light source information setting unit 0022 optical characteristic setting unit
0023 illumination calculation unit
0031 blood flow information calculation unit
0032 three-dimensional blood flow data storage unit
0035 blood flow volume data storage unit
0080 illumination correction unit
0081 correction optical characteristic setting unit
0082 correction light source information setting unit
0401 illumination volume data storage unit
0402 light source data retention unit
0403 two-dimensional convolution processing unit
0404, 1001 weighting addition unit
1002 correction illumination volume data storage unit
1031 elasticity information calculation unit
1032 three-dimensional elasticity data storage unit
1035 elasticity volume data storage unit

The invention claimed is:

1. An ultrasonic diagnostic device that displays a three-dimensional image of a target object based on at least one piece of volume data among luminance volume data, blood flow volume data, and elasticity volume data, the ultrasonic diagnostic device comprising:
a first processor configured to:
set light source data indicating characteristics of a light source set in a three-dimensional space according to a plurality of wavelengths;
set optical characteristics of the volume data in regard to the light source for each wavelength;
set a weight coefficient indicating the optical characteristics of the volume data in regard to the light source,
wherein the weight coefficient is regulated by a two-dimensional weight coefficient table in which the volume data and a distance from a surface of a target object are set as indexes, and the two-dimensional weight coefficient table is set for each wavelength, and
wherein the weight coefficient includes a first weight coefficient multiplied by the light source data and a second weight coefficient multiplied by two-dimensional convolution integrated data that is generated by performing two-dimensional convolution integration on the light source data; and
calculate illumination of a position according to coordinates of the volume data for each wavelength based on the light source data, the first weight coefficient and the second weight coefficient, and generate illumination volume data based on the calculated illumination; and
a second processor configured to generate the three-dimensional image from the generated illumination volume data.

2. The ultrasonic diagnostic device according to claim 1, wherein the volume data is at least two pieces of volume data among luminance volume data, blood flow volume data, and elasticity volume data, and
wherein the first processor is further configured to select one piece of volume data from between the two pieces of volume data at respective coordinates of the volume data, calculates the illumination of the position according to the coordinates based on the optical characteristics of the selected volume data, and generate the illumination volume data based on the calculated illumination.

3. The ultrasonic diagnostic device according to claim 1, wherein the volume data is luminance volume data and blood flow volume data, and
wherein the first processor is further configured to select one piece of volume data between the luminance volume data and the blood flow volume data at respective coordinates of the volume data, calculates the illumination of the position according to the coordinates based on the optical characteristics of the selected volume data, and generate the illumination volume data based on the calculated illumination.

4. The ultrasonic diagnostic device according to claim 1, wherein the volume data is luminance volume data and elasticity volume data, and
wherein the first processor is further configured to:
select one piece of volume data between the luminance volume data and the elasticity volume data at respective coordinates of the volume data, calculates the illumination of the position according to the coordinates based on the optical characteristics of the selected volume data, and generate the illumination volume data based on the calculated illumination.

5. The ultrasonic diagnostic device according to claim 1, wherein the first processor is further configured to set the weight coefficient according to at least one voxel value of luminance volume data, blood flow volume data, and elasticity volume data.

6. The ultrasonic diagnostic device according to claim 1, wherein the first processor is further configured to set the weight coefficient according to at least two voxel values of luminance volume data, blood flow volume data, and elasticity volume data.

7. The ultrasonic diagnostic device according to claim 1, wherein the first processor is further configured to set the weight coefficient according to at least two voxel values of luminance volume data, blood flow volume data, and elasticity volume data.

8. The ultrasonic diagnostic device according to claim 1, wherein at least one voxel value of luminance volume data, blood flow volume data, and elasticity volume data are set as indexes in the two-dimensional weight coefficient table.

9. The ultrasonic diagnostic device according to claim 1, wherein the two-dimensional weight coefficient table includes a luminance two-dimensional weight coefficient table in which a luminance value of luminance volume data and a distance from a surface of the target object are set as indexes and a blood flow two-dimensional weight coefficient table in which a blood flow value of blood flow volume data are set as indexes, and
wherein the first processor is further configured to select either of the luminance two-dimensional weight coefficient table or the blood flow two-dimensional weight coefficient table and calculates the illumination of the position according to the coordinates of the volume data based on the weight coefficient regulated in the selected luminance two-dimensional weight coefficient table and the selected blood flow two-dimensional weight coefficient table.

10. The ultrasonic diagnostic device according to claim 1, wherein the two-dimensional weight coefficient table includes a luminance two-dimensional weight coefficient table in which a luminance value of luminance volume data and a distance from a surface of the target object are set as indexes and an elasticity two-dimensional weight coefficient table in which a distance between an elasticity value of elasticity volume data and the surface of the target object is set as an index, and wherein the first processor is further configured to select either of the luminance two-dimensional weight coefficient table or the elasticity two-dimensional weight coefficient table and calculates the illumination of the position according to the coordinates of the volume data based on the weight coefficient regulated in the selected luminance two-dimensional weight coefficient table and the selected elasticity two-dimensional weight coefficient table.

11. The ultrasonic diagnostic device according to claim 1, wherein the second processor is further configured to generate a three-dimensional image from the illumination volume data and a value of a color palette referred to from a blood flow value of the blood flow volume data.

12. The ultrasonic diagnostic device according to claim 1, wherein the second processor is further configured to generate a three-dimensional image from the illumination volume data and a value of a color palette referred to from an elasticity value of the elasticity volume data.

13. The ultrasonic diagnostic device according to claim 1, wherein the first processor is further configured to convert a color tone of the illumination volume data based on at least one of the luminance volume data, the blood flow volume data, and the elasticity volume data.

14. The ultrasonic diagnostic device according to claim 13, wherein the first processor is further configured to:
generate a plurality of pieces of illumination volume data for each of a plurality of wavelengths of the light source; and
convert the color tone by exchanging values of the illumination of at least two pieces of the illumination volume data among the plurality of pieces of illumination volume data.

15. The ultrasonic diagnostic device according to claim 13, wherein the first processor is further configured to:
generate a plurality of pieces of the illumination volume data for each of a plurality of wavelengths of the light source; and
convert the color tone by performing at least one of addition, subtraction, multiplication, and division of a predetermined value on a value of the illumination of at least one piece of the illumination volume data among the plurality of pieces of illumination volume data.

16. An ultrasonic three-dimensional image generation method of displaying a three-dimensional image of a target object based on at least one piece of volume data among luminance volume data, blood flow volume data, and elasticity volume data, the ultrasonic three-dimensional image generation method comprising:
setting light source data indicating characteristics of a light source set in a three-dimensional space according to a plurality of wavelengths;
setting optical characteristics of the volume data in regard to the light source for each wavelength;
setting a weight coefficient indicating the optical characteristics of the volume data in regard to the light source,
wherein the weight coefficient is regulated by a two-dimensional weight coefficient table in which the volume data and a distance from a surface of a target object are set as indexes, and the two-dimensional weight coefficient table is set for each wavelength, and
wherein the weight coefficient includes a first weight coefficient multiplied by the light source data and a second weight coefficient multiplied by two-dimensional convolution integrated data that is generated by performing two-dimensional convolution integration on the light source data;
calculating illumination of a position according to coordinates of the volume data for each wavelength based on the light source data, the first weight coefficient and the second weight coefficient, and generating illumination volume data based on the calculated illumination; and
generating the three-dimensional image from the generated illumination volume data.

* * * * *